US006602510B1

(12) United States Patent
Fikes et al.

(10) Patent No.: US 6,602,510 B1
(45) Date of Patent: Aug. 5, 2003

(54) HLA CLASS I A2 TUMOR ASSOCIATED ANTIGEN PEPTIDES AND VACCINE COMPOSITIONS

(75) Inventors: John D. Fikes, San Diego, CA (US); Alessandro Sette, La Jolla, CA (US); John Sidney, San Diego, CA (US); Scott Southwood, Santee, CA (US); Esteban Celis, Rochester, MN (US); Elissa A. Keogh, San Diego, CA (US); Robert Chesnut, Cardiff-by-the-Sea, CA (US)

(73) Assignee: Epimmune Inc., San Diego, CA (US)

(*) Notice: Subject to any disclaimer, the term of this patent is extended or adjusted under 35 U.S.C. 154(b) by 0 days.

(21) Appl. No.: 09/543,608

(22) Filed: Apr. 5, 2000

(51) Int. Cl.[7] .................. A61K 38/08; A61K 38/10; A61K 9/127; C07K 7/06; C07K 7/08
(52) U.S. Cl. ................ 424/277.1; 530/324; 530/325; 530/326; 530/327; 530/328; 530/402; 424/192.1; 424/193.1; 424/450; 424/93.71; 514/2; 514/15; 514/14; 514/13; 514/12
(58) Field of Search ................ 530/328, 327, 530/326, 325, 324, 402; 424/277.1, 192.1, 193.1, 450, 93.71; 514/2, 15, 14, 13, 12; 435/372

(56) References Cited

U.S. PATENT DOCUMENTS 5,846,827 A  12/1998  Celis et al. ................ 435/384

FOREIGN PATENT DOCUMENTS

| WO | WO 98/338888 A1 | 8/1988 |
| WO | WO 94/20127 A1 | 9/1994 |
| WO | WO 95/04817 A1 | 2/1995 |

OTHER PUBLICATIONS

Bender, et al. "Improved Methods for the Generation of Dendritic Cells from Nonproliferating Progenitors in Human Blood" *J. of Immunological Methods* (1996) vol. 196, pp. 121–135.
Celis, et al. "Epitope Selection and Development of Peptides Based Vaccines to Treat Cancer" *Cancer Biology* (1995) vol. 6, pp. 329–336.
Celis, et al. "Identification of Potential CTL Epitopes of Tumor–Associated Antigen Mage–1 for Five–Common HLA–A Alleles" *Molecular Immunology* (1994) vol. 31(18), pp. 1423–1430.
Celis, et al. "Induction of Anti–tumor Cytotoxic T Lymphocytes in Normal Humans Using Primary Cultures and Synthetic Peptide Epitopes" *Proc. Natl. Acad. Sci.* (Mar. 1994) vol. 91, pp. 2105–2109.
Gaugler, et al. "Human Gene MAGE–3 Codes for an Antigen Recognized on a Melanoma by Autologous Cytolytic T Lymphocytes" *Ludwig Institute for Cancer Research, Brussels Branch* (Mar. 1994) vol. 179(3), pp. 921–930.

Kawakami, et al. "Recognition of Multiple Epitopes in the Human Melanoma Antigen gp100 by Tumor–Infiltrating T Lymphocytes Associated with In Vivo Tumor Regression" *J. of Immunology* (1995) vol. 154, pp. 3961–3968.
Kawashima, et al "The Multi–epitope Approach for Immunotherapy for Cancer: Identification of Several CTL Epitopes from Various Tumor–Associated Antigens Expressed on Solid Epithelial Tumors" *Human Immunology* (1998) vol. 59 pp. 1–14.
Nijman, et al. "p53, A Potential Target for Tumor–directed T Cells" *Immunology Letters* (1994) vol. 40, pp. 171–178.
Parkhurst, et al. "Improved Induction of Melanoma–Reactive CTL with Peptide from the Melanoma Antigen gp100 Modified at HLA–A*0201–Binding Residues" *J. of Immunology* (1996) pp. 2540–2547.
Ras, et al. "Identification of Potential HLA–A *0201 Restricted CTL Epitopes Derived from the Epithelial Cell Adhesion Molecule (Ep–CAM) and the Carcinoembryonic Antigen (CEA)" *Human Immunology* (1997) vol. 53, pp. 81–89.
Reynolds, et al "HLA–Independent Heterogeneity of CD8[+] T Cell Responses to MAGE–3, Melan–A/MART–1, gp100, Tyrosinase, MC1R, and TRP–2 in Vaccine–Treated Melanoma Patients" *J. of Immunology* (1998) vol. 161, pp. 6970–6976.
Rodriguez, et al. "Selective Transport of Internalized Antigens to the Cytosol for MHC Class I Presentation in Dendritic Cells" *Nature Cell Biology* (Oct. 1999) vol. 1, pp. 362–368.
Rongcun, et al. "Identification of New HER2/neu–Deived Peptide Epitopes That Can Elicit Specific CTL Against Autologous and Allogenic Carcinomas and Melanomas" *J. of Immunology* (1999) pp. 1037–1044.
Sette, et al. "HLA Supertypes and Supermotifs: A Functional Perspective on HLA Polymorphism" *Immunology* (1998) vol. 10, pp. 478–482.
Sidney, et al. "Practical, Biochemical and Evolutionary Implications of the Discovery of HLA class I Supermotifs" *Immunology Today* (1996) vol. 17(6), pp. 261–266.
Slingluff, et al. "Recognition of Human Melanoma Cells by HLA–A2.1–Restricted Cytotoxic T Lymphocytes is Mediated by at least Six Shared Peptide Epitopes" *J. of Immunology* (Apr. 1993) vol. 150(7), pp. 2955–2963.
Tsai, et al "Identification of Subdominant CTL Epitopes of the gp100 Melanoma–Associated Tumor Antigen by Primary In Vitro Immunization with Peptide–Pulsed Dendritic Cells" *J. of Immunology* (1997) vol. 158, pp. 1796–1802.
Watts, Colin "Dendritic Cells Spill the Beans" *Nature Cell Biology* (Oct. 1999) vol. 1, pp. E152–E154.

*Primary Examiner*—Ronald B. Schwadron
(74) *Attorney, Agent, or Firm*—Sterne, Kessler, Goldstein & Fox P.L.L.C.

(57) ABSTRACT

A composition or vaccine composition comprising eight isolated epitopes consisting of YLSGANLNV (SEQ. ID. NO: 1), IMIGVLVGV (SEQ. ID. NO: 2), KLBPVQLWV (SEQ. ID. NO: 3), SMPPPGTRV (SEQ. ID. NO: 4), KVAELVHFL (SEQ. ID. NO: 5), YLQLVFGIEV (SEQ. ID. NO: 6), RLLQETELV (SEQ. ID. NO: 7), and, VVLGVVFGI (SEQ. ID. NO: 8).

11 Claims, 5 Drawing Sheets

SEQUENCE LISTING

<160> NUMBER OF SEQ ID NOS: 52

<210> SEQ ID NO 1
<211> LENGTH: 9
<212> TYPE: PRT
<213> ORGANISM: Artificial Sequence
<220> FEATURE:
<223> OTHER INFORMATION: CEA.605V9

<400> SEQUENCE: 1

Tyr Leu Ser Gly Ala Asn Leu Asn Val
 1               5

<210> SEQ ID NO 2
<211> LENGTH: 9
<212> TYPE: PRT
<213> ORGANISM: Artificial Sequence
<220> FEATURE:
<223> OTHER INFORMATION: CEA.691

<400> SEQUENCE: 2

Ile Met Ile Gly Val Leu Val Gly Val
 1               5

<210> SEQ ID NO 3
<211> LENGTH: 9
<212> TYPE: PRT
<213> ORGANISM: Artificial Sequence
<220> FEATURE:
<223> OTHER INFORMATION: p53.139L2B3

<400> SEQUENCE: 3

Lys Leu Asx Pro Val Gln Leu Trp Val
 1               5

<210> SEQ ID NO 4
<211> LENGTH: 9
<212> TYPE: PRT
<213> ORGANISM: Artificial Sequence
<220> FEATURE:
<223> OTHER INFORMATION: p53.149M2

<400> SEQUENCE: 4

Ser Met Pro Pro Pro Gly Thr Arg Val
 1               5

<210> SEQ ID NO 5
<211> LENGTH: 9
<212> TYPE: PRT
<213> ORGANISM: Artificial Sequence
<220> FEATURE:
<223> OTHER INFORMATION: MAGE3.112

<400> SEQUENCE: 5

Lys Val Ala Glu Leu Val His Phe Leu
 1               5

<210> SEQ ID NO 6
<211> LENGTH: 10
<212> TYPE: PRT
<213> ORGANISM: Artificial Sequence
<220> FEATURE:
<223> OTHER INFORMATION: MAGE2.157

<400> SEQUENCE: 6

```
Tyr Leu Gln Leu Val Phe Gly Ile Glu Val
1               5                   10

<210> SEQ ID NO 7
<211> LENGTH: 9
<212> TYPE: PRT
<213> ORGANISM: Artificial Sequence
<220> FEATURE:
<223> OTHER INFORMATION: HER2/neu.689

<400> SEQUENCE: 7

Arg Leu Leu Gln Glu Thr Glu Leu Val
1               5

<210> SEQ ID NO 8
<211> LENGTH: 9
<212> TYPE: PRT
<213> ORGANISM: Artificial Sequence
<220> FEATURE:
<223> OTHER INFORMATION: HER2/neu.665

<400> SEQUENCE: 8

Val Val Leu Gly Val Val Phe Gly Ile
1               5

<210> SEQ ID NO 9
<211> LENGTH: 10
<212> TYPE: PRT
<213> ORGANISM: Artificial Sequence
<220> FEATURE:
<223> OTHER INFORMATION: CEA.233V10

<400> SEQUENCE: 9

Val Leu Tyr Gly Pro Asp Ala Pro Thr Val
1               5                   10

<210> SEQ ID NO 10
<211> LENGTH: 9
<212> TYPE: PRT
<213> ORGANISM: Artificial Sequence
<220> FEATURE:
<223> OTHER INFORMATION: CEA.687

<400> SEQUENCE: 10

Ala Thr Val Gly Ile Met Ile Gly Val
1               5

<210> SEQ ID NO 11
<211> LENGTH: 11
<212> TYPE: PRT
<213> ORGANISM: Artificial Sequence
<220> FEATURE:
<223> OTHER INFORMATION: p53.25V11

<400> SEQUENCE: 11

Leu Leu Pro Glu Asn Asn Val Leu Ser Pro Val
1               5                   10

<210> SEQ ID NO 12
<211> LENGTH: 9
<212> TYPE: PRT
<213> ORGANISM: Artificial Sequence
<220> FEATURE:
<223> OTHER INFORMATION: p53.139L2

<400> SEQUENCE: 12

Lys Leu Cys Pro Val Gln Leu Trp Val
```

```
1               5
```

```
<210> SEQ ID NO 13
<211> LENGTH: 9
<212> TYPE: PRT
<213> ORGANISM: Artificial Sequence
<220> FEATURE:
<223> OTHER INFORMATION: p53.149L2

<400> SEQUENCE: 13

Ser Leu Pro Pro Pro Gly Thr Arg Val
1               5

<210> SEQ ID NO 14
<211> LENGTH: 9
<212> TYPE: PRT
<213> ORGANISM: Artificial Sequence
<220> FEATURE:
<223> OTHER INFORMATION: Her2/neu.369L2V9

<400> SEQUENCE: 14

Lys Leu Phe Gly Ser Leu Ala Phe Val
1               5

<210> SEQ ID NO 15
<211> LENGTH: 9
<212> TYPE: PRT
<213> ORGANISM: Artificial Sequence
<220> FEATURE:
<223> OTHER INFORMATION: Her2/neu.369V2V9

<400> SEQUENCE: 15

Lys Val Phe Gly Ser Leu Ala Phe Val
1               5

<210> SEQ ID NO 16
<211> LENGTH: 10
<212> TYPE: PRT
<213> ORGANISM: Artificial Sequence
<220> FEATURE:
<223> OTHER INFORMATION: Her2/neu.773

<400> SEQUENCE: 16

Val Met Ala Gly Val Gly Ser Pro Tyr Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Her2/neu.5

<400> SEQUENCE: 17

Ala Leu Cys Arg Trp Gly Leu Leu Leu
1               5

<210> SEQ ID NO 18
<211> LENGTH: 9
<212> TYPE: PRT
<213> ORGANISM: Artificial Sequence
<220> FEATURE:
<223> OTHER INFORMATION: MAGE3.271

<400> SEQUENCE: 18

Phe Leu Trp Gly Pro Arg Ala Leu Val
1               5
```

```
<210> SEQ ID NO 19
<211> LENGTH: 9
<212> TYPE: PRT
<213> ORGANISM: Artificial Sequence
<220> FEATURE:
<223> OTHER INFORMATION: Her2/neu.48

<400> SEQUENCE: 19

His Leu Tyr Gln Gly Cys Gln Val Val
 1               5

<210> SEQ ID NO 20
<211> LENGTH: 9
<212> TYPE: PRT
<213> ORGANISM: Artificial Sequence
<220> FEATURE:
<223> OTHER INFORMATION: Her2/neu.435

<400> SEQUENCE: 20

Ile Leu His Asn Gly Ala Tyr Ser Leu
 1               5

<210> SEQ ID NO 21
<211> LENGTH: 9
<212> TYPE: PRT
<213> ORGANISM: Artificial Sequence
<220> FEATURE:
<223> OTHER INFORMATION: Her2/neu.369

<400> SEQUENCE: 21

Lys Ile Phe Gly Ser Leu Ala Phe Leu
 1               5

<210> SEQ ID NO 22
<211> LENGTH: 9
<212> TYPE: PRT
<213> ORGANISM: Artificial Sequence
<220> FEATURE:
<223> OTHER INFORMATION: CEA.24V9

<400> SEQUENCE: 22

Leu Leu Thr Phe Trp Asn Pro Pro Val
 1               5

<210> SEQ ID NO 23
<211> LENGTH: 10
<212> TYPE: PRT
<213> ORGANISM: Artificial Sequence
<220> FEATURE:
<223> OTHER INFORMATION: MAGE3.160

<400> SEQUENCE: 23

Leu Val Phe Gly Ile Glu Leu Met Glu Val
 1               5                  10

<210> SEQ ID NO 24
<211> LENGTH: 11
<212> TYPE: PRT
<213> ORGANISM: Artificial Sequence
<220> FEATURE:
<223> OTHER INFORMATION: MAGE3.159

<400> SEQUENCE: 24

Gln Leu Val Phe Gly Ile Glu Leu Met Glu Val
 1               5                  10
```

```
<210> SEQ ID NO 25
<211> LENGTH: 10
<212> TYPE: PRT
<213> ORGANISM: Artificial Sequence
<220> FEATURE:
<223> OTHER INFORMATION: Her2/neu.952

<400> SEQUENCE: 25

Tyr Met Ile Met Val Lys Cys Trp Met Ile
 1               5                  10

<210> SEQ ID NO 26
<211> LENGTH: 13
<212> TYPE: PRT
<213> ORGANISM: Artificial Sequence
<220> FEATURE:
<223> OTHER INFORMATION: PanDR binding peptide (PADRE)
<220> FEATURE:
<221> NAME/KEY: MOD_RES
<222> LOCATION: (3)...(3)
<223> OTHER INFORMATION: Xaa = cyclohexylalanine

<400> SEQUENCE: 26

Ala Lys Xaa Val Ala Ala Trp Thr Leu Lys Ala Ala Ala
 1               5                  10

<210> SEQ ID NO 27
<211> LENGTH: 13
<212> TYPE: PRT
<213> ORGANISM: Artificial Sequence
<220> FEATURE:
<223> OTHER INFORMATION: PanDR binding peptide (PADRE)

<400> SEQUENCE: 27

Ala Lys Phe Val Ala Ala Trp Thr Leu Lys Ala Ala Ala
 1               5                  10

<210> SEQ ID NO 28
<211> LENGTH: 13
<212> TYPE: PRT
<213> ORGANISM: Artificial Sequence
<220> FEATURE:
<223> OTHER INFORMATION: PanDR binding peptide (PADRE)

<400> SEQUENCE: 28

Ala Lys Tyr Val Ala Ala Trp Thr Leu Lys Ala Ala Ala
 1               5                  10

<210> SEQ ID NO 29
<211> LENGTH: 13
<212> TYPE: PRT
<213> ORGANISM: Artificial Sequence
<220> FEATURE:
<223> OTHER INFORMATION: PanDR binding peptide (PADRE)

<400> SEQUENCE: 29

Ala Lys Phe Val Ala Ala Tyr Thr Leu Lys Ala Ala Ala
 1               5                  10

<210> SEQ ID NO 30
<211> LENGTH: 13
<212> TYPE: PRT
<213> ORGANISM: Artificial Sequence
<220> FEATURE:
<223> OTHER INFORMATION: PanDR binding peptide (PADRE)
<220> FEATURE:
<221> NAME/KEY: MOD_RES
<222> LOCATION: (3)...(3)
```

<223> OTHER INFORMATION: Xaa = cyclohexylalanine

<400> SEQUENCE: 30

Ala Lys Xaa Val Ala Ala Tyr Thr Leu Lys Ala Ala Ala
 1               5                  10

<210> SEQ ID NO 31
<211> LENGTH: 13
<212> TYPE: PRT
<213> ORGANISM: Artificial Sequence
<220> FEATURE:
<223> OTHER INFORMATION: PanDR binding peptide (PADRE)

<400> SEQUENCE: 31

Ala Lys Tyr Val Ala Ala Tyr Thr Leu Lys Ala Ala Ala
 1               5                  10

<210> SEQ ID NO 32
<211> LENGTH: 13
<212> TYPE: PRT
<213> ORGANISM: Artificial Sequence
<220> FEATURE:
<223> OTHER INFORMATION: PanDR binding peptide (PADRE)

<400> SEQUENCE: 32

Ala Lys Phe Val Ala Ala His Thr Leu Lys Ala Ala Ala
 1               5                  10

<210> SEQ ID NO 33
<211> LENGTH: 13
<212> TYPE: PRT
<213> ORGANISM: Artificial Sequence
<220> FEATURE:
<223> OTHER INFORMATION: PanDR binding peptide (PADRE)
<220> FEATURE:
<221> NAME/KEY: MOD_RES
<222> LOCATION: (3)...(3)
<223> OTHER INFORMATION: Xaa = cyclohexylalanine

<400> SEQUENCE: 33

Ala Lys Xaa Val Ala Ala His Thr Leu Lys Ala Ala Ala
 1               5                  10

<210> SEQ ID NO 34
<211> LENGTH: 13
<212> TYPE: PRT
<213> ORGANISM: Artificial Sequence
<220> FEATURE:
<223> OTHER INFORMATION: PanDR binding peptide (PADRE)

<400> SEQUENCE: 34

Ala Lys Tyr Val Ala Ala His Thr Leu Lys Ala Ala Ala
 1               5                  10

<210> SEQ ID NO 35
<211> LENGTH: 13
<212> TYPE: PRT
<213> ORGANISM: Artificial Sequence
<220> FEATURE:
<223> OTHER INFORMATION: PanDR binding peptide (PADRE)

<400> SEQUENCE: 35

Ala Lys Phe Val Ala Ala Asn Thr Leu Lys Ala Ala Ala
 1               5                  10

<210> SEQ ID NO 36
<211> LENGTH: 13

-continued

```
<212> TYPE: PRT
<213> ORGANISM: Artificial Sequence
<220> FEATURE:
<223> OTHER INFORMATION: PanDR binding peptide (PADRE)
<220> FEATURE:
<221> NAME/KEY: MOD_RES
<222> LOCATION: (3)...(3)
<223> OTHER INFORMATION: Xaa = cyclohexylalanine

<400> SEQUENCE: 36

Ala Lys Xaa Val Ala Ala Asn Thr Leu Lys Ala Ala Ala
 1               5                  10

<210> SEQ ID NO 37
<211> LENGTH: 13
<212> TYPE: PRT
<213> ORGANISM: Artificial Sequence
<220> FEATURE:
<223> OTHER INFORMATION: PanDR binding peptide (PADRE)

<400> SEQUENCE: 37

Ala Lys Tyr Val Ala Ala Asn Thr Leu Lys Ala Ala Ala
 1               5                  10

<210> SEQ ID NO 38
<211> LENGTH: 14
<212> TYPE: PRT
<213> ORGANISM: Artificial Sequence
<220> FEATURE:
<223> OTHER INFORMATION: tetanus toxoid positions 830-843, Standard
      Peptide 553.01

<400> SEQUENCE: 38

Gln Tyr Ile Lys Ala Asn Ser Lys Phe Ile Gly Ile Thr Glu
 1               5                  10

<210> SEQ ID NO 39
<211> LENGTH: 21
<212> TYPE: PRT
<213> ORGANISM: Artificial Sequence
<220> FEATURE:
<223> OTHER INFORMATION: Plasmodium falciparum CS protein positions 378-
      398

<400> SEQUENCE: 39

Asp Ile Glu Lys Lys Ile Ala Lys Met Glu Lys Ala Ser Ser Val Phe
 1               5                  10                  15

Asn Val Val Asn Ser
            20

<210> SEQ ID NO 40
<211> LENGTH: 16
<212> TYPE: PRT
<213> ORGANISM: Artificial Sequence
<220> FEATURE:
<223> OTHER INFORMATION: Streptococcus 18 kD protein position 116

<400> SEQUENCE: 40

Gly Ala Val Asp Ser Ile Leu Gly Gly Val Ala Thr Tyr Gly Ala Ala
 1               5                  10                  15

<210> SEQ ID NO 41
<211> LENGTH: 13
<212> TYPE: PRT
<213> ORGANISM: Artificial Sequence
<220> FEATURE:
<223> OTHER INFORMATION: pan-DR-binding epitope
<220> FEATURE:
```

```
<221> NAME/KEY: MOD_RES
<222> LOCATION: (3)...(3)
<223> OTHER INFORMATION: Xaa = cyclohexylalanine, Phe or Tyr
<220> FEATURE:
<221> NAME/KEY: MOD_RES
<222> LOCATION: (7)...(7)
<223> OTHER INFORMATION: Xaa = Trp, Tyr, His or Asn

<400> SEQUENCE: 41

Ala Lys Xaa Val Ala Ala Xaa Thr Leu Lys Ala Ala Ala
 1               5                  10

<210> SEQ ID NO 42
<211> LENGTH: 9
<212> TYPE: PRT
<213> ORGANISM: Artificial Sequence
<220> FEATURE:
<223> OTHER INFORMATION: Standard Peptide 944.02

<400> SEQUENCE: 42

Tyr Leu Glu Pro Ala Ile Ala Lys Tyr
 1               5

<210> SEQ ID NO 43
<211> LENGTH: 10
<212> TYPE: PRT
<213> ORGANISM: Artificial Sequence
<220> FEATURE:
<223> OTHER INFORMATION: Standard Peptide 941.01

<400> SEQUENCE: 43

Phe Leu Pro Ser Asp Tyr Phe Pro Ser Val
 1               5                  10

<210> SEQ ID NO 44
<211> LENGTH: 9
<212> TYPE: PRT
<213> ORGANISM: Artificial Sequence
<220> FEATURE:
<223> OTHER INFORMATION: Standard Peptide 1072.34

<400> SEQUENCE: 44

Tyr Val Ile Lys Val Ser Ala Arg Val
 1               5

<210> SEQ ID NO 45
<211> LENGTH: 10
<212> TYPE: PRT
<213> ORGANISM: Artificial Sequence
<220> FEATURE:
<223> OTHER INFORMATION: Standard Peptide 941.12

<400> SEQUENCE: 45

Lys Val Phe Pro Tyr Ala Leu Ile Asn Lys
 1               5                  10

<210> SEQ ID NO 46
<211> LENGTH: 9
<212> TYPE: PRT
<213> ORGANISM: Artificial Sequence
<220> FEATURE:
<223> OTHER INFORMATION: Standard Peptide 940.06

<400> SEQUENCE: 46

Ala Val Asp Leu Tyr His Phe Leu Lys
 1               5
```

```
<210> SEQ ID NO 47
<211> LENGTH: 11
<212> TYPE: PRT
<213> ORGANISM: Artificial Sequence
<220> FEATURE:
<223> OTHER INFORMATION: Standard Peptide 1083.02

<400> SEQUENCE: 47

Ser Thr Leu Pro Glu Thr Tyr Val Val Arg Arg
  1               5                  10

<210> SEQ ID NO 48
<211> LENGTH: 9
<212> TYPE: PRT
<213> ORGANISM: Artificial Sequence
<220> FEATURE:
<223> OTHER INFORMATION: Standard Peptide 979.02

<400> SEQUENCE: 48

Ala Tyr Ile Asp Asn Tyr Asn Lys Phe
  1               5

<210> SEQ ID NO 49
<211> LENGTH: 9
<212> TYPE: PRT
<213> ORGANISM: Artificial Sequence
<220> FEATURE:
<223> OTHER INFORMATION: Standard Peptide 1075.23

<400> SEQUENCE: 49

Ala Pro Arg Thr Leu Val Tyr Leu Leu
  1               5

<210> SEQ ID NO 50
<211> LENGTH: 9
<212> TYPE: PRT
<213> ORGANISM: Artificial Sequence
<220> FEATURE:
<223> OTHER INFORMATION: Standard Peptide 1021.05

<400> SEQUENCE: 50

Phe Pro Phe Lys Tyr Ala Ala Ala Phe
  1               5

<210> SEQ ID NO 51
<211> LENGTH: 9
<212> TYPE: PRT
<213> ORGANISM: Artificial Sequence
<220> FEATURE:
<223> OTHER INFORMATION: DR7 preferred motif
<220> FEATURE:
<221> NAME/KEY: MOD_RES
<222> LOCATION: (1)...(1)
<223> OTHER INFORMATION: Xaa = Met, Phe, Leu, Ile, Val, Trp or Tyr
<220> FEATURE:
<221> NAME/KEY: MOD_RES
<222> LOCATION: (5)...(5)
<223> OTHER INFORMATION: Xaa = any amino acid
<220> FEATURE:
<221> NAME/KEY: MOD_RES
<222> LOCATION: (6)...(6)
<223> OTHER INFORMATION: Xaa = Ile, Val, Met, Ser, Ala, Cys, Thr, Pro
      or Leu
<220> FEATURE:
<221> NAME/KEY: MOD_RES
<222> LOCATION: (8)...(8)
<223> OTHER INFORMATION: Xaa = any amino acid except Asn
<220> FEATURE:
<221> NAME/KEY: MOD_RES
<222> LOCATION: (9)...(9)
<223> OTHER INFORMATION: Xaa = Ile or Val
```

```
<400> SEQUENCE: 51

Xaa Met Trp Ala Xaa Xaa Met Xaa Xaa
 1               5

<210> SEQ ID NO 52
<211> LENGTH: 9
<212> TYPE: PRT
<213> ORGANISM: Artificial Sequence
<220> FEATURE:
<223> OTHER INFORMATION: DR7 deleterious motif
<220> FEATURE:
<221> NAME/KEY: MOD_RES
<222> LOCATION: (1)...(1)
<223> OTHER INFORMATION: Xaa = any amino acid except Met, Phe, Leu,
      Ile, Val, Trp or Tyr
<220> FEATURE:
<221> NAME/KEY: MOD_RES
<222> LOCATION: (3)...(3)
<223> OTHER INFORMATION: Xaa = any amino acid except Trp
<220> FEATURE:
<221> NAME/KEY: MOD_RES
<222> LOCATION: (5)...(5)
<223> OTHER INFORMATION: Xaa = any amino acid
<220> FEATURE:
<221> NAME/KEY: MOD_RES
<222> LOCATION: (6)...(6)
<223> OTHER INFORMATION: Xaa = any amino acid except Ile, Val, Met, Ser,
      Ala, Cys, Thr, Pro or Leu
<220> FEATURE:
<221> NAME/KEY: MOD_RES
<222> LOCATION: (7)...(7)
<223> OTHER INFORMATION: Xaa = Gly, Arg or Asp

<400> SEQUENCE: 52

Xaa Cys Xaa Gly Xaa Xaa Xaa Asn Gly
 1               5
```

HLA CLASS I A2 TUMOR ASSOCIATED ANTIGEN PEPTIDES AND VACCINE COMPOSITIONS

Figure 1:
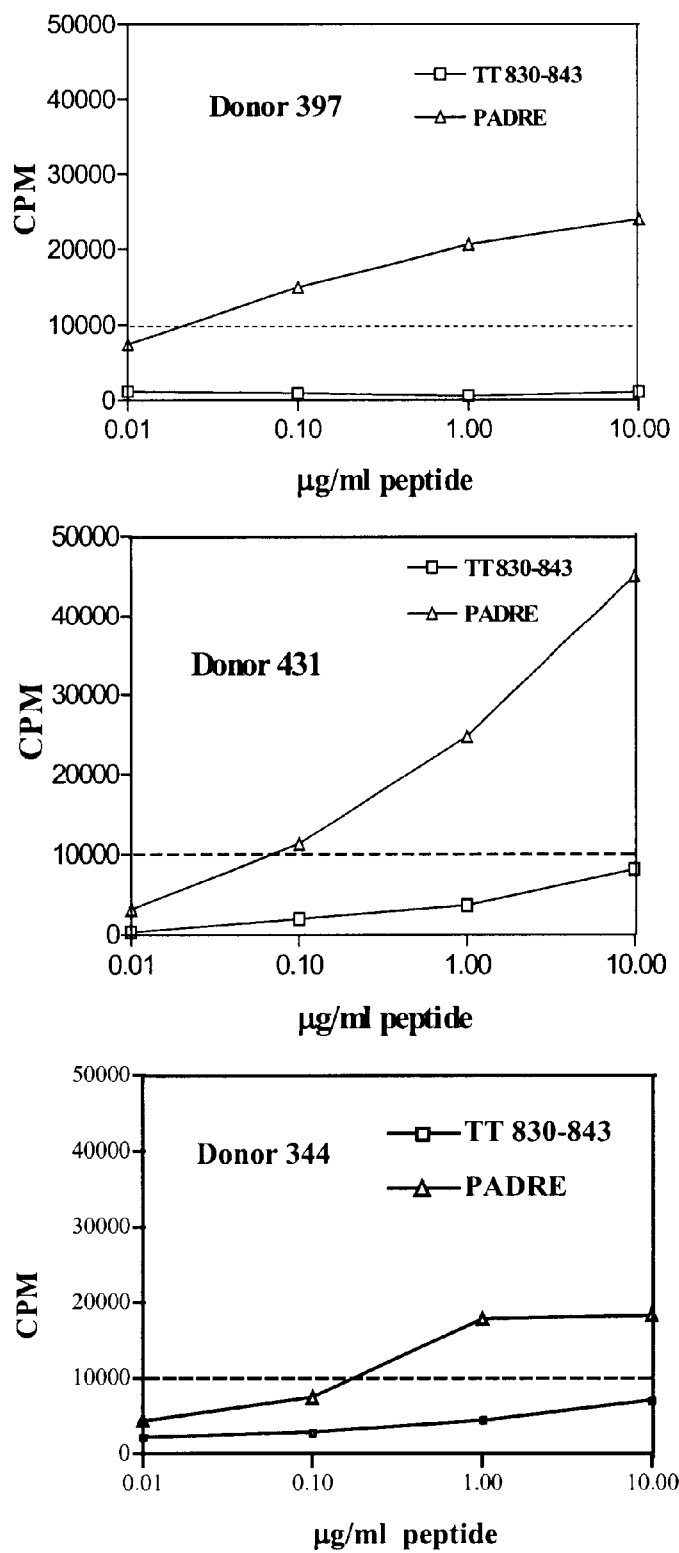

STATEMENT AS TO RIGHTS TO INVENTIONS MADE UNDER FEDERALLY SPONSORED RESEARCH AND DEVELOPMENT

This invention was funded, in part, by the United States government under grants with the National Institutes of Health. The U.S. government has certain rights in this invention.

FIELD OF THE INVENTION

This invention relates to the field of biology. In a particular embodiment, it relates to compositions useful to monitor or elicit an immune response to selected tumor-associated antigens.

Index
I. Background of the Invention
II. Summary of the Invention
III. Brief Description of the Figures
IV. Detailed Description of the Invention
  A. Definitions
  B. Stimulation of CTL and HTL responses
  C. Binding Affinity of Peptide Epitopes for HLA Molecules
  D. Peptide Epitope Binding Motifs and Supermotifs
    1. HLA-A2 supermotif
    2. HLA-A2.1 motif
    3. HLA Class II Motifs and PADRE™
  E. Enhancing Population Coverage of the Vaccine
  F. Immune Response-Stimulating Peptide Epitope Analogs
  G. Preparation of Peptide Epitopes
  H. Assays to Detect T-Cell Responses
  I. Use of Peptide Epitopes for Evaluating Immune Responses
  J. Vaccine Compositions
    1. Minigene Vaccines
    2. Combinations of CTL Peptides with Helper Peptides
    3. Combinations of CTL Peptides with T Cell Priming Materials
    4. Vaccine Compositions Comprising Dendritic Cells Pulsed with CTL and/or HTL Epitopes
  K. Administration of Vaccines for Therapeutic or Prophylactic Purposes
  L. Kits
V. Examples
VI. Claims
VII. Abstract

I. BACKGROUND OF THE INVENTION

The field of immunotherapy is yielding new approaches for the treatment of cancer, including the development of improved cancer vaccines (Krul, K. G., *Decision Resources*, 10.1–10.25 (1998)). While vaccines provide a mechanism of directing immune responses towards the tumor cells, there are a number of mechanisms by which tumor cells circumvent immunological processes (Pardoll, D. M., *Nature Medicine* (Vaccine Supplement), 4:525–531 (1998)). Recent advances indicate that the efficacy of peptide vaccines may be increased when combined with approaches which enhance the stimulation of immune responses, such as the use of Interleukin-2 or autologous dendritic cells (DC) (Abbas et al., eds., *Cellular and Molecular Immunology*, 3$^{rd}$ Edition, W. B. Saunders Company, pub. (1997)).

In a Phase I study, Murphy, et al., demonstrated that Human Leukocyte Antigen (HLA)-A2-binding peptides corresponding to sequences present in prostate specific antigen (PSA) stimulated specific cytotoxic T-cell lymphocyte (CTL) responses in patients with prostate cancer (Murphy et al., *The Prostate* 29:371–380 (1996)). Recently, Rosenberg, et al., evaluated the safety and mechanism of action of a synthetic HLA-A2 binding peptide derived from the melanoma associated antigen, gp100, as a cancer vaccine to treat patients with metastatic melanoma (Rosenberg et al., *Nature Med.*, 4:321–327 (1998)). Based on immunological assays, 91% of patients were successfully immunized with the synthetic peptide. In addition, 42% (13/31) of patients who received the peptide vaccine in combination with IL-2 treatment, demonstrated objective cancer responses. Finally, Nestle, et al., reported the vaccination of 16 melanoma patients with peptide- or tumor lysate-pulsed DC (Nestle et al., *Nature Med* 4:328–332 (1998)). Peptide-pulsed DC induced immune responses in (11/12) patients immunized with a vaccine comprised of 1–2 peptides. Objective responses were evident in 5/16 (3 peptide-pulsed, 2 tumor-lysate pulsed) evaluated patients in this study. These Phase I safety studies provided evidence that HLA-A2 binding peptides of known tumor-associated antigens demonstrate the expected mechanism of action. These vaccines were generally safe and well tolerated. Vaccine molecules related to four cancer antigens, CEA, HER2/neu, MAGE2, and, MAGE3 have been disclosed. (Kawashima et al., *Human Immunology*, 59:1–14 (1998)).

Preclinical studies have shown that vaccine-pulsed DC mediate anti-tumor effects through the stimulation of antigen-specific CTL (Mandelboim et al., *Nature Med.*, 1: 1179–1183 (1995); Celluzzi et al., *J Exp Med* 183:283–287 (1996); Zitvogel et al., *J Exp Med* 183:87–97 (1996); Mayordomo et al., *Nature Med* 1:1297–1302 (1995)). CTL directly lyse tumor cells and also secrete an array of cytokines such as interferon gamma (IFNγ), tumor necrosis factor (TNF) and granulocyte-macrophage colony stimulating factor (GM-CSF), that further amplify the immune reactivity against the tumor cells. CTL recognize tumor associated antigens (TAA) in the form of a complex composed of 8–11 amino acid residue peptide epitopes, bound to Major Histocompatibility Complex (MHC) molecules (Schwartz, B. D., *The human major histocompatibility complex HLA in basic & clinical immunology* Stites et al., eds., Lange Medical Publication: Los Altos, pp. 52–64, 4$^{th}$ ed.). Peptide epitopes are generated through intracellular processing of 3proteins. The processed peptides bind to newly synthesized MHC molecules and the epitope-MHC complexes are expressed on the cell surface. These epitope-MHC complexes are recognized by the T cell receptor of the CTL. This recognition event is required for the activation of CTL as well as induction of the effector functions such as lysis of the target tumor cell.

MHC molecules are highly polymorphic proteins that regulate T cell responses (Schwartz, B. D., *The human major histocompatibility complex HLA in basic & clinical immunology* Stites et al., eds., Lange Medical Publication: Los Altos, pp. 52–64, 4$^{th}$ ed.). The species-specific MHC homologues that display CTL epitopes in humans are termed HLA. HLA class I molecules can be divided into several families or "supertypes" based upon their ability to bind similar repertoires of peptides. Vaccines which bind to HLA supertypes such as A2, A3, and B7, will afford broad, non-ethnically biased population coverage. As seen in Table 11, population coverage is 84–90% for various ethnicities, with an average coverage of the sample ethnicities at 87%.

Various approaches have, or are, being employed as cancer vaccines. Table 1 overviews the major cancer vaccine approaches and the various advantages and disadvantages of each.

Currently there are a number of unmet needs in the area of cancer treatment. This is evidenced by the side effects associated with existing therapies employed for cancer treatment and the fact that less than 50% of patients are cured by current therapies. Therefore, an opportunity exists for a product with the ability to either increase response rates, duration of response, overall survival, disease free survival or quality of life.

II. SUMMARY OF THE INVENTION

Disclosed herein is a composition comprising all eight isolated epitopes: YLSGANLNV (SEQ ID NO:1), IMIGVLVGV (SEQ ID NO:2), KLBPVQLWV (SEQ ID NO:3), SMPPPGTRV (SEQ ID NO:4), KVAELVHFL (SEQ ID NO:5), YLQLVFGIEV (SEQ ID NO:6), RLLQETELV (SEQ IS NO:7), and VVLGVVFGI (SEQ ID NO:8). The composition can further comprise an antigen presenting cell, whereby at least one epitope is bound to an HLA molecule on the antigen presenting cell, such that a T lymphocyte receptor can bind to a complex of the HLA molecule and the epitope. The antigen presenting cell can be a dendritic cell. The composition can comprise each epitope connected to another epitope by peptide bonds. An amino acid linker can be a component of the composition, wherein at least two of the epitopes are connected to each other by peptide bonds. The composition can comprise a CTL or HTL epitope; the HTL epitope can be a pan-DR binding molecule. The composition can comprise a liposome, wherein the epitopes are on or within the liposome. A lipid can be attached to one of the epitopes.

In another embodiment, a composition can comprise at least one peptide, the peptide comprising an isolated, prepared epitope consisting of a sequence selected from the group consisting of: VLYGPDAPTV (SEQ ID NO:9), YLSGANLNV (SEQ ID NO:1), ATVGIMIGV (SEQ ID NO:10), LLPENNVLSPV (SEQ ID NO:11), KLCPVQLWV (SEQ ID NO:12), KLBPVQLWV (SEQ ID NO:3), SLPPPGTRV (SEQ ID NO:13), SMPPPGTRV (SEQ ID NO:4), KLFGSLAFV (SEQ ID NO:14), KVFGSLAFV (SEQ ID NO:15), VMAGVGSPYV (SEQ ID NO:16), ALCRWGLLL (SEQ ID NO:17), FLWGPPALV (SEQ ID NO:18), HLYQGCQVV (SEQ ID NO:19), ILHNGAYSL (SEQ ID NO:20), IMIGVLVGV (SEQ ID NO:2), KIFGSLAFL (SEQ ID NO:21), KVAELVHFL (SEQ ID NO:5), LLTFWNPPV (SEQ ID NO:22), LVFGIELMEV (SEQ ID NO:23), QLVFGIELMEV (SEQ ID NO:24), RLLQETELV (SEQ ID NO:7), VVLGVVFGI (SEQ ID NO:8), YLQLVFGIEV (SEQ ID NO:6), and YMIMVKCWMI (SEQ ID NO:25). The epitope can be joined to an amino acid linker. The epitope can be admixed or joined to a CTL epitope. The epitope can be admixed or joined to an HTL epitope, which can be a pan-DR binding molecule. The composition can further comprise a liposome, wherein the epitope is on or within the liposome. The epitope can be joined to a lipid. An epitope of the composition can br present as a heteropolymer or a homoplymer. The composition can comprise an HLA heavy chain, wherein the epitope contacts the HLA heavy chain. The HLA heavy chain can contact $\beta_2$-microglobulin, biotin or, streptavidin. The HLA heavy chain can contact $\beta_2$-microglobulin and biotin, and, the biotin can contact streptavidin, whereby a tetrameric complex is formed. The composition can further comprise an antigen presenting cell, wherein the epitope is on or within the antigen presenting cell. When the epitope is bound to an HLA molecule on the antigen presenting cell, whereby, when an A2-restricted cytotoxic lymphocyte (CTL) is present, a receptor of the CTL binds to a complex of the HLA molecule and the epitope. The antigen presenting cell can be a dendritic cell.

A further embodiment of the invention comprises a peptide comprising less than 50 contiguous amino acids that have 100% identity with a native peptide sequence of HER2/neu, MAGE2, MAGE3, p53, or CEA; the peptide further comprising an epitope selected from the group consisting of: YLSGANLNV (SEQ ID NO:1), KLBPVQLWV (SEQ ID NO:3), and SMPPPGTRV (SEQ ID NO:4). The peptide can comprise epitopes from two sequences selected from the group of native peptide sequences consisting of: HER2/neu, MAGE2, MAGE3, p53, and CEA. The peptide can comprise two or three epitopes selected from the group consisting of: YLSGANLNV (SEQ ID NO:1), KLBPVQLWV (SEQ ID NO:3), and SMPPPGTRV (SEQ ID NO:4). The peptide can comprise an additional epitope. The additional epitope can be selected from the group consisting of: ALCRWGLLL (SEQ ID NO:17), FLWGPRALV (SEQ ID NO:18), HLYQGCQVV (SEQ ID NO:19), ILHNGAYSL (SEQ ID NO:20), IMIGVLVGV (SEQ ID NO:2), KIFGSLAFL (SEQ ID NO:21), KVAELVHFL (SEQ ID NO:5), LLTFWNPPV (SEQ ID NO:22), LVFGIELMEV (SEQ ID NO:23), QLVFGIE (SEQ ID NO:24), RLLQETELV (SEQ ID NO:7), VVLGVVFGI (SEQ ID NO:8), YLQLVFGIEV (SEQ ID NO:6), and YMIMVKCWMI (SEQ ID NO:25). The additional epitope can be selected from the group consisting of: IMIGVLVGV (SEQ ID NO:2), KVAELVHFL (SEQ ID NO:5), YLQLVFGIEV (SEQ ID NO:6), RLLQETELV (SEQ ID NO:7), and VVLGVVFGI (SEQ ID NO:8). The additional epitope can be selected from the group consisting of: VLYGPDAPTV (SEQ ID NO:9), YLSGANLNV (SEQ ID NO:1), ATVGIMIGV (SEQ ID NO:10), LLPENNVLSPV (SEQ ID NO:11), KLCPVQLWV (SEQ ID NO:12), KLBPVQLWV (SEQ ID NO:3), SLPPPGTRV (SEQ ID NO:13), SMPPPGTRV (SEQ ID NO:4), KLFGSLAFV (SEQ ID NO:14), KVFGSLAFV (SEQ ID NO:15), and VMAGVGSPYV (SEQ ID NO:16). The additional epitope can be a PanDR binding molecule. The peptide can be a heteropolymer or a homopolymer.

An alternative embodiment of the invention is a composition comprising one or more peptides, and further comprising at least six epitopes selected from the group consisting of: YLSGANLNV (SEQ ID NO:1), IMIGVLVGV (SEQ ID NO:2), KLBPVQLWV (SEQ ID NO:3), SMPPGTRV (SEQ ID NO:4), KVAELVHFL (SEQ ID NO:5), YLQLVFGIEV (SEQ ID NO:6), RLLQETELV (SEQ ID NO:7), and VVLGVVFGI (SEQ ID NO:8), wherein each of said one or more peptides comprise less than 50 contiguous amino acids that have 100% identity with a native peptide sequence. The composition can comprise one peptide that comprises the at least six epitopes. The composition can comprise an epitope from p53. The composition can comprise seven or eight epitopes selected from the group consisting of: YLSGANLNV (SEQ ID NO:1), IMIGVLVGV (SEQ ID NO:2), KLBPVQLWV (SEQ ID NO:3), SMPPGTRV (SEQ ID NO:4), KVAELVHFL (SEQ ID NO:5), YLQLVFGIEV (SEQ ID NO:6), RLLQETELV (SEQ ID NO:7), and VVLGVVFGI (SEQ ID NO:8). The peptide of the composition can be a heteropolymer or a homopolymer.

The composition can further comprise an additional epitope. The additional epitope can be derived from a tumor associated antigen, or be a PanDR binding molecule.

A further embodiment of the invention comprises a vaccine composition comprising: a unit dose of a peptide that comprises less than 50 contiguous amino acids that have 100% identity with a native peptide sequence of CEA, HER2/neu, MAGE2, MAGE3, or p53; the peptide comprising an epitope selected from the group consisting of: VLYG-PDAPTV (SEQ ID NO:9), YLSGANLNV (SEQ ID NO:1), ATVGIMIGV (SEQ ID NO:10), LLPENNVLSPV (SEQ ID NO:11), KLCPVQLWV (SEQ ID NO:12), KLBPVQLWV (SEQ ID NO:3), SLPPPGTRV (SEQ ID NO:13), SMPP-PGTRV (SEQ ID NO:4), KLFGSLAFV (SEQ ID NO:14), KVFGSLAFV (SEQ ID NO:15), VMAGVGSPYV (SEQ ID NO:16), ALCRWGLLL (SEQ ID NO:17), FLWGPRALV (SEQ ID NO:18), HLYQGCQVV (SEQ ID NO:19), ILH-NGAYSL (SEQ ID NO:20), IMIGVLVGV (SEQ ID NO:2), KIFGSLAFL (SEQ ID NO:21), KVAELVHFL (SEQ ID NO:5), LLTFWNPPV (SEQ ID NO:22), LVFGIELMEV (SEQ ID NO:23), QLVFGIELMEV (SEQ ID NO:24), RLLQETELV (SEQ ID NO:7), VVLGVVFGI (SEQ ID NO:8), YLQLVFGIEV (SEQ ID NO:6), and YMIM-VKCWMI (SEQ ID NO:25); and; a pharmaceutical excipient. The composition can further comprise an additional epitope. The additional epitope can be selected from the group consisting of: ALCRWGLLL (SEQ ID NO:17), FLWGPRALV (SEQ ID NO:18), HLYQGCQVV (SEQ ID NO:19), ILHNGAYSL (SEQ ID NO:20), IMIGVLVGV (SEQ ID NO:2), KIFGSLAFL (SEQ ID NO:21), KVAELVHFL (SEQ ID NO:5), LLTFWNPPV (SEQ ID NO:22), LVFGIELMEV (SEQ ID NO:23), QLVF-GIELMEV (SEQ ID NO:24), RLLQETELV (SEQ ID NO:7), VVLGVVFGI (SEQ ID NO:8), YLQLVFGIEV (SEQ ID NO:6), and YMIMVKCWMI (SEQ ID NO:25). The additional epitope can be a PanDR binding molecule. The pharmnaceutical excipient can comprise an adjuvant. The vaccine composition can flirther comprise an antigen presenting cell, whereby when the epitope is bound to an HLA molecule on the antigen presenting cell, and when an A2 supertype-restricted cytotoxic T lymphocyte (CTL) is present, a receptor of the CTL binds to a complex of the HLA molecule and the epitope. The antigen presenting cell can be a dendritic cell. The vaccine composition can further comprise a liposome, wherein the at least one epitope is on or within the liposome.

Disclosed herein is a composition comprising one or more peptides, and further comprising at least one epitope selected from Table 6, wherein each of said one or more peptides comprise less than 250, 100, 75 or 50 contiguous amino acids that have 100% identity with a native peptide sequence. The native peptide sequence can be from an antigen selected from the group consisting of CEA, HER2/neu, MAGE2, MAGE3, p53 and a prostate tumor associated antigen. The at least one epitope can be YLSGANLNV (SEQ ID NO:1), IMIGVLVGV (SEQ ID NO:2), KLB-PVQLWV (SEQ ID NO:3), SMPPPGTRV (SEQ ID NO:4), KVAELVHFL (SEQ ID NO:5), YLQLVFGIEV (SEQ ID NO:6), RLLQETELV (SEQ ID NO:7), and VVLGVVFGI (SEQ ID NO:8). The composition can further comprise a pharmaceutical excipient, such as an adjuvant.

An alternative embodiment comprises, a composition comprising one or more peptides, and further comprising at least two epitopes selected from Table 6, wherein each of said one or more peptides comprise less than 250, 100, 75 or 50 amino acids that have 100% identity with a native peptide sequence. A native peptide sequence can be CEA, HER2/ neu, MAGE2, MAGE3, or p53. The composition comprises epitopes from at least two antigens selected from the group consisting of antigens: CEA, HER2/neu, MAGE2, MAGE3, and p53. The composition can comprise at least two, three, four, five, six, seven, eight, nine, 10, 11, 12, 13, 14, 15, 16, 17, 18, 19 or more epitopes selected from Table 6. A multiepitope peptide can be a heteropolymer or a homopolymer. The composition can comprise at least one epitope selected from Table 6 which binds to a member of an HLA-A2 supertype at an $IC_{50}$ equal to or less than 500 nM, at least one epitope selected from Table 6 which binds to at least two members of the HLA-A2 supertype at an $IC_{50}$ equal to or less than 500 nM, at least one epitope selected from Table 6 which binds to at least three members of the HLA-A2 supertype at an $IC_{50}$ at equal to or less than 500 nM, at least one epitope selected from Table 6 which binds to a member of the HLA-A2 supertype at an $IC_{50}$ at equal to or less than 200 nM, at least one epitope selected from Table 6 which binds to a member of the HLA-A2 supertype at an $IC_{50}$ at equal to or less than 50 nM, or, at least one epitope selected from Table 6 which exhibits tumor cell recognition when used in a CTL assay to elicit a CTL response. The composition can comprise a pharmaceutical excipient, such as an adjuvant.

Also disclosed is a vaccine composition comprising: a unit dose form of a prepared peptide comprising an epitope set forth in Table 6, wherein the peptide comprises less than 250, 200, 150, 100, 75, 50, 40, 35, 30, 25, 20 or 15 amino acids that have 100% identity with a native peptide sequence; and, a pharmaceutical excipient. The vaccine composition can comprise less than 250 contiguous amino acids that have 100% identity with a native peptide sequence which is CEA, HER2/neu, MAGE2, MAGE3, or p53. The vaccine composition can comprise at least one epitope selected from Table 6 that is modified by lipidation, i.e., lipidated. The pharmaceutical excipient of the vaccine composition can comprise an adjuvant. A vaccine composition can comprise an antigen presenting cell, wherein at least one epitope selected from Table 6 is bound to an HLA molecule on the antigen presenting cell, whereby a T lymphocyte receptor can bind to a complex of the HLA molecule and the at least one peptide. The antigen presenting cell can be a dendritic cell. The vaccine composition can comprise at least one epitope selected from Table 6 that is comprised by a liposome.

A composition in accordance with any embodiment of the invention can further comprise a PanDR binding molecule, such as aKXVAAWTLKAAa, aKFVAAWTLKAAa, aKYVAAWTLKAAa, aKFVAAYTLKAAa, aKXVAAYTLKAAa, aKYVAAYTLKAAa, aKFVAAHTLKAAa, aKXVAAHTLKAAa, aKYVAAHTLKAAa, aKFVAANTLKAAa, aKXVAANTLKAAa, aKYVAANTLKAAa, AKXVAAW-TLKAAA (SEQ ID NO:26), AKFVAAWTLKAAA (SEQ ID NO:27), AKYVAAWTLKAAA (SEQ ID NO:28), AKFVAAYTLKAAA (SEQ ID NO:29), AKXVAAYTL-KAAA (SEQ ID NO:30), AKYVAAYTLKAAA (SEQ ID NO:31), AKFVAAHTLKAAA (SEQ ID NO:32), AKX-VAAHTLKAAA (SEQ ID NO:33), AKYVAAHTLKAAA (SEQ ID NO:34), AKFVAANTLKAAA (SEQ ID NO:35), AKXVAANTLKAAA (SEQ ID NO:36), or AKYVAANTL-KAAA (SEQ ID NO:37) (a=D-alanine, X=cyclohexylalanine). The PanDR molecule(s) can be amnidated.

III. BRIEF DESCRIPTION OF THE DRAWINGS

FIG. 1 depicts that PADRE promotes antigen specific T cell responses from human PBMC. In FIG. 1, PBMC from three healthy donors (donors 431, 397, and 344) were stimulated in vitro. In brief, Ficoll-Paque (Pharmacia LKB) purified PBMC were plated at 4×10⁶ cells/well in a 24-well tissue culture plate (Costar). The peptides were added at a final concentration of 10 μg/ml and incubated at 37° C. for 4 days. Recombinant interleukin-2 was added at a final concentration of 10 ng/ml and the cultures were fed every three days with fresh media and cytokine. Two additional stimulations of the T cells with antigen were performed on approximately days 14 and 28. The T cells (3×10⁵ cells/well) were restimulated with 10 μg/ml peptide using irradiated (7500 rads) autologous PBMC cells. T cell proliferative responses were determined using a ³H-thymidine incorporation assay.

Figure 2:
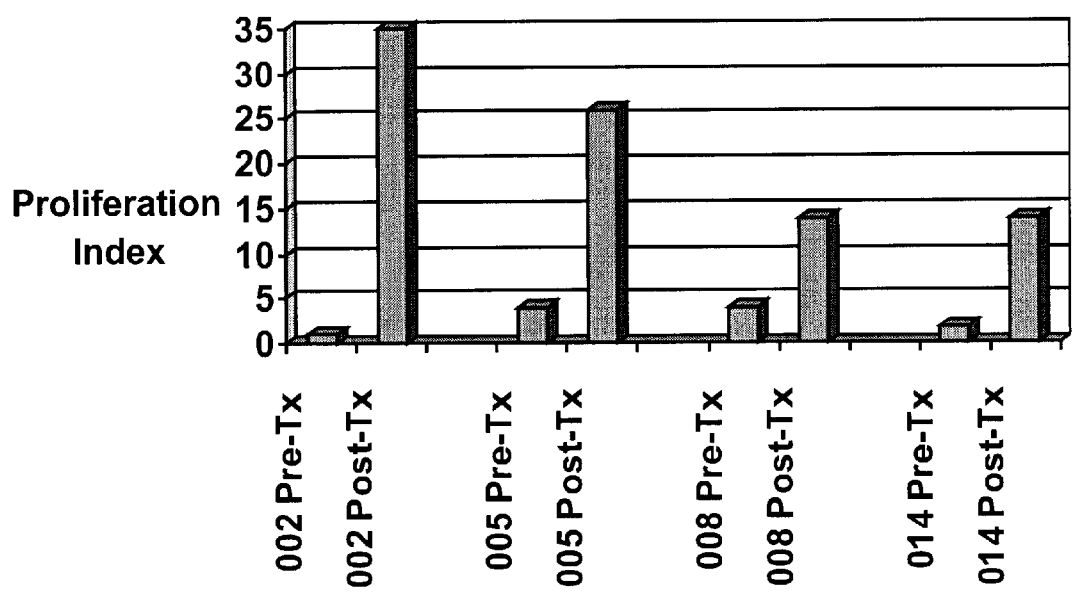

FIG. 2 depicts that PADRE®-specific proliferative responses are induced via peptide vaccination. In FIG. 2, two weeks after vaccination, PBMC of 4 out of 12 cervical cancer patients (002, 005, 008, and 014) displayed proliferation when stimulated in vitro with 5 μg/ml PADRE® peptide (4/12=33% responding patients, 95% interval 10–65%) (Tx=treatment). The proliferation index of multiple wells was calculated as the mean cpm from experimental wells divided by the mean cpm from control wells. PADRE®-specific responses were considered positive when the proliferation index exceeded 5. The variation between replicates was always less than 25% (Ressing et al., Detection of immune responses to helper peptide, but not to viral CTL epitopes, following peptide vaccination of immunocompromised patients with recurrent cervical carcinoma. Submitted (1999)).

Figure 3:
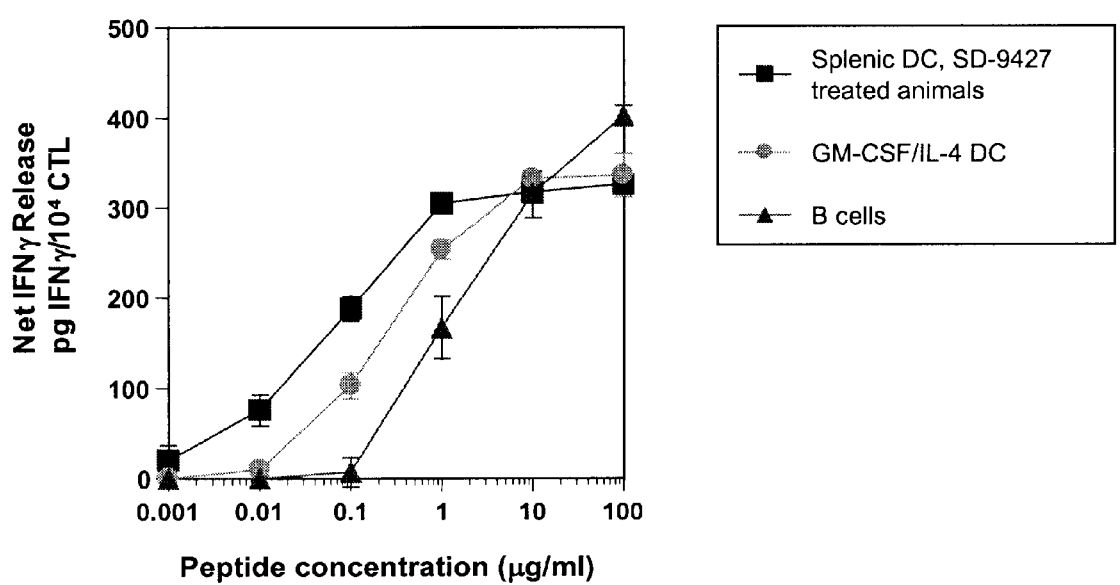

FIG. 3 depicts that splenic DC from ProGP-treated mice present HBV-derived CTL epitopes to a CTL line. In FIG. 3, Splenic DC from ProGP-treated HLA-A2.1/K$^b$-H-2$^{bxs}$ transgenic mice (33 μg/animal, QD, SC for 7 days) were enriched using an anti-CD11c antibody (Miltenyi Biotec). B cells were isolated from normal spleen by magnetic separation after treating cells with biotinylated anti-CD19 antibody and Strepavidin-coupled beads (Miltenyi Biotec). DC were also generated from bone marrow cells by culture with GM-CSF/IL-4. DC or B cells, (1×10⁵ cells) were incubated with 1×10⁴ CTL line 1168 and varying concentrations of the HBV Pol 455 peptide in Opti-MEM I medium containing 3 μg/ml β2-microglobulin (Scripps Laboratories). Cells were added to 96-flat bottom well ELISA plates that were pre-coated with an anti-IFNγ capture antibody. After incubation for 18–20 hr at 37° C., in situ production of IFNγ by stimulated line 1168 was measured using a sandwich ELISA. Data shown is from one experiment. Similar results have been obtained in additional experiments. Studies were performed at Epimmune Inc., San Diego, Calif.

Figure 4:
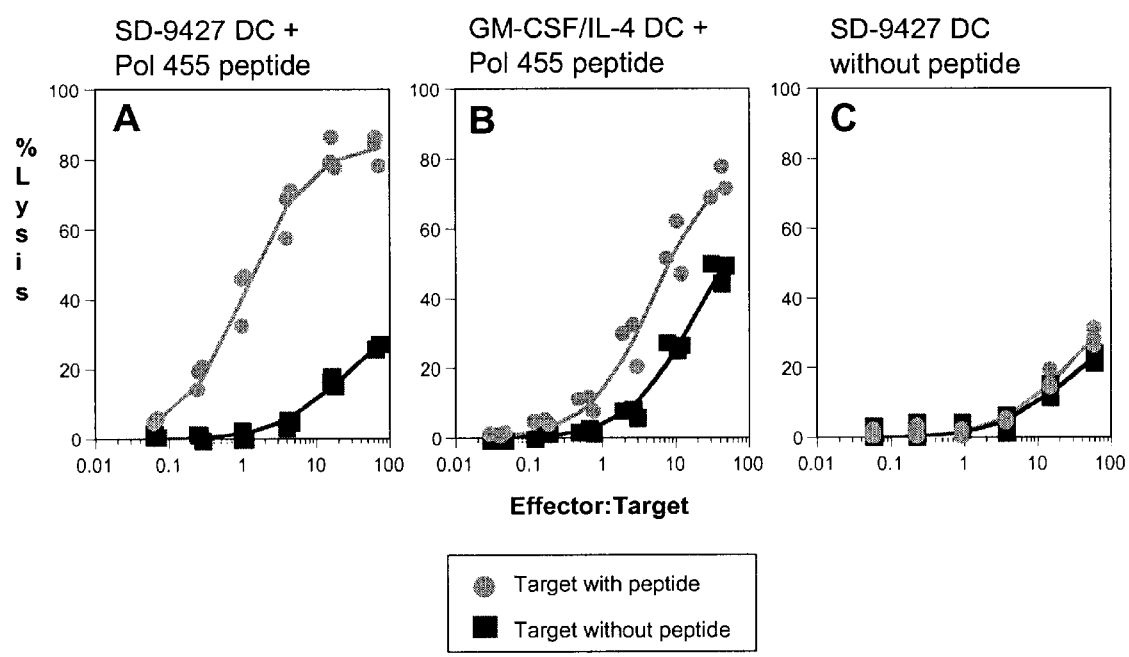

FIG. 4 depicts that splenic DC from ProGP-treated mice induce CTL responses in vivo. In FIG. 4, Splenic DC from ProGP treated HLA-A2.1 transgenic mice (33 μg/mouse, QD, SC for 7 days) were pulsed in vitro with HBV Pol 455 peptide (10⁶ cell per ml peptide at 10 μg/ml) in Opti-MEM I medium (Gibco Life Sciences) containing 3 μg/ml β2-microglobulin (Scripps Laboratories). After peptide pulsing for 3 hr at room temperature, DC were washed twice and 10⁶ cells were injected IV into groups of three transgenic mice. Epitope-pulsed GM-CSF/IL-4 expanded DC and "mock-pulsed" ProGP derived DC were also tested for comparison. Seven days after receiving the primary immunization with DC, animals were boosted with the same DC populations. At fourteen days after the primary immunization, spleen cells from immunized animals were restimulated twice in vitro in the presence of the Pol 455 peptide. CTL activity following restimulations was measured using a standard ⁵¹Cr release assay in which the lysis of ⁵¹Cr-labeled HLA-A2.1-transfected Jurkat target cells was measured in the presence (circle symbols) or absence of peptide (square symbols). The data points shown in Panels A–C represent a composite of lytic activity from a triplicate set of cultures. Panel A, splenic DC from ProGP (SD-9427) treated animals pulsed with the HBV Pol 455 peptide. Panel B, GM-CSF/IL-4 expanded DC pulsed with HBV Pol 455 peptide. Panel C, mock-pulsed DC from ProGP treated animals. Studies were performed at Epimmune Inc., San Diego, Calif.

Figure 5:
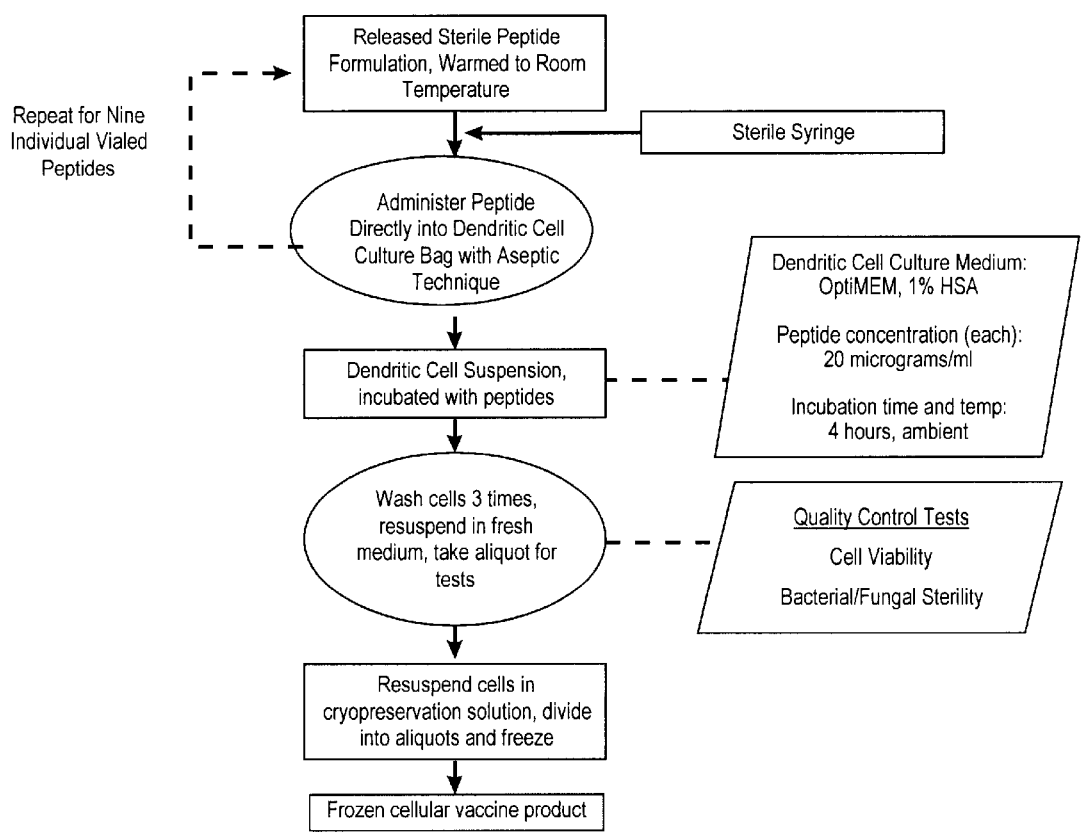

FIG. 5 presents a schematic of a dendritic cell pulsing and testing procedure.

IV. DETAILED DESCRIPTION

This invention provides a plurality of peptide epitopes that can be used to monitor an immune response to a tumor associated antigen or when one or more peptides are combined to create a cancer vaccine that stimulates the cellular arm of the immune system. In particular embodiments, vaccines mediate immune responses against tumors in individuals who bear an allele of the HLA-A2 supertype (see Table 5 for a listing of the members of the A2 and other supertypes); such vaccines will generally be referred to as A2 vaccines.

An A2 vaccine stimulates the immune system to recognize and kill tumor cells, leading to increased quality of life, and/or disease-free or overall survival rates for patients treated for cancer. In a preferred embodiment, an A2 vaccine will be administered to HLA-A2 or HLA-A2 supertype positive individuals with any cancer that expresses at least one of the TAAs from which vaccine epitopes were selected, such as breast, colon or lung cancer. Alternative embodiments of a vaccine are directed at patients who bear additional HLA alleles, or are not directed to A2 at all. Thereby, an A2 vaccine improves the standard of care for patients being treated for breast, colon or lung cancer.

The peptide epitopes and corresponding nucleic acid compositions of the present invention are useful for stimulating an immune response to TAAs by stimulating the production of CTL or HTL responses. The peptide epitopes, which are derived directly or indirectly from native TAA protein amino acid sequences, are able to bind to HLA molecules and stimulate an immune response to TAAs. The complete sequence of the TAAs proteins to be analyzed can be obtained from GenBank. Peptide epitopes and analogs thereof can also be readily determined from sequence information that may subsequently be discovered for heretofore unknown variants of TAAs, as will be clear from the disclosure provided below.

The peptide epitopes of the invention have been identified in a number of ways, as will be discussed below. Also discussed in greater detail is that analog peptides have been derived and the binding activity for HLA molecules modulated by modifying specific amino acid residues to create peptide analogs exhibiting altered immunogenicity. Further, the present invention provides compositions and combinations of compositions that enable epitope-based vaccines that are capable of interacting with HLA molecules encoded by various genetic alleles to provide broader population coverage than prior vaccines.

IV.A. Definitions

The invention can be better understood with reference to the following definitions:

Throughout this disclosure, "binding data" results are often expressed in terms of "IC$_{50}$'s." IC$_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. Assays for determining binding are described in detail, e.g., in PCT publications WO 94/20127 and WO 94/03205. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand. Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermnediate, weak, or negative binder is generally based on its $IC_{50}$, relative to the $IC_{50}$ of a standard peptide. Binding may also be determined using other assay systems including those using: live cells (e.g., Ceppellini et al., *Nature* 339:392 (1989); Christnick et al., *Nature* 352:67 (1991); Busch et al., *Int. Immunol.* 2:443 (1990); Hill et al., *J. Immunol.* 147:189 (1991); del Guercio et al., *J. Immunol.* 154:685 (1995)), cell free systems using detergent lysates (e.g., Cerundolo et al.,*J. Immunol.* 21:2069 (1991)), immobilized purified MHC (e.g., Hill et al., *J. Immunol.* 152, 2890 (1994); Marshall et al., *J. Immunol.* 152:4946 (1994)), ELISA systems (e.g., Reay et al., *EMBO J.* 11:2829 (1992)), surface plasmon resonance (e.g., Khilko et al., *J. Biol. Chem.* 268:15425 (1993)); high flux soluble phase assays (Hammer et al.,*J. Exp. Med.* 180:2353 (1994)), and measurement of class I MHC stabilization or assembly (e.g., Ljunggren et al., *Nature* 346:476 (1990); Schumacher et al., *Cell* 62:563 (1990); Townsend et al., *Cell* 62:285 (1990); Parker et al., *J. Immunol.* 149:1896 (1992)).

A "computer" or "computer system" generally includes: a processor and related computer programs; at least one information storage/retrieval apparatus such as a hard drive, a disk drive or a tape drive; at least one input apparatus such as a keyboard, a mouse, a touch screen, or a microphone; and display structure, such as a screen or a printer. Additionally, the computer may include a communication channel in communication with a network. Such a computer may include more or less than what is listed above.

"Cross-reactive binding" indicates that a peptide is bound by more than one HLA molecule; a synonym is degenerate binding.

A "cryptic epitope" elicits a response by immunization with an isolated peptide, but the response is not cross-reactive in vitro when intact whole protein, which comprises the epitope, is used as an antigen.

The term "derived" when used to discuss an epitope is a synonym for "prepared." A derived epitope can be isolated from a natural source, or it can be synthesized in accordance with standard protocols in the art. Synthetic epitopes can comprise artificial amino acids "amino acid mimetics," such as D isomers of natural occurring L amino acids or non-natural amino acids such as cyclohexylalanine. A derived/prepared epitope can be an analog of a native epitope.

A "dominant epitope" is an epitope that induces an immune response upon immunization with a whole native antigen (see, e.g., Sercarz, et al., *Annu. Rev. Immunol.* 11:729–766, 1993). Such a response is cross-reactive in vitro with an isolated peptide epitope.

An "epitope" is the collective features of a molecule, such as primary, secondary and tertiary peptide structure, and charge, that together form a site recognized by an immunoglobulin, T cell receptor or HLA molecule. Alternatively, an epitope can be defined as a set of amino acid residues which is involved in recognition by a particular immunoglobulin, or in the context of T cells, those residues necessary for recognition by T cell receptor proteins and/or Major Histocompatibility Complex (MHC) receptors. Epitopes are present in nature, and can be isolated, purified or otherwise prepared/derived by humans. For example, epitopes can be prepared by isolation from a natural source, or they can be synthesized in accordance with standard protocols in the art. Synthetic epitopes can comprise artificial amino acids "amino acid mimetics," such as D isomers of natural occurring L amino acids or non-natural amino acids such as cyclohexylalanine. Throughout this disclosure, the terms epitope and peptide are often used interchangeably.

It is to be appreciated that protein or peptide molecules that comprise an epitope of the invention as well as additional amino acid(s) are still within the bounds of the invention. In certain embodiments, there is a limitation on the length of a peptide of the invention. The embodiment that is length-limited occurs when the protein/peptide comprising an epitope of the invention comprises a region (i.e., a contiguous series of amino acids) having 100% identity with a native sequence. In order to avoid the definition of epitope from reading, e.g., on whole natural molecules, there is a limitation on the length of any region that has 100% identity with a native peptide sequence. Thus, for a peptide comprising an epitope of the invention and a region with 100% identity with a native peptide sequence, the region with 100% identity to a native sequence generally has a length of: less than or equal to 600 amino acids, often less than or equal to 500 amino acids, often less than or equal to 400 amino acids, often less than or equal to 250 amino acids, often less than or equal to 100 amino acids, , often less than or equal to 85 amino acids, often less than or equal to 75 amino acids, often less than or equal to 65 amino acids, and often less than or equal to 50 amino acids. In certain embodiments, an "epitope" of the invention is comprised by a peptide having a region with less than 51 amino acids that has 100% identity to a native peptide sequence, in any increment down to 5 amino acids.

Accordingly, peptide or protein sequences longer than 600 amino acids are within the scope of the invention, so long as they do not comprise any contiguous sequence of more than 600 amino acids that have 100% identity with a native peptide sequence. For any peptide that has five contiguous residues or less that correspond to a native sequence, there is no limitation on the maximal length of that peptide in order to fall within the scope of the invention. It is presently preferred that a CTL epitope be less than 600 residues long in any increment down to eight amino acid residues.

"Human Leukocyte Antigen" or "HLA" is a human class I or class II Major Histocompatibility Complex (MHC) protein (see, e.g., Stites, et al., Immunology, $8^{TH}$ Ed., Lange Publishing, Los Altos, Calif. (1994).

An "HLA supertype or HLA family", as used herein, describes sets of HLA molecules grouped on the basis of shared peptide-binding specificities. HLA class I molecules that share somewhat similar binding affinity for peptides bearing certain amino acid motifs are grouped into such HLA supertypes. The terms HLA superfamily, HLA supertype family, HLA family, and HLA xx-like molecules (where "xx" denotes a particular HLA type), are synonyms.

As used herein, "high affinity" with respect to HLA class I molecules is defined as binding with an $IC_{50}$, or $K_D$ value, of 50 nM or less; "intermediate affinity" is binding with an IC50 or $K_D$ value of between about 50 and about 500 nM. "High affinity" with respect to binding to HLA class II molecules is defined as binding with an $IC_{50}$ or $K_D$ value of 100 nM or less; "intermediate affinity" is binding with an $IC_{50}$ or $K_D$ value of between about 100 and about 1000 nM.

An "$IC_{50}$" is the concentration of peptide in a binding assay at which 50% inhibition of binding of a reference peptide is observed. Given the conditions in which the assays are run (i.e., limiting HLA proteins and labeled peptide concentrations), these values approximate $K_D$ values.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

An "immunogenic peptide" or "peptide epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T lymphocyte (CTL) response, or a helper T lymphocyte (HTL) response, to the peptide.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. In general, an isolated epitope does not have attached thereto additional amino acids that result in a sequence that has 100% identity with a native sequence. The native sequence can be a sequence such as a tumor-associated antigen from which the epitope is derived.

"Major Histocompatibility Complex" or "MHC" is a cluster of genes that plays a role in control of the cellular interactions responsible for physiologic immune responses. In humans, the MHC complex is also known as the human leukocyte antigen (HLA) complex. For a detailed description of the MHC and HLA complexes, see, Paul, FUNDAMENTAL IMMUNOLOGY, $3^{RD}$ ED., Raven Press, New York (1993).

The term "motif" refers to a pattern of residues in an amino acid sequence of defined length, usually a peptide of from about 8 to about 13 amino acids for a class I HLA motif and from about 6 to about 25 amino acids for a class II HLA motif, which is recognized by a particular HLA molecule. Motifs are typically different for each HLA protein encoded by a given human HLA allele. These motifs often differ in their pattern of the primary and secondary anchor residues.

A "native" sequence refers to a sequence found in nature.

A "negative binding residue" or "deleterious residue" is an amino acid which, if present at certain positions (typically not primary anchor positions) in a peptide epitope, results in decreased binding affinity of the peptide for the peptide's corresponding HLA molecule.

The term "peptide" is used interchangeably with "oligopeptide" in the present specification to designate a series of residues, typically L-amino acids, connected one to the other, typically by peptide bonds between the α-amino and carboxyl groups of adjacent amino acids.

A "PanDR binding peptide" or "PADRE®" molecule (Epimmune, San Diego, Calif.) is a member of a family of molecules that binds more than one HLA class II DR molecule. The pattern that defines the PADRE® family of molecules can be referred to as an HLA Class II supermotif. A PADRE® molecule binds to HLA-DR molecules and stimulates in vitro and in vivo human helper T lymphocyte (HTL) responses. For a further definition of the PADRE® family, see copending application U.S. Ser. No. 09/310,462, filed May 12, 1999, now abandoned; PCT publication WO 95/07707, and, U.S. Pat. No. 5,736,142 issued Apr. 7, 1998.

"Pharmaceutically acceptable" refers to a generally non-toxic, inert, and/or physiologically compatible composition.

A "pharmaceutical excipient" comprises a material such as an adjuvant, a carrier, pH-adjusting and buffering agents, tonicity adjusting agents, wetting agents, preservatives, and the like.

A "primary anchor residue" is an amino acid at a specific position along a peptide sequence which is understood to provide a contact point between the immunogenic peptide and the HLA molecule. One, two or three, primary anchor residues within a peptide of defined length generally defines a "motif" for an immunogenic peptide. These residues are understood to fit in close contact with peptide binding grooves of an HLA molecule, with their side chains buried in specific pockets of the binding grooves themselves. In one embodiment of an HLA class I motif, the primary anchor residues are located at position 2 (from the amino terminal position) and at the carboxyl terminal position of a peptide epitope in accordance with the invention. The primary anchor positions for each motif and supermotif of HLA Class I and HLA Class II are set forth in Table 2, Table 3 and Table 4. For example, analog peptides can be created by altering the presence or absence of particular residues in these anchor positions. Such analogs are used to modulate the binding affinity of a peptide comprising a particular motif or supermotif.

"Promiscuous recognition" by a TCR is where a distinct peptide is recognized by the various T cell clones in the context of various HLA molecules. Promiscuous binding by an HLA molecule is synonymous with cross-reactive binding.

A "protective immune response" or "therapeutic immune response" refers to a CTL and/or an HTL response to an antigen derived from an pathogenic antigen (e.g., an antigen from an infectious agent or a tumor antigen), which in some way prevents or at least partially arrests disease symptoms, side effects or progression. The immune response may also include an antibody response which has been facilitated by the stimulation of helper T cells.

The term "residue" refers to an amino acid or amino acid mimetic incorporated into a peptide or protein by an amide bond or amide bond mimetic.

A "secondary anchor residue" is an amino acid at a position other than a primary anchor position in a peptide which may influence peptide binding. A secondary anchor residue occurs at a significantly higher frequency amongst HLA-bound peptides than would be expected by random distribution of amino acids at a given position. A secondary anchor residue can be identified as a residue which is present at a higher frequency among high or intermediate affinity binding peptides, or a residue otherwise associated with high or intermediate affinity binding. The secondary anchor residues are said to occur at "secondary anchor positions." For example, analog peptides can be created by altering the presence or absence of particular residues in these secondary anchor positions. Such analogs are used to finely modulate the binding affinity of a peptide comprising a particular motif or supermotif. The terminology "fixed peptide" is sometimes used to refer to an analog peptide.

A "subdominant epitope" is an epitope which evokes little or no response upon immunization with whole antigens which comprise the epitope, but for which a response can be obtained by immunization with an isolated peptide, and this response (unlike the case of cryptic epitopes) is detected when whole protein is used to recall the response in vitro or in vivo.

A "supermotif" is a peptide binding specificity shared by HLA molecules encoded by two or more HLA alleles. Preferably, a supermotif-bearing peptide is recognized with high or intermediate affinity (as defined herein) by two or more HLA antigens.

"Synthetic peptide" refers to a peptide that is not naturally occurring, but is man-made using such methods as chemical synthesis or recombinant DNA technology.

As used herein, a "vaccine" is a composition that contains one or more peptides of the invention, see, e.g., Table 6, Table 9 and Table 10. There are numerous embodiments of vaccines in accordance with the invention, such as by a cocktail of one or more peptides; one or more peptides of the invention comprised by a polyepitopic peptide; or nucleic acids that encode such peptides or polypeptides, e.g., a minigene that encodes a polyepitopic peptide. The peptides or polypeptides can optionally be modified, such as by lipidation, addition of targeting or other sequences. HLA class I-binding peptides of the invention can be linked to HLA class II-binding peptides, to facilitate activation of both cytotoxic T lymphocytes and helper T lymphocytes. Vaccines can comprise peptide pulsed antigen presenting cells, e.g., dendritic cells.

The nomenclature used to describe peptide/protein compounds follows the conventional practice wherein the amino group is presented to the left (the N-terminus) and the carboxyl group to the right (the C-terminus) of each amino acid residue. When amino acid residue positions are referred to in a peptide epitope they are numbered in an amino to carboxyl direction with position one being the position closest to the amino terminal end of the epitope, or the peptide or protein of which it may be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. However, when three letter symbols or full names are used without capitals, they may refer to L amino acids. Glycine has no asymmetric carbon atom and is simply referred to as "Gly" or "G". Standard symbols/nomenclature for the L amino acids are shown below.

| Single Letter Symbol | Three Letter Symbol | Amino Acids |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Acronyms used herein are as follows:

| | |
|---|---|
| APC: | Antigen presenting cell |
| CD3: | Pan T cell marker |
| CD4: | Helper T lymphocyte marker |
| CD8: | Cytotoxic T lymphocyte marker |
| CEA: | Carcinoembryonic antigen |
| CTL: | Cytotoxic T lymphocyte |
| DC: | Dendritic cells. DC functioned as potent antigen presenting cells by stimulating cytokine release from CTL lines that were specific for a model peptide derived from hepatitis B virus. In vivo experiments using DC pulsed ex vivo with an HBV peptide epitope have stimulated CTL immune responses in vivo following delivery to naive mice. |
| DLT: | Dose-limiting toxicity, an adverse event related to therapy. |
| DMSO: | Dimethylsulfoxide |
| ELISA: | Enzyme-linked immunosorbant assay |
| E:T: | Effector:Target ratio |
| G-CSF: | Granulocyte colony-stimulating factor |
| GM-CSF: | Granulocyte-macrophage (monocyte)-colony stimulating factor |
| HBV: | Hepatitis B virus |
| HER2/neu: | A tumor associated antigen; c-erbB-2 is a synonym. |
| HLA: | Human leukocyte antigen |
| HLA-DR: | Human leukocyte antigen class II |
| HPLC: | High Performance Liquid Chromatography |
| HTC: | Helper T Cell |
| HTL: | Helper T Lymphocyte. A synonym for HTC. |
| ID: | Identity |
| IFNγ: | Interferon gamma |
| IL-4: | Interleukin-4 |
| IV: | Intravenous |
| $LU_{30\%}$: | Cytotoxic activity for $10^6$ effector cells required to achieve 30% lysis of a target cell population, at a 100:1 (E:T) ratio. |
| MAb: | Monoclonal antibody |
| MAGE: | Melanoma antigen |
| MLR: | Mixed lymphocyte reaction |
| MNC: | Mononuclear cells |
| PB: | Peripheral blood |
| PBMC: | Peripheral blood mononuclear cell |
| ProGP ™: | Progenipoietin ™ (Searle, St. Louis, MO), a chimeric flt3/G-CSF receptor agonist. |
| SC: | Subcutaneous |
| S.E.M.: | Standard error of the mean |
| QD: | Once a day dosing |
| TAA: | Tumor Associated Antigen |
| TNF: | Tumor necrosis factor |
| WBC: | White blood cells |

IV.B. Stimulation of CTL and HTL Responses

The mechanism by which T cells recognize antigens has been elucidated during the past ten years. In accordance with this understanding of the immune system, we have developed efficacious peptide epitope compositions that induce a therapeutic or prophylactic immune response to TAA, when administered via various art-accepted modalities. These peptides can also be used diagnostically, e.g., to evaluate the immune response to an antigen. Moreover, by use of supermotif-bearing peptides, or by use of combinations of peptides in accordance with the principles disclosed herein, responses can be achieved in significant percentages of a non-genetically biased worldwide population. For an understanding of the value and efficacy of the claimed compositions, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317:359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Tables 2, 3, and 4. Of particular interest in the present application are the A2 supermotif and the allele-specific A2.1 motif, due to the substantial population coverage they provide.

Furthermore, x-ray crystallographic analyses of HLA-peptide complexes have revealed pockets within the peptide binding cleft of HLA molecules which accommodate, often on an allele-specific basis, residues borne by peptide ligands; these residues in turn determine the HLA binding capacity of the peptides in which they are present. (See, e.g., Madden, D. R. *Annu. Rev. Immunol.* 13:587 (1995); Smith, et al., *Immunity* 4:203, 1996; Fremont et al., *Immunity* 8:305 (1998); Stem et al., *Structure* 2:245 (1994); Jones, E. Y. *Curr. Opin. Immunol.* 9:75 (1997); Brown, J. H. et al., *Nature* 364:33 (1993); Guo, H. C. et al., *Proc. Natl. Acad. Sci. USA* 90:8053 (1993); Guo, H. C. et al., *Nature* 360:364 (1992); Silver, M. L. et al., *Nature* 360:367 (1992); Matsumura, M. et al., *Science* 257:927 (1992); Madden et al., *Cell* 70:1035 (1992); Fremont, D. H. et al., *Science* 257:919 (1992); Saper, M. A., Bjorkman, P. J. and Wiley, D. C., *J. Mol. Biol.* 219:277 (1991).)

Accordingly, the definition of class I and class II allele-specific HLA binding motifs, or class I or class II supermotifs allows identification of regions within a protein that have the predicted ability to bind particular HLA antigen(s).

Moreover, the present inventors have found that the correlation of binding affinity with immunogenicity, which is disclosed herein, is an important factor to be considered when evaluating candidate peptides. Thus, by a combination of motif searches of antigenic sequences, and by HLA-peptide binding assays, epitope-based vaccines have been identified. As appreciated by one in the art, after determining their binding affinity, additional work can be performed to select, amongst these vaccine peptides, e.g., epitopes can be selected having optional characteristics in terms of population coverage, antigenicity, and immunogenicity, etc.

Various strategies can be utilized to evaluate immunogenicity, including:

1) Evaluation of primary T cell cultures from normal individuals (see, e.g., Wentworth, P. A. et al., *Mol. Immunol.* 32:603 (1995); Celis, E. et al., *Proc. Natl. Acad. Sci. USA* 91:2105 (1994); Tsai, V. et al., *J. Immunol.* 158:1796 (1997); Kawashima, I. et al., *Human Immunol.* 59:1 (1998)). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a $^{51}$Cr-release assay involving peptide sensitized target cells, and/or target cells that generate antigen endogenously.

2) Immunization of HLA transgenic mice (see, e.g., Wentworth, P. A. et al., *J. Immunol.* 26:97 (1996); Wentworth, P. A. et al., *Int. Immunol.* 8:651 (1996); Alexander, J. et al., *J. Immunol.* 159:4753 (1997)); in this method, peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from individuals exposed to the disease, such as immune individuals who were effectively treated and recovered from disease, and/or from actively ill patients (see, e.g., Rehermann, B. et al., *J. Exp. Med.* 181:1047 (1995); Doolan, D. L. et al., *Immunity* 7:97 (1997); Bertoni, R. et al., *J. Clin. Invest.* 100:503 (1997); Threlkeld, S. C. et al., *J. Immunol.* 159:1648 (1997); Diepolder, H. M. et al., *J. Virol.* 71:6011 (1997)). In applying this strategy, recall responses are detected by culturing PBL from subjects in vitro for 1–2 weeks in the presence of a test peptide plus antigen presenting cells (APC) to allow activation of "memory" T cells, as compared to "naive" T cells. At the end of the culture period, T cell activity is detected using assays for T cell activity including $^{51}$Cr release involving peptide-sensitized targets, T cell proliferation, or lymphokine release.

The following describes the peptide epitopes and corresponding nucleic acids of the invention in more detail.

IV.C. Binding Affinity of Peptide Epitopes for HLA Molecules

As indicated herein, the large degree of HLA polymorphism is an important factor to be taken into account with the epitope-based approach to vaccine development. To address this factor, epitope selection encompassing identification of peptides capable of binding at high or intermediate affinity to multiple HLA molecules is preferably utilized, most preferably these epitopes bind at high or intermediate affinity to two or more allele-specific HLA molecules.

CTL-inducing peptides of interest for vaccine compositions preferably include those that have an $IC_{50}$ or binding affinity value for a class I HLA molecule(s) of 500 nM or better (i.e., the value is $\leq$500 nM). HTL-inducing peptides preferably include those that have an $IC_{50}$ or binding affinity value for class II HLA molecules of 1000 nM or better, (i.e., the value is $\leq$1,000 nM). For example, peptide binding is assessed by testing the capacity of a candidate peptide to bind to a purified HLA molecule in vitro. Peptides exhibiting high or intermediate affinity are then considered for further analysis. Selected peptides are generally tested on other members of the supertype family. In preferred embodiments, peptides that exhibit cross-reactive binding are then used in cellular screening analyses or vaccines.

The relationship between binding affinity for HLA class I molecules and immunogenicity of discrete peptide epitopes on bound antigens was determined for the first time in the art by the present inventors. As disclosed in greater detail herein, higher HLA binding affinity is correlated with greater immunogenicity.

Greater immunogenicity can be manifested in several different ways. Immunogenicity corresponds to whether an immune response is elicited at all, and to the vigor of any particular response, as well as to the extent of a population in which a response is elicited. For example, a peptide might elicit an immune response in a diverse array of the population, yet in no instance produce a vigorous response. In accordance with these principles, close to 90% of high binding peptides have been found to elicit a response and thus be "immunogenic," as contrasted with about 50% of the peptides that bind with intermediate affinity. (See, e.g., Schaeffer et al. PNAS (1988)) Moreover, not only did peptides with higher binding affinity have an enhanced probability of generating an immune response, the generated response tended to be more vigorous than the response seen with weaker binding peptides. As a result, less peptide is required to elicit a similar biological effect if a high affinity binding peptide is used rather than a lower affinity one. Thus, in preferred embodiments of the invention, high affinity binding epitopes are used.

The correlation between binding affinity and immunogenicity was analyzed by the present inventors by two different experimental approaches (see, e.g., Sette, et al., *J. Immunol.* 153:5586–5592 (1994)). In the first approach, the immunogenicity of potential epitopes ranging in HLA binding affinity over a 10,000-fold range was analyzed in HLA-A*0201 transgenic mice. In the second approach, the antigenicity of approximately 100 different hepatitis B virus (HBV)-derived potential epitopes, all carrying A*0201 binding motifs, was assessed by using PBL from acute hepatitis patients. Pursuant to these approaches, it was determined that an affinity threshold value of approximately 500 nM (preferably 50 nM or less) determines the capacity of a peptide epitope to elicit a CTL response. These data are true for class I binding affinity measurements for naturally processed peptides and for synthesized T cell epitopes. These data also indicate the important role of determinant selection in the shaping of T cell responses (see, e.g., Schaeffer et al. *Proc. Natl. Acad. Sci. USA* 86:4649–4653 (1989)).

An affinity threshold associated with immunogenicity in the context of HLA class II (i.e., HLA DR) molecules has also been delineated (see, e.g., Southwood et al. *J. Immunology* 160:3363–3373 (1998), and co-pending U.S. Ser. No. 09/009,953 filed Jan. 21, 1998, now U.S. Pat. No. 6,413,517). In order to define a biologically significant threshold of HLA class II binding affinity, a database of the binding affinities of 32 DR-restricted epitopes for their restricting element (i.e., the HLA molecule that binds the epitope) was compiled. In approximately half of the cases (15 of 32 epitopes), DR restriction was associated with high binding affinities, i.e. binding affinity values of 100 nM or less. In the other half of the cases (16 of 32), DR restriction was associated with intermediate affinity (binding affinity values in the 100–1000 nM range). In only one of 32 cases was DR restriction associated with an $IC_{50}$ of 1000 nM or greater. Thus, 1000 nM is defined as an affinity threshold associated with immunogenicity in the context of DR molecules.

The binding affinity of peptides for HLA molecules can be determined as described in Example 1, below.

IV.D. Peptide Epitope Binding Motifs and Supermotifs

Through the study of single amino acid substituted antigen analogs and the sequencing of endogenously bound, naturally processed peptides, critical residues required for allele-specific binding to HLA molecules have been identified. The presence of these residues in a peptide correlates with both the probability of binding and with binding affinity for HLA molecules.

The identification of motifs and/or supermotifs that correlate with high and intermediate affinity binding is important when identifying immunogenic peptide epitopes for the inclusion in a vaccine. Kast et al. (*J. Immunol.* 152:3904–3912 (1994)) have shown that motif-bearing peptides account for 90% of the epitopes that bind to allele-specific HLA class I molecules. In the Kast study, all possible 9 amino acid long peptides, each overlapping by eight amino acids, which cover the entire sequence of the E6 and E7 proteins of human papillomavirus type 16 were generated, which produced 240 peptides. All 240 peptides were evaluated for binding to five allele-specific HLA molecules that are expressed at high frequency among different ethnic groups. This unbiased set of peptides allowed an evaluation of the predictive values of HLA class I motifs. From the set of 240 peptides, 22 peptides were identified that bound to an allele-specific HLA molecule with high or intermediate affinity. Of these 22 peptides, 20 (i.e. 91%) were motif-bearing. Thus, this study demonstrated the value of motifs for identification of peptide epitopes to be included in a vaccine.

Accordingly, the use of motif-based identification techniques identifies approximately 90% of all potential epitopes in a target protein sequence. Without the disclosed motif analysis, the ability to practically identify immunogenic peptide(s) for use in diagnostics or therapeutics is seriously impaired.

Vaccines of the present invention may also comprise epitopes that bind to MHC class II DR molecules. A greater degree of heterogeneity in both size and binding frame position of the motif, relative to the N and C termini of the peptide, exists for class II peptide ligands. This increased heterogeneity of HLA class II peptide ligands is due to the structure of the binding groove of the HLA class II molecule which, unlike its class I counterpart, is less physically constricted at both ends. Crystallographic analysis of HLA class II DRB*0101-peptide complexes to identify the residues associated with major binding energy identified those residues complexed with complementary pockets on the DRBI*0101 molecules. An important anchor residue engages the deepest hydrophobic pocket (see, e.g., Madden, D. R. *Ann. Rev. Immunol.* 13:587 (1995)) and is referred to as position 1 (P1). P1 may represent the N-terminal residue of a class II binding peptide epitope, but more typically is flanked towards the N-terminus by one or more residues. Other studies have also pointed to an important role for the peptide residue in the sixth position towards the C-terminus, relative to P1, for binding to various DR molecules. See, e.g., U.S. Pat. No. 5,736,142, and a co-pending application entitled Alteration Of Immune Responses Using Pan DR Binding Peptides, U.S. Ser. No. 09/310,462, filed May 12 1999, now abandoned.

Thus, a large fraction of HLA class I and class II molecules can be classified into a relatively few supertypes, each respective supertype characterized by largely overlapping peptide binding repertoires, and consensus structures of the main peptide binding pockets. Thus, peptides of the present invention are preferably identified by any one of several HLA-specific amino acid motifs (see, e.g., Tables 2–4), or if the presence of the motif corresponds to the ability to bind several allele-specific HLA antigens, a supermotif (again see, e.g., Tables 2–4).

The primary anchor residues of the HLA class I peptide epitope supermotifs and motifs are summarized in Table 2. The HLA class I motifs set out in Table 2(a) are particularly relevant to the invention claimed here. Primary and secondary anchor positions for HLA Class I are summarized in Table 3. Allele-specific HLA molecules that are comprised by the various HLA class I supertypes are listed in Table 5. In some cases, patterns of amino acid residues are present in both a motif and a supermotif. The relationship of a particular motif and any related supermotif is indicated in the description of the individual motifs.

Thus, the peptide motifs and supermotifs described below, and summarized in Tables 2–4, provide guidance for the identification and use of peptide epitopes in accordance with the invention.

IV.D.1. HLA-A2 Supermotif

Primary anchor specificities for allele-specific HLA-A2.1 molecules (see, e.g., Falk et al., *Nature* 351:290–296 (1991); Hunt et al., *Science* 255:1261–1263 (1992); Parker et al., *J. Immunol.* 149:3580–3587 (1992); Ruppert et al., *Cell* 74:929–937 (1993)) and cross-reactive binding among HLA-A2 and -A28 molecules have been described. (See, e.g., Fruci et al., *Human Immunol.* 38:187–192 (1993); Tanigaki et al., *Human Immunol.* 39:155–162 (1994); del Guercio et al., *J. Immunol.* 154:685–693 (1995); Kast et al., *J. Immunol.* 152:3904–3912 (1994) for reviews of relevant data.) These primary anchor residues define the HLA-A2 supermotif; which when present in peptide ligands corresponds to the ability to bind several different HLA-A2 and -A28 molecules. The HLA-A2 supermotif comprises peptide ligands with L, I, V, M, A, T, or Q as a primary anchor residue at position 2 and L, I, V, M, A, or T as a primary anchor residue at the C-terminal position of the epitope.

The corresponding family of HLA molecules (i.e., the HLA-A2 supertype that binds these peptides) is comprised of at least: A*0201, A*0202, A*0203, A*0204, A*0205, A*0206, A*0207, A*0209, A*0214, A*6802, and A*6901. Other allele-specific HLA molecules predicted to be members of the A2 superfamily are shown in Table 5. As explained in detail below, binding to each of the individual allele-specific HLA molecules can be modulated by substitutions at the primary anchor and/or secondary anchor positions, preferably choosing respective residues specified for the supermotif.

IV.D.2. HLA-A*0201 Motif

An HLA-A2*0201 motif was determined to be characterized by the presence in peptide ligands of L or M as a primary anchor residue in position 2, and L or V as a primary anchor residue at the C-terminal position of a 9-residue peptide (see, e.g., Falk et al., *Nature* 351:290–296 (1991)) and was further found to comprise an I at position 2 and I or A at the C-terninal position of a nine amino acid peptide (see, e.g., Hunt et al., *Science* 255:1261–1263, Mar. 6, 1992; Parker et al., *J. Immunol.* 149:3580–3587 (1992)). The A*0201 allele-specific motif has also been defined by the present inventors to additionally comprise V, A, T, or Q as a primary anchor residue at position 2, and M or T as a primary anchor residue at the C-terminal position of the epitope (see, e.g., Kast et al., *J. Immunol.* 152:3904–3912, 1994).

Thus, the HLA-A*0201 motif comprises peptide ligands with L, I, V, M, A, T, or Q as primary anchor residues at position 2 and L, I, V, M, A, or T as a primary anchor residue at the C-terminal position of the epitope. For this motif-supermotif relationship the preferred and less preferred/ tolerated residues that characterize the primary anchor positions of the HLA-A*0201 motif are identical to the residues describing the A2 supermotif. (For reviews of relevant data, see, e.g., del Guercio et al., *J. Immunol.* 154:685–693, 1995; Ruppert et al., *Cell* 74:929–937, 1993; Sidney et al., *Immunol. Today* 17:261–266, 1996; Sette and Sidney, *Curr. Opin. in Immunol.* 10:478–482, 1998). Secondary anchor residues that characterize the A*0201 motif have additionally been defined (see, e.g., Ruppert et al., *Cell* 74:929–937, 1993). These secondary anchors are shown in Table 3. Peptide binding to HLA-A*0201 molecules can be modulated by substitutions at primary and/or secondary anchor positions, preferably choosing respective residues specified for the motif.

IV.D.3. Motifs Indicative of Class II HTL Inducing Peptide Epitopes

The primary and secondary anchor residues of the HLA class II peptide epitope supermotifs and motifs are summarized in Table 4. Also see, U.S. Pat. No. 5,736,142, and a co-pending application entitled Alteration Of Immune Responses Using Pan DR Binding Peptides, U.S. Ser. No. 09/310,462, filed May 12, 1999, now abandoned.

IV.E. Enhancing Population Coverage of the Vaccine

As set forth in Tables 2 through 4, there are numerous additional supermotifs and motifs in addition to the A2 supermotif and the A2.1-allele specific motif that presently are a focus of the present application. By inclusion of one or more epitopes from other motifs or supermotifs, enhanced population coverage for major global ethnicities can be obtained.

IV.F. Immune Response-Stimulating Peptide Analogs

In general, CTL and HTL responses are not directed against all possible epitopes. Rather, they are restricted to a few "immunodominant" determinants (Zinkernagel, et al., *Adv. Immunol.* 27:5159, 1979; Bennink, et al., *J. Exp. Med.* 168:19351939, 1988; Rawle, et al., *J. Immunol.* 146:3977–3984, 1991). It has been recognized that immunodominance (Benacerraf, et al., *Science* 175:273–279, 1972) could be explained by either the ability of a given epitope to selectively bind a particular HLA protein (determinant selection theory) (Vitiello, et al., *J. Immunol.* 131:1635, 1983); Rosenthal, et al., *Nature* 267:156–158, 1977), or to be selectively recognized by the existing TCR (T cell receptor) specificities (repertoire theory) (Klein, J., Immunology, The Science of Selfnonself Discrimination, John Wiley & Sons, New York, pp. 270–310, 1982). It has been demonstrated that additional factors, mostly linked to processing events, can also play a key role in dictating, beyond strict immnunogenicity, which of the many potential determinants will be presented as immunodominant (Sercarz, et al., *Annu. Rev. Immunol.* 11:729–766, 1993).

The concept of dominance and subdominance is relevant to immunotherapy of both infectious diseases and malignancies. For example, in the course of chronic viral disease, recruitment of subdominant epitopes can be important for successful clearance of the infection, especially if dominant CTL or HTL specificities have been inactivated by functional tolerance, suppression, mutation of viruses and other mechanisms (Franco, et al., *Curr. Opin. Immunol.* 7:524–531, 1995). In the case of cancer and tumor antigens, CTLs recognizing at least some of the highest binding affinity peptides might be functionally inactivated. Lower binding affinity peptides are preferentially recognized at these times, and may therefore be preferred in therapeutic or prophylactic anti-cancer vaccines.

In particular, it has been noted that a significant number of epitopes derived from known non-viral tumor associated antigens (TAA) bind HLA class I with intermediate affinity ($IC_{50}$ in the 50–500 nM range) rather than at high affinity ($IC_{50}$ of less than 50 nM).

For example, it has been found that 8 of 15 known TAA peptides recognized by tumor infiltrating lymphocytes (TIL) or CTL bound in the 50–500 nM range. (These data are in contrast with estimates that 90% of known viral antigens were bound by HLA class I molecules with $IC_{50}$ of 50 mM or less, while only approximately 10% bound in the 50–500 nM range (Sette, et al., *J. Immunol.*, 153:558–5592, 1994). In the cancer setting this phenomenon is probably due to elimination or functional inhibition of the CTL recognizing several of the highest binding peptides, presumably because of T cell tolerization events.

Without intending to be bound by theory, it is believed that because T cells to dominant epitopes may have been clonally deleted, and selecting subdominant epitopes may allow existing T cells to be recruited, which will then lead to a therapeutic or prophylactic response. However, the binding of HLA molecules to subdominant epitopes is often less vigorous than to dominant ones.

Accordingly, there is a need to be able to modulate the binding affinity of particular immunogenic epitopes for one or more HLA molecules, to thereby modulate the immune response elicited by the peptide, for example to prepare analog peptides which elicit a more vigorous response. This ability to modulate both binding affinity and the resulting immune response in accordance with the present invention greatly enhances the usefulness of peptide epitope-based vaccines and therapeutic agents.

Although peptides with suitable cross-reactivity among all alleles of a superfamily are identified by the screening procedures described above, cross-reactivity is not always as complete as possible, and in certain cases procedures to increase cross-reactivity of peptides can be useful; moreover, such procedures can also be used to modify other properties of the peptides such as binding affinity or peptide stability. Having established the general rules that govern cross-reactivity of peptides for HLA alleles within a given motif or supermotif, modification (i.e., analoging) of the structure of peptides of particular interest in order to achieve broader (or otherwise modified) HLA binding capacity can be performed. More specifically, peptides that exhibit the broadest cross-reactivity patterns, can be produced in accordance with the teachings herein. The present concepts related to analog generation are set forth in greater detail in co-pending U.S. Ser. No. 09/226,775 filed Jan. 6, 1999.

In brief, the analoging strategy utilizes the motifs or supermotifs that correlate with binding to certain HLA molecules. Analog peptides can be created by substituting amino acid residues at primary anchor, secondary anchor, or at primary and secondary anchor positions. Generally, analogs are made for peptides that already bear a motif or supermotif. As noted herein, preferred primary and secondary anchor residues of supermotifs and motifs for HLA class I and HLA class II binding peptides are shown in Tables 3 and 4, respectively. For a number of the motifs or supermotifs in accordance with the invention, residues are defined which are deleterious to binding to allele-specific HLA molecules or members of HLA supertypes that bind the respective motif or supermotif (Tables 3 and 4). Accordingly, removal of such residues that are detrimental to binding can be performed in accordance with the present invention. For example, in the case of the A3 supertype, when all peptides that have such deleterious residues are removed from the population of peptides used in the analysis, the incidence of cross-reactivity increased from 22% to 37% (see, e.g., Sidney, J. et al., *Hu. Immunol.* 45:79, 1996).

Thus, one strategy to improve the cross-reactivity of peptides within a given supermotif is simply to delete one or more of the deleterious residues present within a peptide and substitute a small "neutral" residue such as Ala (that may not influence T cell recognition of the peptide). An enhanced likelihood of cross-reactivity is expected if, together with elimination of detrimental residues within a peptide, "preferred" residues associated with high affinity binding to an allele-specific HLA molecule or to multiple HLA molecules within a superfamily are inserted.

To ensure that an analog peptide, when used as a vaccine, actually elicits a CTL response to the native epitope in vivo (or, in the case of class II epitopes, elicits helper T cells that cross-react with the wild type peptides), the analog peptide may be used to induce T cells in vitro from individuals of the appropriate HLA allele. Thereafter, the immunized cells' capacity to lyse wild type peptide sensitized target cells is evaluated. Alternatively, evaluation of the cells' activity can be evaluated by monitoring IFN release. Each of these cell monitoring strategies evaluate the recognition of the APC by the CTL. It will be desirable to use as antigen presenting cells, cells that have been either infected, or transfected with the appropriate genes, or, (generally only for class II epitopes, due to the different peptide processing pathway for HLA class II), cells that have been pulsed with whole protein antigens, to establish whether endogenously produced antigen is also recognized by the T cells induced by the analog peptide. It is to be noted that peptide/protein-pulsed dendritic cells can be used to present whole protein antigens for both HLA class I and class II.

Another embodiment of the invention is to create analogs of weak binding peptides, to thereby ensure adequate numbers of cellular binders. Class I binding peptides exhibiting binding affinities of 500–5000 nM, and carrying an acceptable but suboptimal primary anchor residue at one or both positions can be "fixed" by substituting preferred anchor residues in accordance with the respective supertype. The analog peptides can then be tested for binding and/or cross-binding capacity.

Another embodiment of the invention is to create analogs of peptides that are already cross-reactive binders and are vaccine candidates, but which bind weakly to one or more alleles of a supertype. If the cross-reactive binder carries a suboptimal residue (less preferred or deleterious) at a primary or secondary anchor position, the peptide can be analoged by substituting out a deleterious residue and replacing it with a preferred or less preferred one, or by substituting out a less preferred reside and replacing it with a preferred one. The analog peptide can then be tested for cross-binding capacity.

Another embodiment for generating effective peptide analogs involves the substitution of residues that have an adverse impact on peptide stability or solubility in, e.g., a liquid environmernt. This substitution may occur at any position of the peptide epitope. For example, a cysteine (C) can be substituted out in favor of α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances (see, e.g., the review by Sette et al., In: *Persistent Viral Infections,* Eds. R. Ahmed and I. Chen, John Wiley & Sons, England, 1999). Substitution of cysteine with α-amino butyric acid may occur at any residue of a peptide epitope, i.e. at either anchor or non-anchor positions.

Moreover, it has been shown that in sets of A*0201 motif-bearing peptides containing at least one preferred secondary anchor residue while avoiding the presence of any deleterious secondary anchor residues, 69% of the peptides will bind A*0201 with an $IC_{50}$ less than 500 nM (Ruppert, J. et al. *Cell* 74:929, 1993). The determination of what was a preferred or deleterious residue in Ruppert can be used to generate algorithms (see, e.g., 22). Such algorithms are flexible in that cut-off scores may be adjusted to select sets of peptides with greater or lower predicted binding properties, as desired.

In accordance with the procedures described herein, tumor associated antigen peptide epitopes and analogs thereof that were found to bind HLA-A2 allele-specific molecules and to members of the HLA-A2 supertype have been identified.

Furthermore, additional amino acids can be added to the termini of a peptide to provide for ease of linking peptides one to another, for coupling to a carrier support or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide, particularly class I peptides. It is to be noted that modification at the carboxyl terminus of a CTL epitope may, in some cases, alter binding characteristics of the peptide. In addition, the peptide or oligopeptide sequences can differ from the natural sequence by being modified by terminal-$NH_2$ acylation, e.g., by alkanoyl ($C_1$–$C_{20}$) or thioglycolyl acetylation, terminal-carboxyl amidation, e.g., ammonia, methylamine, etc. In some instances these modificationss may provide sites for linking to a support or other molecule.

IV.G. Preparation of Peptide Epitopes

Peptides in accordance with the invention can be prepared synthetically, by recombinant DNA technology or chemical synthesis, or from natural sources such as native tumors or pathogenic organisms. Peptide epitopes may be synthesized individually or as polyepitopic peptides. Although the peptide will preferably be substantially free of other naturally occurring host cell proteins and fragments thereof, in some embodiments the peptides may be synthetically conjugated to native fragments or particles.

The peptides in accordance with the invention can be a variety of lengths, and either in their neutral (uncharged) forms or in forms which are salts. The peptides in accordance with the invention can contain modifications such as glycosylation, side chain oxidation, or phosphorylation, generally subject to the condition that modifications do not destroy the biological activity of the peptides.

The peptides of the invention can be prepared in a wide variety of ways. For the preferred relatively short size, the peptides can be synthesized in solution or on a solid support in accordance with conventional techniques. Various automatic synthesizers are commercially available and can be used in accordance with known protocols. (See, for example, Stewart & Young, Solid Phase Peptide Synthesis, 2d. Ed., Pierce Chemical Co., 1984). Further, individual peptide epitopes can be joined using chemical ligation to produce larger peptides that are still within the bounds of the invention.

Alternatively, recombinant DNA technology can be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., Molecular Cloning, a Laboratory Manual, Cold Spring Harbor Press, Cold Spring Harbor, N.Y. (1989). Thus, recombinant polypeptides, which comprise one or more peptide sequences of the invention, can be used to present the appropriate T cell epitope.

The nucleotide coding, sequence for peptide epitopes of the preferred lengths contemplated herein can be synthesized by chemical techniques, for example, the phosphotriester method of Matteucci, et al., *J. Am. Chem. Soc.* 103:3185 (1981). Peptide analogs can be made simply by substituting the appropriate and desired nucleic acid base(s) for those that encode the native peptide sequence; exemplary nucleic acid substitutions are those that encode an amino acid defined by the motifs/supermotifs herein. The coding sequence can then be provided with appropriate linkers and ligated into expression vectors commonly available in the art, and the vectors used to transform suitable hosts to produce the desire fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast, insect or mammalian cell hosts may also be used, employing suitable vectors and control sequences.

It is generally preferable that the peptide epitope be as small as possible while still maintaining substantially all of the immunologic activity of the native protein. When possible, it may be desirable to optimize HLA class I binding peptide epitopes of the invention to a length of about 8 to about 13 amino acid residues, preferably 9 to 10. It is to be appreciated that one or more epitopes in this size range can be comprised by a longer peptide (see the Definition Section for the term "epitope" for further discussion of peptide length). HLA class II binding epitopes are preferably optimized to a length of about 6 to about 30 amino acids in length, preferably to between about 13 and about 20 residues. Preferably, the epitopes are commensurate in size with endogenously processed pathogen-derived peptides or tumor cell peptides that are bound to the relevant HLA molecules. The identification and preparation of peptides of various lengths can be carried out using the techniques described herein.

An alternative preferred embodiment of the invention comprises administration of peptides of the invention linked as a polyepitopic peptide, or as a minigene that encodes a polyepitolpic peptide.

Another preferred embodiment is obtained by identifying native peptide regions that contain a high concentration of class I and/or class II epitopes. Such a sequence is generally selected on the basis that it contains the greatest number of epitopes per amino acid length. It is to be appreciated that epitopes can be present in a frame-shifted manner, e.g. a 10 amino acid long peptide could contain two 9 amino acid long epitopes and one 10 amino acid long epitope; upon intracellular processing, each epitope can be exposed and bound by an HLA molecule upon administration of such a peptide. Thus a larger, preferably multi-epitopic, peptide can be generated synthetically, recombinantly, or via cleavage from the native source.

V.H. Assays to Detect T-Cell Responses

Once HLA binding peptides are identified, they can be tested for the ability to elicit a T-cell response. The preparation and evaluation of motif-bearing peptides are described, e.g., in PCT publications WO 94/20127 and WO 94/03205. Briefly, peptides comprising epitopes from a particular antigen are synthesized and tested for their ability to bind to relevant HLA proteins. These assays may involve evaluation of peptide binding to purified HLA class I molecules in relation to the binding of a radioiodinated reference peptide. Alternatively, cells expressing empty class I molecules (i.e. cell surface HLA molecules that lack any bound peptide) may be evaluated for peptide binding by immunofluorescent staining and flow microfluorimetry. Other assays that may be used to evaluate peptide binding include peptide-dependent class I assembly assays and/or the inhibition of CTL recognition by peptide competition. Those peptides that bind to an HLA class I molecule, typically with an affinity of 500 nM or less, are further evaluated for their ability to serve as targets for CTLs derived from infected or immunized individuals, as well as for their capacity to induce primary in vitro or in vivo CTL responses that can give rise to CTL populations capable of reacting with selected target cells associated with pathology.

Analogous assays are used for evaluation of HLA class II binding peptides. HLA class II motif-bearing peptides that are shown to bind, typically at an affinity of 1000 nM or less, are further evaluated for the ability to stimulate HTL responses.

Conventional assays utilized to detect T cell responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations. Antigen-presenting Wells can be normal cells such as peripheral blood mononuclear cells or dendritic cells. Alternatively, mutant, non-human mammalian cell lines that have been transfected Keith a human class I MHC gene, and that are deficient in their ability to load class I molecules with internally processed peptides, are used to evaluate the capacity of the peptide to induce in vitro primary CTL responses. Peripheral blood mononuclear cells (PBMCs) can be used as the source of CTL precursors. Antigen presenting cells are incubated with peptide, after which the peptide-loaded antigen-presenting cells are then incubated with the responder cell population under optimized culture conditions. Positive CTL activation can be determined by assaying the culture for the presence of CTLs that lyse radio-labeled target cells, either specific peptide-pulsed targets or target cells that express (endogenously processed antigen from which the specific peptide was derived. Alternatively, the presence of epitope-specific CTLs can be determined by IFNγ in situ ELISA.

Additionally, a method has been devised which allows direct quantification of antigen-specific T cells by staining with fluorescein-labelled HLA tetrameric complexes (Altman, J. D. et al., *Proc. Natl. Acad. Sci. USA* 90:10330, 1993; Altman, J. D. et al., *Science* 274:94, 1996). Other options include staining for intracellular lymphokines, and interferon release assays or ELISPOT assays. Tetramer staining, intracellular lymphokine staining and ELISPOT assays all appear to be at least 10-fold more sensitive than more onventional assays (Lalvani, A. et al., *J. Exp. Med.* 186:859, 1997; Dunbar, P. R. et al., *Curr. Biol.* 8:413, 1998; Murali-Krishna, K. et al., *Immunity* 8:177, 1998).

HTL activation may also be assessed using techniques known to those in the art, such as T cell proliferation or lymphokine secretion (see, e.g. Alexander et al., Immunity 1:751–761, 1994).

Alternatively, immunization of HLA transgenic mice can be used to determine immunogenicity of peptide epitopes. Several transgenic mouse strains, e.g., mice with human A2.1, A11 (which can additionally be used to analyze HLA-A3 epitopes), and B7 alleles have been characterized. Other transgenic mice strains (e.g., transgenic mice for HLA-A1 and A24) are being developed. Moreover, HLA-DR1 and HLA-DR3 mouse models have been developed. In accordance with principles in the art, additional transgenic mouse models with other HLA alleles are generated as necessary.

Such mice can be immunized with peptides emulsified in Incomplete Freund's Adjuvant; thereafter any resulting T cells can be tested for their capacity to recognize target cells that have b en peptide-pulsed or transfected with genes encoding the peptide of interest. CTL responses can be analyzed using cytotoxicity assays described above. Similarly, HTL responses can be analyzed using, e.g., T cell proliferation or lymphokine secretion assays.

IV.I. Use of Peptide Epitopes as Diagnostic Agents for Evaluating Immune Responses In one embodiment of the invention, HLA class I and class II binding peptides can be used as reagents to evaluate an immune response. The evaluated immune response can be induced by any immunogen. For example, the immunogen may result in the production of antigen-specific CTLs or HTLs that recognize the peptide epitope(s) employed as the reagent. Thus, a peptide of the invention may or may not be used as the immunogen. Assay systems that can be used for such analyses include tetramer-based protocols, staining for intracellular lymphokines, interferon release assays, or ELISPOT assays.

For example, following exposure to a putative immunogen, a peptide of the invention can be used in a tetramer staining assay to assess peripheral blood mononuclear cells for the presence of any antigen-specific CTLs. The HLA-tetrameric complex is used to directly visualize antigen-specific CTLs and thereby determine the frequency of such antigen-specific CTLs in a sample of peripheral blood mononuclear cells (see, e.g., Ogg et al., *Science* 279:2103–2106, 1998; and Altman et al., *Science* 174:94–96, 1996).

A tetramer reagent comprising a peptide of the invention is generated as follows: A peptide that binds to an HLA molecule is refolded in the presence of the corresponding HLA heavy chain and $\beta_2$-microglobulin to generate a trimolecular complex. The complex is biotinylated at the carboxyl terminal end of the HLA heavy chain, at a site that was previously engineered into the protein. Tetramer formation is then induced by adding streptavidin. When fluorescently labeled streptavidin is used, the tetrameric complex is used to stain antigen-specific cells. The labeled cells are then readily identified, e.g., by flow cytometry. Such procedures are used for diagnostic or prognostic purposes; the cells identified by the procedure can be used for therapeutic purposes.

Peptides of the invention (see., e.g., Table 6) are also used as reagents to evaluate immune recall responses. (see, e.g., Bertoni et al., *J. Clin. Invest.* 100:503–513, 1997 and Penna et al., *J. Exp. Med.* 174:1565–1570, 1991.) For example, a PBMC sample from an individual expressing a disease-associated antigen (e.g. a tumor-associated antigen such as CEA, p53, MAGE2/3,HER2neu, or an organism associated with neoplasia such as HPV or HSV) can be analyzed for the presence of antigen-specific CTLs or HTLs using specific peptides. A blood sample containing mononuclear cells may be evaluated by cultivating the PBMCs and stimulating the cells with a peptide of the invention. After an appropriate cultivation period, the expanded cell population may be analyzed, for example, for CTL or for HTL activity.

Thus, the peptides can be used to evaluate the efficacy of a vaccine. PBMCs obtained from a patient vaccinated with an immunogen may be analyzed by methods such as those described herein. The patient is HLA typed, and peptide epitopes that are bound by the HLA molecule(s) present in that patient are selected for analysis. The immunogenicity of the vaccine is indicated by the presence of CTLs and/or HTLs directed to epitopes present in the vaccine.

The peptides of the invention may also be used to make antibodies, using techniques well known in the art (see, e.g. *Current Protocols in Immunology,* Wiley/Greene, NY; and *Antibodies A Laboratory Manual Harlow,* Harlow and Lane, Cold Spring Harbor Laboratory Press, 1989). Such antibodies are useful as reagents to determine the presence of disease-associated antigens. Antibodies in this category include those that recognize a peptide when bound by an HLA molecule, i.e., antibodies that bind to a peptide-MHC complex.

IV.J. Vaccine Compositions

Vaccines that contain an immunologically effective amount of one or more peptides of the invention are a further embodiment of the invention. The peptides can be delivered by various means or formulations, all collectively referred to as "vaccine" compositions. Such vaccine compositions, and/or modes of administration, can include, for example, naked cDNA in cationic lipid formulations; lipopeptides (e.g., Vitiello, A. et al.,*J. Clin. Invest.* 95:341, 1995), naked cDNA or peptides, encapsulated e.g., in poly(DL-lactide-co-glycolide) ("PLG") microspheres (see, e.g., Eldridge, et al., *Molec. Immunol.* 28:287–294, 1991: Alonso et al., *Vaccine* 12:299–306, 1994; Jones et al., *Vaccine* 13:675–681, 1995); peptide compositions contained in immune stimulating complexes (ISCOMS) (see, e.g., Takahashi et al., *Nature* 344:873–875, 1990; Hu et al., *Clin Exp Immunol.* 113:235–243, 1998); multiple antigen peptide systems (MAPs) (see e.g., Tam, J. P., *Proc. Natl. Acad. Sci. U.S.A.* 85:5409–5413, 1988; Tam, J. P., *J. Immunol. Methods* 196:17–32, 1996); viral, bacterial, or fungal delivery vectors (Perkus, M. E. et al., In: *Concepts in vaccine development,* Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990); particles of viral or synthetic origin (e.g., Kofler, N. et al.,*J. Immunol. Methods.* 192:25, 1996; Eldridge, J. H. et al., *Sem. Hematol.* 30:16, 1993; Falo, L. D., Jr. et al., *Nature Med.* 7:649, 1995); adjuvants (Warren, H. S., Vogel, F. R., and Chedid, L. A. *Annu. Rev. Immunol.* 4:369, 1986; Gupta, R. K. et al., *Vaccine* 11:293, 1993); liposomes (Reddy, R. et al., *J. Immunol.* 148:1585, 1992; Rock, K. L., *Immunol. Today* 17:131, 1996); or, particle-absorbed cDNA (Ulner, J. B. et al.,*Science* 259:1745, 1993; Robinson, H. L., Hunt, L. A., and Webster, R. G., *Vaccine* 11:957, 1993; Shiver, J. W. et al., In: *Concepts in vaccine development,* Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993), etc. Toxin-targeted delivery technologies, also known as receptor mediated targeting, such as those of Avant Immunotherapeutics, Inc. (Needham, Mass.) or attached to a stress protein, e.g., HSP 96 (Stressgen Biotechnologies Corp., Victoria, BC, Canada) can also be used.

Vaccines of the invention comprise nucleic acid mediated modalities. DNA or RNA encoding one or more of the peptides of the invention can be administered to a patient. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; and, WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687). Accordingly, peptide vaccines of the invention can be expressed by viral or bacterial vectors. Examples of expression vectors include attenuated viral hosts, such as vaccinia or fowlpox. For example, vaccinia virus is used as a vector to express nucleotide sequences that encode the peptides of the invention. Upon introduction into an acutely or chronically infected host or into a non-infected host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456–460 (1991). A wide variety of other vectors useful for therapeutic administration or immunization of the peptides of the invention, e.g. adeno and adeno-associated virus vectors, alpha virus vectors, retroviral vectors, *Salmonella typhi* vectors, detoxified anthrax toxin vectors, and the like, are apparent to those skilled in the art from the description herein.

Furthermore, vaccines in accordance with the invention can comprise one or more peptides of the invention. Accordingly, a peptide can be present in a vaccine individually; alternatively, the peptide can exist as a homopolymer comprising multiple copies of the same peptide, or as a heteropolymer of various peptides. Polymers have the advantage of increased probability for immunological reaction and, where different peptide epitopes are used to make up the polymer, the ability to induce antibodies and/or T cells that react with different antigenic determinants of the antigen targeted for an immune response. The composition may be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza virus proteins, hepatitis B virus core protein, and the like. The vaccines can contain a physiologically tolerable diluent such as water, or a saline solution, preferably phosphate buffered saline. Generally, the vaccines also include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glyceryl-cysteinyl-seryl-serine ($P_3CSS$).

Upon immunization with a peptide composition in accordance with the invention, via injection (e.g., SC, ID, IM), aerosol, oral, transdermal, transmucosal, intrapleural, intrathecal, or other suitable routes, the immune system of the host responds to the vaccine by producing antibodies, CTLs and/or HTLs specific for the desired antigen. Consequently, the host becomes at least partially immune to subsequent exposure to the TAA, or at least partially resistant to further development of TAA-bearing cells and thereby derives a prophylactic or therapeutic benefit.

In certain embodiments, components that induce T cell responses are combined with components that induce antibody responses to the target antigen of interest. A preferred embodiment of such a composition comprises class I and class II epitopes in accordance with the invention. Alternatively, a composition comprises a class I and/or class II epitope in accordance with the invention, along with a PADRETM molecule (Epimmune, San Diego, Calif.).

Vaccine of the invention can comprise antigen presenting cells, such as dendritic cells, as a vehicle to present peptides of the invention. For example, dendritic cells are transfected, e.g., with a minigene construct in accordance with the invention, in order to elicit immune responses. Minigenes are discussed in greater detail in a following section. Vaccine compositions can be created in vitro, following dendritic cell mobilization and harvesting, whereby loading of dendritic cells occurs in vitro.

The vaccine compositions of the invention may also be used in combination with antiviral drugs such as interferon-α, or immune adjuvants such as IL-12, GM-CSF, etc.

Preferably, the following principles are utilized when selecting epitope(s) for inclusion in a vaccine, either peptide-based or nucleic acid-based formulations. Exemplary epitopes that may be utilized in a vaccine to treat or prevent TAA-associated disease are set out in Table 6. Each of the following principles can be balanced in order to make the selection. When multiple epitopes are to be used in a vaccine, the epitopes may be, but need not be, contiguous in sequence in the native antigen from which the epitopes are derived.

1.) Epitopes are selected which, upon administration, mimic immune responses that have been observed to be correlated with prevention or clearance of TAA-expressing tumors. For HLA Class I, this generally includes 3–4 epitopes derived from at least one TAA.

2.) Epitopes are selected that have the requisite binding affinity established to be correlated with immunogenicity: for HLA Class I an $IC_{50}$ of 500 nM or less, or for Class II an $IC_{50}$ of 1000 nM or less. For HLA Class I it is presently preferred to select a peptide having an $IC_{50}$ of 200 nM or less, as this is believed to better correlate not only to induction of an immune response, but to in vitro tumor cell killing as well.

3.) Supermotif bearing-peptides, or a sufficient array of allele-specific motif-bearing peptides, are selected to give broad population coverage. In general, it is preferable to have at least 80% population coverage. A Monte Carlo analysis, a statistical evaluation known in the art, can be employed to assess the breadth of population coverage.

4.) When selecting epitopes from cancer-related antigens, it can be preferable to include analog peptides in the selection, because the patient may have developed tolerance to the native epitope. When selecting epitopes for infectious disease-related antigens it is presently preferable to select either native or analog epitopes.

5.) Of particular relevance are "nested epitopes." Nested epitopes occur where at least two epitopes overlap in a given peptide sequence. A peptide comprising "transcendent nested epitopes" is a peptide that has both HLA class I and HLA class II epitopes in it. When providing nested epitopes, it is preferable to provide a sequence that has the greatest number of epitopes per provided sequence. Preferably, one avoids providing a peptide that is any longer than the amino terminus of the amino terminal epitope and the carboxyl terminus of the carboxyl terminal epitope in the peptide. When providing a sequence comprising nested epitopes, it is important to evaluate the sequence in order to insure that it does not have pathological or other deleterious biological properties; this is particularly relevant for vaccines directed to infectious organisms.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

IV.J.1. Minigene Vaccines

A number of different approaches are available which allow simultaneous delivery of multiple epitopes. Nucleic acids encoding multiple epitopes are a useful embodiment of the invention; discrete peptide epitopes or polyepitopic peptides can be encoded. The epitopes to be included in a minigene are preferably selected according to the guidelines set forth in the previous section. Examples of amino acid sequences that can be included in a minigene include: HLA class I epitopes, HLA class II epitopes, a ubiquitination signal sequence, and/or a targeting sequence such as an endoplasmic reticulum (ER) signal sequence to facilitate movement of the resulting peptide into the endoplasmic reticulum.

The use of multi-epitope minigenes is also described in, e.g., co-pending application U.S. Ser. No. 09/311,784; Ishioka et al., *J. Immunol.* 162:3915–3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding nine dominant HLA-A*0201- and A11-restricted CTL epitopes derived from the polymerase, envelope, and core proteins of HBV and human immunodeficiency virus (HIV), a PADRE® universal helper T cell (HTL) epitope, and an endoplasmic reticulum-translocating signal sequence has been engineered. Immunization of HLA transgenic mice with this plasmid construct resulted in strong CTL induction responses against the nine CTL epitopes tested. This CTL response was similar to that observed with a lipopeptide of known immunogenicity in humans, and significantly greater than immunization using peptides in oil-based adjuvants. Moreover, the immunogenicity of DNA-encoded epitopes in vitro was also correlated with the in vitro responses of specific CTL lines against target cells transfected with the DNA plasmid. These data show that the minigene served: 1.) to generate a CTL response and 2.) to generate CTLs that recognized cells expressing the encoded epitopes. A similar approach can be used to develop minigenes encoding TAA epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. However, to optimize expression and/or immunogenicity, additional elements can be incorporated into the minigene design such as spacer amino acid residues between epitopes. HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30–100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a downstream cloning site for minigene insertion; a polyadenylation signal for efficient transcription termination; an E. coli origin of replication; and an E. coli selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Optimized peptide expression and immunogenicity can be achieved by certain modifications to a minigene construct. For example, in some cases introns facilitate efficient gene expression, thus one or more synthetic or naturally-occurring introns can be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate bacterial strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as cell banks.

In addition, immunostimulatbry sequences (ISSs or CpGs) appear to play a role in the immunogenicity of DNA vaccines. These sequences may be included in the vector, outside the minigene coding sequence to enhance immunogenicity.

In some embodiments, a bi-cistronic expression vector which allows production of both the minigene-encoded epitopes and a second protein (e.g., one that modulates immunogenicity) can be used. Examples of proteins or polypeptides that, if co-expressed with epitopes, can enhance an immune response include cytokines (e.g., IL-2, IL-12, GM-CSF), cytokine-inducing molecules (e.g., LeIF), costimulatory molecules, or pan-DR binding proteins (PADRE®, Epimmune, San Diego, Calif.). Helper T cell (HTL) epitopes such as PADRE® molecules can be joined to intracellular targeting signals and expressed separately from expressed CTL epitopes. This can be done in order to direct HTL epitopes to a cell compartment different than that of the CTL epitopes, one that provides for more efficient entry of HTL epitopes into the HLA class II pathway, thereby improving HTL induction. In contrast to HTL or CTL induction, specifically decreasing the immune response by co-expression of immunosuppressive molecules (e.g. TGF-b) may be beneficial in certain diseases.

Therapeutic quantities of plasmid DNA can be produced for example, by fermentation in E. coli, followed by purification. Aliquots from the working cell bank are used to inoculate growth medium, and are grown to saturation in shaker flasks or a bioreactor according to well known techniques. Plasmid DNA is purified using standard bio-separation technologies such as solid phase anion-exchange resins available e.g., from QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene vaccines, alternative methods of formulating purified plasmid DNA may be used. A variety of such methods have been described, and new techniques may become available. Cationic lipids, glycolipids, and fusogenic liposomes can also be used in the formulation (see, e.g., WO 93/24640; Mannino & Gould-Fogerite, BioTechniques 6(7): 682 (1988); U.S. Pat. No. 5,279,833; WO 91/06309; and Felgner, et al., Proc. Nat'l Acad. Sci. USA 84:7413 (1987). In addition, peptides and compounds referred to collectively as protective, interactive, non-condensing compounds (PINC) can also be complexed to purified plasmid DNA to influence variables such as stability, intramuscular dispersion, or trafficking to specific organs or cell types.

Target cell sensitization can be used as a functional assay of the expression and HLA class I presentation of minigene-encoded epitopes. For example, the plasmid DNA is introduced into a mammalian cell line that is a suitable target for standard CTL chromium release assays. The transfection method used will be dependent on the final formulation, electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). The transfected cells are then chromium-51 ($^{51}$Cr) labeled and used as targets for epitope-specific CTLs. Cytolysis of the target cells, detected by $^{51}$Cr release, indicates both the production and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (IP) for lipid-complexed DNA). Eleven to twenty-one days after immunization, splenocytes are harvested and restimulated for one week in the presence of peptides encoding each epitope being tested. Thereafter, for CTLs, standard assays are conducted to determine if there is cytolysis of peptide-loaded, $^{51}$Cr-labeled target cells. Once again, lysis of target cells that were exposed to epitopes corresponding to those in the minigene, demonstrates DNA vaccine function and induction of CTLs. Immunogenicity of HTL epitopes is evaluated in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment for ballistic delivery, DNA can be adhered to particles, such as gold particles.

IV.J.2. Combinations of CTL Peptides with Helper Peptides

Vaccine compositions comprising CTL peptides of the present invention can be modified to provide desired attributes, such as improved serum half-life, broadened population coverage or enhanced immunogenicity.

For instance, the ability of a peptide to induce CTL activity can be enhanced by linking the CTL peptide to a sequence which contains at least one HTL epitope. The use of T helper epitopes in conjunction with CTL epitopes to eihance immunogenicity is illustrated, for example, in co-pending applications U.S. Ser. Nos. 08/820,360, 08/197,484, and 08/464,234.

Although a CTL peptide can be directly linked to a T helper peptide, particularly preferred CTL epitope/HTL epitope conjugates are linked by a spacer molecule. The spacer is typically comprised of relatively small, neutral molecules, e.g., amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optional spacer need not be comprised of the same residues and thus may be a hetero- or homo-oligomer. When present, the spacer will usually be at least one or two residues, commonly three to 13, more frequently three to six residues. The CTL peptide epitope may be linked to the T helper peptide epitope, directly or via a spacer, at either it's amino or carboxyl terminus. The amino terminus of either the CTL peptide or the HTL peptide can be acylated.

In certain embodiments, the T helper peptide is one that is recognized by T helper cells present in the majority of the population. This can be accomplished by selecting amino acid sequences that bind to many, most, or all of the HLA class II molecules. These are known as "loosely HLA-restricted" or "promiscuous" T helper sequences. Examples of amino acid sequences that are promiscuous include sequences from antigens such as tetanus toxoid at positions 830–843 (QYIKANSKFIGITE; SEQ ID NO:38), *Plasmodium falciparum* CS protein at positions 378–398 (DIEKKIAKMEKASSVFNVVNS; SEQ ID NO:39), and Streptococcus 18 kD protein at positions 116 (GAVDSILGGVATYGAA; SEQ ID NI:40). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences that may not be found in nature. Synthetic compounds fall within the family of molecules called Pan-DR-binding epitopes (e.g., PADRE®, Epimmune Inc., San Diego, Calif.). PADRE® peptides are designed to bind multiple HLA-DR (human HLA class II) molecules. For instance, a pan-DR-binding epitope peptide having the formula: aKXVAAZTLKAAa, where "X" is either cyclohexylalanine, phenylalanine, or tyrosine; "Z" is either tryptophan, tyrosine, histidine or asparagine; and "a" is either D-alanine or L-alanine, has been found to bind to numerous allele-specific HLA-DR molecules. Accordingly, these molecules stimulate a T helper lymphocyte response from most individuals, regardless of their HLA type. Certain pan-DR binding epitopes comprise all "L" natural amino acids; these molecules can be provided as peptides or in the form of nucleic acids that encode the peptide.

HTL peptide epitopes can be modified to alter their biological properties. HTL peptide epitopes can be modified in the same manner as CTL peptides. For instance, they may be modified to include D-amino acids or be conjugated to other molecules such as lipids, proteins, sugars and the like. Peptides comprising D-amino acids generally have increased resistance to proteases, and thus have an extended serum half-life.

In addition, peptides of the invention can be conjugated to other molecules such as lipids, proteins or sugars, or any other synthetic compounds, to increase their biological activity. For example, a T helper peptide can be conjugated to one or more palmitic acid chains at either the amino or the carboxyl termini.

I.V.J.3. Combinations of CTL Peptides with T Cell Priming Materials

In some embodiments it may be desirable to include in the pharmaceutical compositions of the invention at least one component which primes cytotoxic T lymphocytes. Lipids have been identified as agents capable of facilitating the priming in vitro CTL response against viral antigens. For example, palmitic acid residues can be attached to the $\epsilon$- and $\alpha$-amino groups of a lysine residue and then linked to an immunogenic peptide. One or more linking moieties can be used such as Gly, Gly-Gly-, Ser, Ser-Ser, or the like. The lipidated peptide can then be administered directly in a micelle or particle, incorporated into a liposome, or emulsified in an adjuvant, e.g., incomplete Freund's adjuvant. A preferred immunogenic composition comprises palmitic acid attached to $\epsilon$- and $\alpha$- amino groups of Lys via a linking moiety, e.g., Ser-Ser, added to the amino terminus of an immunogenic peptide.

In another embodiment of lipid-facilitated priming of CTL responses, *E. coli* lipoproteins, such as tripalmitoyl-S-glyceryl-cysteinyl-seryl-serine (P$_3$CSS) can be used to prime CTL when covalently attached to an appropriate peptide. (See, e.g., Deres, et al., *Nature* 342:561, 1989). Thus, peptides of the invention can be coupled to P$_3$CSS, and the lipopeptide administered to an individual to specifically prime a CTL response to the target antigen. Moreover, because the induction of neutralizing antibodies can also be primed with P$_3$CSS-conjugated epitopes, two such compositions can be combined to elicit both humoral and cell-mediated responses.

IV.J.4. Vaccine Compositions Comprising Dendritic Cells Pulsed with CTL and/or HTL Peptides An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes in HLA molecules on their surfaces.

The DC can be pulsed ex vivo with a cocktail of peptides, some of which stimulate CTL responses to one or more antigens of interest, e.g., tumor associated antigens (TAA) such as HER2/neu, p53, MAGE 2, MAGE3, and/or carcinoembryonic antigen (CEA). Collectively, these TAA are associated with breast, colon and lung cancers. Optionally, a helper T cell (HTL) peptide such as PADRE, can be included to facilitate the CTL response. Thus, a vaccine in accordance with the invention comprising epitopes from HER2/neu, p53, MAGE 2, MAGE3, and carcinoembryonic antigen (CEA) is used to treat minimal or residual disease in patients with malignancies such as breast, colon or lung cancer; any malignancies that bear any of these TAAs can also be treated with the vaccine. A TAA vaccine can be used following debulking procedures such as surgery, radiation therapy or chemotherapy, whereupon the vaccine provides the benefit of increasing disease free survival and overall survival in the recipients.

Thus, in preferred embodiments, a vaccine of the invention is a product that treats a majority of patients across a number of different tumor types. A vaccine comprising a plurality of epitopes, preferably supermotif-bearing epitopes, offers such an advantage.

IV.K Administration of Vaccines for Therapeutic or Prophylactic Purposes

The peptides of the present invention, including pharmaceutical and vaccine compositions thereof, are useful for administration to mammals, particularly humans, to treat and/or prevent disease. In one embodiment, vaccine compositions (peptide or nucleic acid) of the invention are administered to a patient who has a malignancy associated with expression of one or more TAAs, or to an individual susceptible to, or otherwise at risk for developing TAA-related disease. Upon administration an immune response is elicited against the TAAs, thereby enhancing the patient's own immune response capabilities. In therapeutic applications, peptide and/or nucleic acid compositions are administered to a patient in an amount sufficient to elicit an effective immune response to the TAA-expressing cells and to thereby cure, arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

The vaccine compositions of the invention can be used purely as prophylactic agents. Generally the dosage for an initial prophylactic immunization generally occurs in a unit dosage range where the lower value is about 1, 5, 50, 500, or 1000 $\mu$g of peptide and the higher value is about 10,000; 20,000; 30,000; or 50,000 $\mu$g of peptide. Dosage values for a human typically range from about 500 $\mu$g to about 50,000 $\mu$g of peptide per 70 kilogram patient. This is followed by boosting dosages of between about 1.0 $\mu$g to about 50,000 $\mu$g of peptide, administered at defined intervals from about four weeks to six months after the initial administration of vaccine. The immunogenicity of the vaccine may be assessed by measuring the specific activity of CTL and HTL obtained from a sample of the patient's blood.

As noted above, peptides comprising CTL and/or HTL epitopes of the invention induce immune responses when presented by HLA molecules and contacted with a CTL or HTL specific for an epitope comprised by the peptide. The manner in which the peptide is contacted with the CTL or HTL is not critical to the invention. For instance, the peptide can be contacted with the CTL or HTL either in vitro or in vivo. If the contacting occurs in vivo, peptide can be administered directly, or in other forms/vehicles, e.g., DNA vectors encoding one or more peptides, viral vectors encoding the peptide(s), liposomes, antigen presenting cells such as dendritic cells, and the like, as described herein.

Accordingly, for pharmaceutical compositions of the invention in the form of peptides or polypeptides, the peptides or polypeptides can be administered directly. Alternatively, the peptide/polypeptides can be administered indirectly presented on APCs, or as DNA encoding them. Furthermore, the peptides or DNA encoding them can be administered individually or as fusions of one or more peptide sequences.

For therapeutic use, administration should generally begin at the first diagnosis of TAA-related disease. This is followed by boosting doses at least until symptoms are substantially abated and for a period thereafter. In chronic disease states, loading doses followed by boosting doses may be required.

The dosage for an initial therapeutic immunization generally occurs in a unit dosage range where the lower value is about 1, 5, 50, 500, or 1,000 $\mu$g of peptide and the higher value is about 10,000; 20,000; 30,000; or 50,000 $\mu$g of peptide. Dosage values for a human typically range from about 500 $\mu$g to about 50,000 $\mu$g of peptide per 70 kilogram patient. Boosting dosages of between about 1.0 $\mu$g to about 50,000 $\mu$g of peptide, administered pursuant to a boosting regimen over weeks to months, can be administered depending upon the patient's response and condition. Patient response can be determined by measuring the specific activity of CTL and HTL obtained from the patient's blood.

In certain embodiments, peptides and compositions of the present invention are used in serious disease states. In such cases, as a result of the minimal amounts of extraneous substances and the relative nontoxic nature of the peptides, it is possible and may be desirable to administer substantial excesses of these peptide compositions relative to these stated dosage amounts.

For treatment of chronic disease, a representative dose is in the range disclosed above, namely where the lower value is about 1, 5, 50, 500, or 1,000 $\mu$g of peptide and the higher value is about 10,000; 20,000; 30,000; or 50,000 $\mu$g of peptide, preferably from about 500 $\mu$g to about 50,000 $\mu$g of peptide per 70 kilogram patient. Initial doses followed by boosting doses at established intervals, e.g., from four weeks to six months, may be required, possibly for a prolonged period of time to effectively immunize an individual. In the case of chronic disease, administration should continue until at least clinical symptoms or laboratory tests indicate that the disease has been eliminated or substantially abated, and for a follow-up period thereafter. The dosages, routes of administration, and dose schedules are adjusted in accordance with methodologies known in the art.

The pharmaceutical compositions for therapeutic treatment are intended for parenteral, topical, oral, intrathecal, or local administration. Preferably, the pharmaceutical compositions are administered parentally, e.g., intravenously, subcutaneously, intradermally, or intramuscularly.

Thus, a preferred embodiment the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances or pharmaceutical excipients as may be required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of the peptide composition is typically included in a pharmaceutical composition that also comprises a human unit dose of an acceptable carrier, preferably an aqueous carrier, and is administered in a volume of fluid that is known by those of skill in the art to be used for administration of such compositions to humans (see, e.g., *Remington's Pharmaceutical Sciences*, 17$^{th}$ Edition, A. Gennaro, Editor, Mack Publishing Co., Easton, Pa., 1985).

The peptides of the invention can also be administered via liposomes, which serve to target the peptides to a particular tissue, such as lymphoid tissue, or to target selectively to infected cells, as well as to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells (such as monoclonal antibodies which bind to the CD45 antigen) or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting compositions of the invention to cells of the immune system, a ligand can be incorporated into the liposome, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, often at a concentration of 25%–75%.

For aerosol administration, the immunogenic peptides are preferably supplied in finely divided form, along with a surfactant and propellant. Typical percentages of peptides are 0.01%–20% by weight, often 1%–10%. The surfactant must, of course, be pharmaceutically acceptable, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant, although an atomizer may be used in which no propellant is necessary and other percentages are adjusted accordingly. A carrier can also be included, e.g., lecithin for intranasal delivery.

Antigenic peptides of the invention have been used to elicit a CTL and/or HTL response ex vivo, as well. The resulting CTLs or HTLs can be used to treat chronic infections, or tumors in patients that do not respond to other conventional forms of therapy, or who do not respond to a therapeutic peptide or nucleic acid vaccine in accordance with the invention. Ex vivo CTL or HTL responses to a particular antigen (infectious or tumor-associated) are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7–28 days), in which the precursor cells are activated and expanded into effector cells, the cells are infused back into the patient, where they will destroy (CTL) or facilitate destruction (HTL) of their specific target cell (an infected cell or a tumor cell).

IV.L. Kits

The peptide and nucleic acid compositions of this invention can be provided in kit form together with instructions for vaccine administration. Typically the kit would include desired composition(s) of the invention in a container, preferably in unit dosage form and instructions for administration. For example, a kit would include an APC, such as a dendritic cell, previously exposed to and now presenting peptides of the invention in a container, preferably in unit dosage form together with instructions for administration. An alternative kit would include a minigene construct with desired nucleic acids of the invention in a container, preferably in unit dosage form together with instructions for administration. Lymphokines such as IL-2 or IL-12 may also be included in the kit. Other kit components that may also be desirable include, for example, a sterile syringe, booster dosages, and other desired excipients.

The invention will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments in accordance with the invention.

V. EXAMPLES

Example 1

Selection of Tumor Associated Antigens

Vaccines which bind to HLA supertypes, A2, A3, and B7, will afford broad, non-ethnically biased population coverage (83–88%). Since the A2 supertype is broadly expressed in the population (39–49%), peptides which bind to this family of molecules provide a reasonable starting point for the use of peptide-based vaccines. While the A2 vaccine targets patients that express HLA-A2 molecules, the approach can be readily extended to include peptide(s) that bind to additional alleles or supertype groups thereof.

Whole proteins often induce an immune response limited to specific epitopes that may be ineffective in mediating effective anti-tumor immune responses (Disis et al., *J. Immunology* 156:3151–3158 (1996); Manca et al., *J. Immunology* 146:1964–1971 (1991)). A epitope-based vaccine circumvents this limitation through the identification of peptide epitopes embedded in TAAs. Exemplary TAAs are set forth in Table 12.

Peptides were evaluated based upon MHC binding motifs, on the capacity to bind MHC molecules, and the ability to activate tumor-reactive CTL in vitro using lymphocyte cultures from normal individuals. This approach has several advantages. First, it does not require the isolation of patient-derived cells such as CTL or tumor cells. Secondly, the identification of epitopes that stimulate CTL in normal individuals permits the identification of a broad range of epitopes, including subdominant as well as dominant epitopes.

Four tumor-associated antigens, CEA, p53, MAGE 2/3 and HER2/neu, are expressed in various tumor types (Kawashima et al., *Human Immunology* 59:1–14 (1998); Tomlinson, et al., *Advanced Drug Delivery Reviews*, Vol. 32(3) (Jul. 6, 1998)). In a preferred embodiment, a vaccine comprises epitopes (as one or more peptides or as nucleic acids encoding them) from among these four, or any other, TAAs. Accordingly, this vaccine induces CTL responses against several major cancer types.

CEA is a 180 kD cell surface and secreted glycoprotein produced by a number of different tumors at high levels of expression, particularly colon cancer. This antigen is present in normal physiology associated with fetal tissue (see, e.g., Ruddon, R., *Cancer Biology*, $3^{rd}$ ed., p 126 (1995); and copending U.S. Ser. No. 09/458,302, filed Dec. 10, 1999)). The abnormally high expression on cancer cells makes CEA an important target for immunotherapy.

MAGE, melanoma antigens, are a family of related proteins whose expression is normally limited to testis and placenta, but are also expressed by melanomas and a variety of other carcinomas. These proteins are known to be recognized by cytotoxic T cells (see, e.g., copending U.S. Ser. No. 09/458,298, filed Dec. 10, 1999).

HER2/neu (erbB-2) is a 185 kD transmembrane protein that is similar to the EGF receptor. HER2/neu is a tyrosine kinase capable of autophosphorylation. Over-expression of HER2/neu is correlated with oncogenic transformation. It is expressed primarily in breast, ovarian and gastric cancers (see, e.g., copending U.S. Ser. No. 09/458,299, filed Dec. 10, 1999).

A fourth TAA targeted, p53, is normally a tumor suppressor gene but can be mutated. The mutations result in increased protein stability and hence over-expression. The protein, p53, has been observed in colon, lung, prostate and osteosarcomas as well as other tumors (see, e.g., copending U.S. Ser. No. 09/458,297, filed Dec. 10, 1999). Preferably, p53 peptides in a vaccine of the invention are derived from non-mutated sequences that are common between all cancer patients.

Other TAAs that can be included in a vaccine composition are associated with prostate cancer (see, e.g., copending Provisional Application U.S. Ser. No. 60/171312, filed December 1999, now abandoned).

Table 7 below delineates the tumor antigen expression in breast, colon and lung. By targeting four TAA, the likelihood of the mutation of tumor cells (tumor escape) into cells which do not express any of the tumor antigens is decreased. Preferably, the inclusion of two or more epitopes from each TAA serves to increase the likelihood that individuals of different ethnicity will respond to the vaccine and provides broadened population coverage.

This rational approach to vaccine compositions can be focused on a particular HLA allele, or extended to various HLA molecules or supertypes to further extend population coverage.

Table 8 shows the incidence, 5-year survival rates, and the estimated number of deaths per year for these tumors in the U.S for each type of cancer in Table 7. In terms of estimated new cases, estimated deaths and 5 year survival rates each of these tumor types has a large unmet need. Globally, the incidence of these tumors is significantly greater Example 2

Identification of Motif-Bearing Peptides

Protein sequences from the four targeted tumor antigens (CEA, p53, MAGE 2/3 and HER2/neu) were analyzed, to identify 8-, 9-, 10-, and 11-mer sequences containing the HLA-A2 supertype binding motif. This motif [leucine (L), isoleucine (I), valine (V), methionine (M), alanine (A), threonine (T), or glutamine (Q) at position 2, and leucine (L), isoleucine (I), valine (V), methionine (M), alanine (A), or threonine (T) at the C-terminus; see Table 2] is the predominant factor in determining peptide binding to the HLA molecules within the A2 supertype (see, e.g., del Guercio et al., *J. Immunol.*, 154:685–693 (1995); Sette, A. and Sidney, J., *Cur. Opin. Immunol.*, 10: 478–482 (1998); Sidney et al., *Immunology Today*, 17:261–266 (1996)). Nonamer and decamer sequences were further characterized using an A2-specific algorithm to evaluate secondary anchor residues (Ruppert et al., *Cell* 74:929–937 (1993); Gulukota et al., *J. Mol. Biol.* 267:1258–1267 (1997)).

Example 3

Molecular Binding Assays

Native sequences containing HLA-A2 peptide motifs were tested directly for binding to human class I HLA molecules, since a subset of motif-bearing peptides bind with a biologically significant affinity, data depicted in Table 6. An affinity threshold $\leq 500$ nM to the HLA-A2 molecule was previously shown to define the capacity of a peptide epitope to elicit a CTL response (Sette et al., *J. Immunol.* 153:5586–5592 (1994)). A competitive inhibition assay using purified HLA molecules was used to quantify peptide binding. Motif-bearing peptides were initially tested for binding to HLA-A*0201, the prototype member of the HLA-A2 supertype. Peptides binding to A*0201 with an $IC_{50} \leq 500$ nM were subsequently tested for their capacity to bind other predominant molecules of the A2 supertype: A*0202, A*0203, A*0206 and A*6802 (del Guercio et al., *J. Immunol.*, 154:685–693 (1995); Sette, A. and Sidney, J., *Cur. Opin. Immunol.*, 10: 478–482 (1998); Sidney et al., *Immunology Today*, 17:261–266 (1996)). A*0201-binding peptides found to bind at least one additional A2 supertype member were selected for further testing. Analogs of the native sequences for the CEA and p53 were evaluated to identify additional CTL peptide epitopes, as described below.

Example 4

A2 Epitope Identification

Since HLA-A2 is a species restricted molecule, the binding and functional activities of the A2 vaccine epitopes were measured in vitro using human molecules and cells. CTL epitopes were identified that demonstrated high or intermediate HLA-A2 binding affinity ($IC_{50}$ of $\leq 500$ nM). These epitopes also bound to at least one additional member of the HLA-A2 supertype family with an $IC_{50} \leq 500$ nM. Each epitope stimulated the in vitro induction of a specific human CTL that recognized and lysed peptide-pulsed target cells and tumor cell lines expressing the relevant TAA. A PADRE molecule is optionally included in the vaccine to promote the induction of long lasting CTL responses (Alexander et al., *Immunologic Research*, In Press.).

Immunological responses were demonstrated by in vitro induction of human CTL that were capable of recognizing both peptide-pulsed cells and TAA-expressing tumor cell lines. In certain cases, analog peptides were selected based on either improved binding affinity or supertype coverage relative to the native peptide and in one case, substitution of a cysteine with another amino acid.

Analogous assays can be used for other HLA types.

Example 5

Peptide Analogs Increase Supertype Cross-reactivity or Improve Chemical Characteristics Class I HLA peptides can be modified, or "analoged" by substitution of amino acids at a given position to increase their HLA binding affinity and/or supertype cross-reactivity (see, e.g., Table 2, and Zitvogel et al., *J. Exp Med* 183:87–97 (1996); Sette, et al., *J. Immunol.* 153:5586–5592 (1994)). The amino acids at position 2 and the C terminus of a peptide are the primary contact or "anchor" residues that interact with the HLA-A2 binding pocket. In order to identify analogs for inclusion in a composition of the invention, anchor residues were modified by substitution with a presently preferred or less preferred anchor residue, at position 2 and/or at the C-terminus.

Another type of modification utilized involved the substitution of α-amino butyric acid (B) for endogenous cysteine (C) residues to avoid the potential complication of disulfide bridge formation during product development.

For example, two criteria that were used to select native peptides to be analoged: 1) presence of a suboptimal anchor residue; and 2) at least weak binding ($IC_{50}$=500–5000 nM) of the parent peptide to at least two or three alleles of a supertype.

Peptides can also be analoged by modification of a secondary anchor residue. For example, in preferred approaches, a peptide can be analoged by removal of a deleterious residue in favor of an acceptable or preferred one; an acceptable residue can be exchanged for a different acceptable residue or a preferred residue, or a preferred residue can be exchanged for another preferred one.

Accordingly, peptide sequences were modified using one or more of the strategies described above. The peptides were tested for HLA-A2 supertype binding using the molecular binding assay. Supertype-binding data for analog peptides are shown in Table 6.

Example 6

Cellular Immunogenicity Screening

The peptides of the invention were also evaluated for their potential to stimulate CTL precursor responses to the TAA-derived peptide (in vitro primary CTL induction) and CTL recognition of tumor cells expressing the target TAA peptide epitope (recognition of endogenous targets). These criteria provided evidence that the peptides are functional epitopes.

In Vitro Primary CTL Induction

Peripheral blood monocytic cell-derived (or bone-marrow-derived) human DC, generated in vitro using GM-CSF and IL-4 and pulsed with a peptide of interest, were used as antigen presenting cells (APCs) in primary CTL induction cultures. The peptide pulsed DC were incubated with CD8 T cells (positively selected from normal donor lymphocytes using magnetic beads) which served as the source of CTL precursors. One week after stimulation with peptide, primary cultures were tested for epitope-specific CTL activity using either a standard chromium-release assay which measures cytotoxicity or a sandwich ELISA-based interferon gamma (IFNγ) production assay. Each of the CTL epitopes of Table 6 stimulated CTL induction from CD8 T cells of normal donors.

Recognition of Endogenous Targets

As described herein, T cell cultures testing positive for recognition of peptide-pulsed targets were expanded and evaluated for their ability to recognize human tumor cells that endogenously express the TAA. The chromium-release and IFNγ production assays were used for these evaluations, with tumor cell lines serving as the targets. Tumor cell lines lacking expression of either the TAA or the HLA-A2.1 molecule served as the negative control for non-specific activity. CTL cultures were generated which recognized tumor cells in a peptide-specific and HLA-A2-restricted manner (Table 6).

The HLA receptor binding and immunogenicity characteristics of CTL peptides are summarized in Table 6.

Example 7

A PADRE Molecule as a Helper Epitope for Enhancement of CTL Induction

There is increasing evidence that HTL activity is critical for the induction of long lasting CTL responses (Livingston et al. *J. Immunol* 162:3088–3095 (1999); Walter et al., *New Engl. J. Med.* 333:1038–1044 (1995); Hu et al., *J. Exp. Med.* 177:1681–1690 (1993)). Therefore, one or more peptides that bind to HLA class II molecules and stimulate HTLs can be used in accordance with the invention. Accordingly, a preferred embodiment of a vaccine includes a molecule from the PADRE® family of universal T helper cell epitopes (HTL) that target most DR molecules in a manner designed to stimulate helper T cells. For instance, a pan-DR-binding epitope peptide having the formula: aKXVAAZTLKAAa, where "X" is either cyclohexylalanine, phenylalanine, or tyrosine; "Z" is either tryptophan, tyrosine, histidine or asparagine; and "a" is either D-alanine or L-alanine, has been found to bind to most HLA-DR alleles, and to stimulate the response of T helper lymphocytes from most individuals, regardless of their HLA type.

A particularly preferred PADRE® molecule is a synthetic peptide, aKXVAAWTLKAAa (a=D-alanine, X=cyclohexylalanine), containing non-natural amino acids, specifically engineered to maximize both HLA-DR binding capacity and induction of T cell immune responses.

Alternative preferred PADRE® molecules are the peptides, aKFVAAWTLKAAa, aKYVAAWTLKAAa, aKFVAAYTLKAAa, aKXVAAYTLKAAa, aKYVAAYTLKAAa, IaKFVAAHTLKAAa, aKXVAAHTLKAAa, aKYVAAHTLKAAa, aKFVAANTLKAAa, aKXVAANTLKAAa, aKYVAANTLKAAa, AKXVAAWTLKAAA, AKFVAAWTLKAAA, AKYVAAWTLKAAA, AKFVAAYTLKAAA, AKXVAAYTLKAAA, AKYVAAYTLKAAA, AKFVAAHTLKAAA, AKXVAAHTLKAAA, AKYVAAHTLKAAA, AKFVAANTLKAAA, AKXVAANTLKAAA, AKYVAANTLKAAA (a=D-alanine, X=cyclohexylalanine).

In a presently preferred embodiment, the PADRE® peptide is amidated. For example, a particularly preferred amidated embodiment of a PADRE® molecule is conventionally written aKXVAAWTLKAAa-NH$_2$.

Competitive inhibition assays with purified HLA-DR molecules demonstrated that the PADRE® molecule aKXVAAWTLKAAa-NH$_2$ binds with high or intermediate affinity (IC$_{50}$£1,000 nM) to 15 out of 16 of the most prevalent HLA-DR molecules ((Kawashima et al., *Human Immunology* 59:1–14 (1998); Alexander et al., *Immunity* 1:751–761 (1994)). A comparison of the DR binding capacity of PADRE® and tetanus toxoid (TT) peptide 830–843, a "universal" epitope has been published (Panina-Bordignon et al., *Eur. J. Immunology* 19:2237–2242 (1989)). The TT 830–843 peptide bound to only seven of 16 DR molecules tested, while PADRE® bound 15 of 16. At least 1 of the 15 DR molecules that bind PADRE® is predicted to be present in >95% of all humans. Therefore, this PADRE® molecule is anticipated to induce an HTL response in virtually all patients, despite the extensive polymorphism of HLA-DR molecules in the human population.

PADRE® has been specifically engineered for optimal immunogenicity for human T cells. Representative data from in vitro primary immunizations of normal human T cells with Tr 830–843 antigen and the PADRE® molecule aKXVAAWTLKAAa-NH$_2$ are shown in FIG. 1. Peripheral blood mononuclear cells (PBMC) from three normal donors were stimulated with the peptides in vitro. Following the third round of stimulation, it was observed that PADRE® generated significant primary T cell responses for all three donors as measured in a standard T cell proliferation assay. With the PADRE® peptide, the 10,000 cpm proliferation level was generally reached with 10 to 100 ng/ml of antigen. In contrast, TT 830–843 antigen generated responses for only 2 out of 3 of the individuals tested. Responses approaching the 10,000 cpm range were reached with about 10,000 ng/ml of antigen. In this respect, it was noted that PADRE® was, on a molar basis, about 100-fold more potent than TT 830–843 antigen for activation of T cell responses.

Early data from a phase I/II investigator-sponsored trial, conducted at the University of Leiden (C. J. M. Melief), support the principle that the PADRE® molecule aKXVAAWTLKAAa, possibly the amidated aKXVAAWTLKAAa-NH$_2$, is highly immunogenic in humans (Ressing et al., *Detection of immune responses to helper peptide, but not to viral CTL epitopes, following peptide vaccination of immunocompromised patients with recurrent cervical carcinoma*. Submitted (1999)). In this trial, a PADRE® molecule was co-emulsified with various human papilloma virus (HPV)-derived CTL epitopes and was injected into patients with recurrent or residual cervical carcinoma. However, because of the late stage of carcinoma with the study patients, it was expected that these patients were immunocompromised. The patients' immunocompromised status was demonstrated by their low frequency of influenza virus-specific CTL, reduced levels of CD3 expression, and low incidence of proliferative recall responses after in vitro stimulation with conventional antigens. Thus, no efficacy was anticipated in the University of Leiden trial, rather the goal of that trial was essentially to evaluate safety. Safety was, in fact, demonstrated. In addition to a favorable safety profile, PADRE® T cell reactivity was detected in four of 12 patients (FIG. 2) in spite of the reduced immune competence of these patients.

Thus, the PADRE® peptide component(s) of the vaccine bind with broad specificity to multiple allelic forms of HLA-DR molecules. Moreover, PADRE® peptide component(s) bind with high affinity (IC$_{50}$£1000 nM), i.e., at a level of affinity correlated with being immunogenic for HLA Class II restricted T cells. The in vivo administration of PADRE® peptide(s) stimulates the proliferation of HTL in normal humans as well as patient populations.

Example 8

Functional Competence of ProGP-Derived DC

One embodiment of a vaccine in accordance with the invention comprises epitope-bearing peptides of the invention delivered via dendritic cells (DC). Accordingly, DC were evaluated in both in vitro and in vivo immune function assays. These assays include the stimulation of CTL hybridomas and CTL cell lines, and the in vivo activation of CTL.

DC Purification

ProGP-mobilized DC were purified from peripheral blood (PB) and spleens of ProGP-treated C57B1/6 mice to evaluate their ability to present antigen and to elicit cellular immune responses. Briefly, DC were purified from total WBC and spleen using a positive selection strategy employing magnetic beads coated with a CD11c specific antibody (Miltenyi Biotec, Auburn Calif.). For comparison, ex vivo expanded DC were generated by culturing bone marrow cells from untreated C57B1/6 mice with the standard cocktail of GM-CSF and IL-4 (R&D Systems, Minneapolis, Minn.) for a period of 7–8 days (Mayordomo et al., *Nature Med.* 1:1297–1302 (1995)). Recent studies have revealed that this ex vivo expanded DC population contains effective antigen presenting cells, with the capacity to stimulate anti-tumor immune responses (Celluzzi et al., *J. Exp. Med.* 83:283–287 (1996)).

The purities of ProGP-derived DC (100 µg/day, 10 days, SC) and GM-CSF/IL-4 ex vivo expanded DC were determined by flow cytometry. DC populations were defined as cells expressing both CD11c and MHC Class II molecules. Following purification of DC from magnetic CD11c microbeads, the percentage of double positive PB-derived DC, isolated from ProGP-treated mice, was enriched from approximately 4% to a range from 48–57% (average yield= 4.5×10$^6$ DC/animal). The percentage of purified splenic DC isolated from ProGP treated mice was enriched from a range of 12–17% to a range of 67–77%. The purity of GM-CSF/IL-4 ex vivo expanded DC ranged from 31–41% (Wong et al., *J. Immunother.*, 21:32040 (1998)).

In Vitro Stimulation of CTL Hybridomas and CTL Cell Lines:

Presentation of Specific CTL Epitopes

The ability of ProGP generated DC to stimulate a CTL cell line was demonstrated in vitro using a viral-derived epitope and a corresponding epitope responsive CTL cell line. Transgenic mice expressing human HLA-A2.1 were treated with ProGP. Splenic DC isolated from these mice were pulsed with a peptide epitope derived from hepatitis B virus (HBV Pol 455) and then incubated with a CTL cell line that responds to the HBV Pol 455 epitope/HLA-A2.1 complex by producing IFNγ. The capacity of ProGP-derived splenic DC to present the HBV Pol 455 epitope was greater than that of two positive control populations: GM-CSF and IL-4 expanded DC cultures, or purified splenic B cells (FIG. 3). The left shift in the response curve for ProGP-derived spleen cells versus the other antigen presenting cells reveal that these ProGP-derived cells require less epitope to stimulate maximal IFNγ release by the responder cell line.

Example 9

Peptide-pulsed ProGP-Derived DC Promote In vivo CTL responses

The ability of ex vivo peptide-pulsed DC to stimulate CTL responses in vivo was also evaluated using the HLA-A2.1 transgenic mouse model. DC derived from ProGP-treated animals or control DC derived from bone marrow cells after expansion with GM-CSF and IL-4 were pulsed ex vivo with the HBV Pol 455 CTL epitope, washed and injected (IV) into such mice. At seven days post immunization, spleens were removed and splenocytes containing DC and CTL were restimulated twice in vitro in the presence of the HBV Pol 455 peptide. The CTL activity of three independent cultures of restimulated spleen cell cultures was assessed by measuring the ability of the CTL to lyse $^{51}$Cr-labeled target cells pulsed with or without peptide. Vigorous CTL responses were generated in animals immunized with the epitope-pulsed ProGP derived DC as well as epitope-pulsed GM-CSF/IL-4 DC (FIG. 4). In contrast, animals that were immunized with mock-pulsed ProGP-generated DC (no peptide) exhibited no evidence of CTL induction. These data confirm that DC derived from ProGP treated mice can be pulsed ex vivo with epitope and used to induce specific CTL responses in vivo. Thus, these data support the principle that ProGP-derived DC promote CTL responses in a model that manifests human MHC Class I molecules.

In vivo pharmacology studies in mice have demonstrated no apparent toxicity of reinfusion of pulsed autologous DC into animals.

Example 10

Manufacturing of Synthetic Peptides:

Physical/Chemical Properties of the Bulk A2 Vaccine Peptides

In one embodiment, each peptide of the invention is prepared by chemical synthesis and is isolated as a solid by lyophilization. Peptides are manufactured in compliance with Good Manufacturing Practices.

Bulk peptides of the invention, following identity and release testing, are formulated as an aqueous or non-aqueous solution, sterile filtered, and aseptically filled into sterile, depyrogenated vials. Sterile rubber stoppers are inserted and overseals applied to the vials. The vialed formulations undergo 100% visual inspection and specified release testing. The released vials are labeled and packaged before delivery for administration.

Table 6 summarizes the identifying source number, the amino acid sequence, binding data, and properties of CTLs induced by each peptide.

Example 11

Dendritic Cell Isolation, Pulsing, Testing and Administration

A presently preferred procedure for vaccination is set forth herein. In brief, patients are treated with ProGP to expand and mobilize DC into the circulation. On the day of peak DC mobilization, determined in accordance with procedures known in the art, patients undergo leukapheresis (approximately 15 L process, possibly repeated once if required to collect sufficient mononuclear cells). The mononuclear cell product is admixed with peptides of the invention by injection through micropore filters (this admixing protocol is not needed if sterile peptides are used). After incubation and washing to remove residual unbound peptides, the cell product vaccine embodiment is resuspended in cryopreservative solution (final 10% DMSO) and, for those protocols involving multiple vaccination boosts, divided into aliquots. The pulsed mononuclear cell product (s) are frozen and stored according to accepted procedures for hematopoietic stem cells.

Vaccination is performed by injection or intravenous infusion of thawed cell product after the hematologic effects of ProGP in the patient have dissipated (i.e., the hemogram has returned to baseline). FIG. 5 provides a flow chart of ex vivo pulsing of DC with peptides, washing of DC, DC testing, and cryopreservation. A more detailed description of the process is provided in the following Examples.

Example 12

Administration of ProGP and Collection of Mononuclear Cells by Leukapheresis

Patients are treated with ProGP daily by subcutaneous injection (dose and schedule determined in accordance with standard medical procedures). On the evening before leukapheresis, patients are assessed by an apheresis physician or nurse/technologist for adequacy of intravenous access for large-bore apheresis catheters. If peripheral venous access is deemed inadequate to maintain rapid blood flow for apheresis, then central venous catheters (inguinal, subclavian or internal jugular sites) can be inserted by appropriate medical/surgical personnel. On the day of predicted peak DC mobilization, leukapheresis (approximately 3 blood volumes or 15 L) is performed, for example, on a Cobe Spectra or Fenwal CS3000 (flow rate≧35 mL/min) to obtain mononuclear cells. The number of DC in the leukapheresis product is estimated by flow cytometric counting of mononuclear cells possessing the immunophenotypes lin-/HLA-DR+/CD11c+ and lin-/HLA-DR+/CD123+ in a 1 mL sample aseptically withdrawn from the apheresis product. The numbers of granulocytes and lymphocytes in the leukapheresis product are counted by automated cytometry (CBC/differential). CBC/differential is performed immediately after the leukapheresis procedure and every other day for ten days to monitor resolution of the hematologic effects of the hematopoietin treatment and apheresis.

Example 13

A Procedure for Dendritic Cell Pulsing

Plasma is removed from the leukapheresis product by centrifugation and expression of supernatant. The cells from the centrifugation pellet are resuspended in OptiMEM medium with 1% Human Serum Albumin (HSA) at a cell density of $10^7$ DC/ml in up to 100 ml.

The peptide(s) of the invention, preferably as individual sterile A2 peptide formulations, are administered directly into the DC culture bag through an injection port, using aseptic technique. After mixing, e.g., by repeated squeezing and inversion, the cell suspension is incubated for four hours at ambient temperature. Cryopreservative solution is prepared by dissolving 50 mL pharmaceutical grade dimethylsulfoxide (DMSO) in 200 mL Plasmalyte®. After the pulsing period, the cell suspension is washed by centrifugation and resuspension in an equal volume of phosphate buffered saline solution. The washing procedure is repeated a defined number of times, e.g., until studies validate that peptides have been removed. Samples of one milliliter each are removed for viability testing and microbiological testing. The cells are then prepared for freezing by centrifugation and resuspension in an equal volume of cryopreservative solution (final 10% DMSO). The cell suspension in cryopreservative is then divided into six equal aliquots, transferred to 50 ml freezing bags (Fenwal) and frozen at controlled rate of 1° C./min for storage in liquid nitrogen until needed for vaccination procedure.

Assay to Evaluate the Pulsing Procedure

Antigen presenting cells, long-term stimulated T cells corresponding to peptides of the invention, or T cell hybridomas, are used to determine the optimal procedure for incubating the peptide reagents of a vaccine with human cells. Pulsing studies are done using one or more of the following cell sources: purified DC from ProGP treated HLA- A2.1 transgenic mice; human tumor cell lines that express HLA-A2; peripheral blood mononuclear cells from normal human volunteers; peripheral blood mononuclear cells from ProGP treated patients; and/or DC obtained from normal human HLA-A2 volunteers following the ex vivo culture of their peripheral blood mononuclear cells with GM-CSF and IL-4.

Evaluated conditions include, e.g.:

A. Cellular isolation procedure and cell number

B. Concentration of vaccine peptides

C. Washing conditions to remove ancillary reagents

D. Post-pulsing manipulations (resuspension, freezing)

Accordingly, these studies demonstrate the ability of the procedure to produce functional HLA-A2/peptide complexes on the surface of the human cells. The validation of the pulsing procedure is established using HLA-A2.1-specific T cell lines after which the Phase I clinical trial occurs.

Example 14

Validation of Peptide Removal from the DC Product

Following pulsing with the peptide reagents, DC from the patient are washed several times to remove excess peptides prior to infusing the cells back into the patient. In this embodiment of a vaccine of the invention, the washing procedure removes unbound peptides. Accordingly, there is no, or negligible, systemic exposure of the patient to the peptides. Alternative vaccines of the invention involve direct administration of peptides of the invention to a patient, administration of a multiepitopic polypeptide comprising one or more peptides of the invention, administration of the peptides in a form of nucleic acids which encode them, e.g., by use of minigene constructs.

Assay for Vaccine Peptides in the Dendritic Cell Wash Buffer

After the DC are incubated with the peptides, the cells are washed with multiple volumes of wash buffer. An aliquot of the last wash is placed onto a nonpolar solid-phase extraction cartridge and washed to reduce the salt content of the sample. Any peptides contained in the buffer will be eluted from the extraction cartridge and evaporated to dryness. The sample is then reconstituted in High Performance Liquid Chromatography (HPLC) mobile phase, injected onto a polymer based reverse-phase HPLC column, and eluted using reverse-phase gradient elution chromatography. Residual peptides are detected using a mass spectrometer set-up to monitor the protonated molecular ions of each peptide as they elute from the HPLC column. The peptides are quantified by comparing the area response ratio of analyte and internal standard to that obtained for standards in a calibration curve.

Example 15

Validation of Trifluoroacetic Acid Removal from the DC Product

In a particular embodiment, peptide reagents may be formulated using 0.1% trifluoroacetic acid (TFA). The washing procedure developed to remove residual peptide also removes residual TFA.

Example 16

Dendritic Cell Release Testing

Identity

The number of DC in the leukapheresis product is estimated by flow cytometric counting of mononuclear cells possessing the immunophenotypes $lin^-/HLA-DR^+/CD11c^+$ and $lin^-/HLA-DR^+/CD123^+$ in a 1 ml sample aseptically withdrawn from the apheresis product. $Lin^-$ cells excludes monocytes, T-lymphocytes, B-lymphocytes, and granulocytes, by using a cocktail of antibodies to lineage markers CD3, CD14, DC16, CD19, CD20, CD56.

Cell Viability

Viability of mononuclear cells is assessed after pulsing and washing, prior to suspension in cryopreservative, by trypan blue dye exclusion. In general, if the cell product contains more than 50% trypan blue-positive cells, the product is not administered to a patient.

Microbiological Testing

The cell suspension in cryopreservative is examined for microbial contamination by gram stain and routine clinical bacterial and fungal culture/sensitivity. If tests are positive for bacterial or fingal contamination, implicit evidence of significant contamination, the product is not infused. If, e.g., a gram stain is negative, the product may be infused for the first vaccination while awaiting results of culture/sensitivity. Antibiotic therapy based on culture results is instituted at the discretion of the treating physician if the patient shows appropriate signs of infection that could be clinically attributable to the infused contaminant.

Example 17

Patient Vaccination

In a preferred embodiment, an aliquot of frozen pulsed dendritic cell product is removed from a liquid nitrogen freezer and kept frozen in an insulated vessel containing liquid nitrogen during transport to the infusion site. The product is thawed by immersion with gentle agitation in a water bath at 37° C. Immediately on thawing, the cell suspension is infused through intravenous line by gravity or by syringe pump. Alternatively, the vaccine is administered by injection, e.g., subcutaneously, intradermally, or intramuscularly. The patient's vital signs are monitored before infusion/injection and at 5 minute intervals during an infusion, then at 15 minute intervals for 1 hour after infusion/injection.

Infusion protocols in accordance with knowledge in the art are carried out for alternative vaccine embodiments of the invention, such as direct peptide infusion or nucleic acid administration.

Example 18

An A2 Vaccine

A vaccine in accordance with the invention comprises eight peptide epitopes bearing the HLA-A2 supermotif. Collectively, these eight epitopes are derived from the tumor associated antigens (TAAs) HER2/neu, p53, MAGE 2, MAGE3, and carcinoembryonic antigen (CEA), and stimulate CTL responses to these TAAs. (see Table 9) These eight peptides, which are also presented in Table 6, bear an HLA-A2 supermotif. Optionally, a ninth peptide, an HTL epitope that enhances CTL responses such as a pan-DR-binding peptide (PADRE™, Epimmune, San Diego, Calif.), is included.

The eight HLA-A2 peptide components of the A2 vaccine bind to multiple HLA-A2 superfamily molecules with high or intermediate affinity ($IC_{50} \leq 500$ nM). HLA-A2-specific analog and native peptide components of the A2 vaccine stimulate CTL from the peripheral blood of normal human volunteers. These CTL recognize native peptides that have been pulsed onto HLA-A2 expressing APCs, as well as endogenous peptides presented by HLA-matched tumor cell lines. Thus, the A2 vaccine is effective in stimulating the cellular arm of the immune system to mediate immune responses against tumors.

It is to be appreciated that vaccines comprising peptides bearing other motifs, or nucleic acids encoding such peptides, are also used in accordance with the principles set forth herein, and are within the scope of the present invention.

In a preferred embodiment, an A2 vaccine comprises DC pulsed ex vivo with the nine peptides. This embodiment of a vaccine can be used with progenipoietin (ProGP)-mobilized DC.

Example 19

An A2 Vaccine

An A2 vaccine comprises a cocktail of 12 peptides, 10 of which stimulate CTL responses to the tumor associated antigens (TAA) HER2/neu, p53, MAGE 2/3, and carcinoembryonic antigen (CEA). The remaining two peptides are both members of the PADRE® family of peptides that are HTL epitopes that enhance CTL responses (see Table 10). This embodiment of an A2 Vaccine is used in combination with an emulsion-based adjuvant such as Montanide® ISA51 or ISA720 (Seppic, Paris, France) or an Incomplete Freund's Adjuvant, preferably administered by injection. As appreciated by those of skill in the art, alternative modes of administration can also be used. Many adjuvants are known in the art, and are used in accordance with the present invention, see, e.g., Tomlinson, et al., Advanced Drug Delivery Reviews, Vol. 32(3) (Jul. 6, 1998).

The eight HLA-A2 CTL peptide components of this vaccine embodiment bind to multiple HLA-A2 superfamily molecules with high or intermediate affinity ($IC_{50} \leq 500$ nM). The HLA-A2-specific analog and native peptide components of the present vaccine stimulate CTL from patient's blood. These CTL recognize native peptides that were pulsed onto HLA-A2 expressing APCs, as well as endogenous peptides presented by HLA-matched tumor cell lines.

Two peptides that stimulate HLA class II are also used in accordance with the invention. For instance, a pan-DR-binding epitope peptide having the formula: aKXVAAZTLKAAa, where "X" is either cyclohexylalanine, phenylalanine, or tyrosine; "Z" is either tryptophan, tyrosine, histidine or asparagine; and "a" is either D-alanine or L-alanine, has been found to bind to most HLA-DR alleles, and to stimulate the response of T helper lymphocytes from most individuals, regardless of their HLA type. Two particularly preferred PADRE® molecules are the peptides, aKFVAAYTLKAAa-$NH_2$ and aKXVAAHTLKAAa-$NH_2$ (a=D-alanine, X=cyclohexylalanine), the latter containing a non-natural amino acid, specifically engineered to maximize both HLA-DR binding capacity and induction of T cell immune responses.

The PADRE® peptide components of the A2 vaccine bind with high affinity and broad specificity to multiple allelic forms of HLA-DR molecules ($IC_{50} \pounds 1000$ nM). The in vivo administration of PADRE® peptide stimulates the proliferation of HTL in normal humans as well as patient populations. Thus, this vaccine embodiment is effective in stimulating the cellular arm of the immune system to mediate immune responses against tumors.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 1

Overview of current cancer vaccine approaches.

| APPROACH | DESCRIPTION | ISSUES | STRENGTHS |
| --- | --- | --- | --- |
| Whole Cell Vaccines | Involve the administration of whole cancer cells with adjuvants which serve to potentiate the immune response | Often difficult to obtain tumor cells Patient variability Single patient product Has relatively low concentration of relevant TAA epitopes | Likely to have novel TAA |
| Cell Lysate Vaccines | Consist of lysed allogeneic cancer cell membrane particles that are ingested by macrophages and presented as tumor antigens to effector cells | Often difficult to obtain tumor cells Patient variability Single patient product Has relatively low concentration of | Likely to have novel TAA |

TABLE 1-continued

Overview of current cancer vaccine approaches.

| APPROACH | DESCRIPTION | ISSUES | STRENGTHS |
|---|---|---|---|
| Idiotypic Vaccines | Contain proteins derived from individual patient tumors or from specific tumor types | relevant TAA epitopes<br>Often difficult to obtain tumor cells<br>Patient variability<br>Single patient product<br>Has relatively low concentration of relevant TAA epitopes | Specific TAA |
| Whole Antigen Vaccines | | Limited disease coverage<br>Difficult to break tolerance | Complex "natural" immune responses may be elicited<br>Relatively easy single compound manufacture |
| Viral oncolysate vaccines | Consist of vaccinia virus infected cancer cell, lysed to form membrane segments expressing both vaccinia and cancer cell antigens | Often difficult to obtain tumor cells<br><br>Not always possible to infect cancer cells<br>Patient specific treatment<br>Has relatively low concentration of relevant TAA epitopes | |
| Shed antigen vaccines | Similar to whole cell and lysate vaccines but are partially purified | Difficult to purify antigens<br>Patient specific treatment<br>Has relatively low concentration of relevant TAA epitopes | Likely to have novel TAA |
| Genetically modified tumor cell vaccines | A number of avenues are being explored including the transduction of cells with GM-CSF | Very difficult to obtain tumor tissues and grow to allow stable transduction<br>Patient specific treatment | Cells contain novel TAA and adjuvants |
| Peptide Vaccines | Synthetic peptides are produced that correspond to tumor associated antigens. Designed to stimulate a cytotoxic T-Cell response (CTL) | Need to choose correct peptides to elicit an effective immune response<br>Restriction to HLA subtype or HLA supertypes | Single preparation used for multiple patients and possibly multiple diseases<br>Possible to combine various antigens/targets<br>Reproducible antigen production<br>Able to break tolerance<br>Able to elicit responses to subdominant epitopes<br>Can be directed to supertypes for broad population coverage |
| Carbohydrate vaccines | Synthetically produced tumor associated carbohydrates, designed to stimulate an | May need CTL response as well as humoral response | Single preparation used for |

TABLE 1-continued

Overview of current cancer vaccine approaches.

| APPROACH | DESCRIPTION | ISSUES | STRENGTHS |
|---|---|---|---|
| | antibody response against the carbohydrate antigens | Carbohydrate antigens are HTL dependent | multiple patients and possibly multiple diseases |

TABLE 2

| | POSITION 2 (Primary Anchor) | POSITION 3 (Primary Anchor) | POSITION C-terminus (Primary Anchor) |
|---|---|---|---|
| SUPERMOTIFS | | | |
| A1 | T*IL*VMS | | FWY |
| A2 | LIVM*ATQ* | | IVM*ATL* |
| A3 | VSMA*TLI* | | RK |
| A24 | YF*WIVLMT* | | FI*YWLM* |
| B7 | P | | VILF*MWYA* |
| B27 | RHK | | FYL*WMIVA* |
| B44 | E*D* | | FWYLIMVA |
| B58 | ATS | | FWY*LIVMA* |
| B62 | QL*IVMP* | | FWY*MIVLA* |
| MOTIFS | | | |
| A1 | TSM | | Y |
| A1 | | DEA*S* | Y |
| A2.1 | LM*VQIAT* | | V*LIMAT* |
| A3 | LMVISATF*CGD* | | KYR*HFA* |
| A11 | VTMLISAGN*CDF* | | K*RYH* |
| A24 | YF*WM* | | FLIW |
| A*3101 | MVT*ALIS* | | R*K* |
| A*3301 | MVALF*IST* | | RK |
| A*6801 | AVT*MSLI* | | RK |
| B*0702 | P | | LMF*WYAIV* |
| B*3501 | P | | LMFWY*IVA* |
| B51 | P | | LIVF*WYAM* |
| B*5301 | P | | IMFWY*ALV* |
| B*5401 | P | | ATIV*LMFWY* |

Bolded residues are preferred, italicized residues are less preferred: A peptide is considered motif-bearing if it has primary anchors at each primary anchor position for a motif or supermotif as specified in the above table.

TABLE 2A

| | POSITION 2 (Primary Anchor) | POSITION 3 (Primary Anchor) | POSITION C Terminus (Primary Anchor) |
|---|---|---|---|
| SUPERMOTIFS | | | |
| A1 | T*IL*VMS | | FWY |
| A2 | VQAT | | V*LIMAT* |
| A3 | VSMA*TLI* | | RK |
| A24 | YF*WIVLMT* | | FI*YWLM* |
| B7 | P | | VILF*MWYA* |
| B27 | RHK | | FYL*WMIVA* |
| B58 | ATS | | FWY*LIVMA* |
| B62 | QL*IVMP* | | FWY*MIVLA* |
| MOTIFS | | | |
| A1 | TSM | | Y |
| A1 | | DEA*S* | Y |
| A2.1 | VQAT* | | V*LIMAT* |
| A3.2 | LMVISATF*CGD* | | KYR*HFA* |
| A11 | VTMLISAGN*CDF* | | KR*HY* |
| A24 | YFW | | FLIW |

*If position 2 is V, or Q, the C-terminal amino acid of the epitope is not L.

Bolded residues are preferred, italicized residues are less preferred. A peptide is considered motif-bearing if it has amino acids at each primary anchor position for a motif or supermotif as specified in the above table.

TABLE 3

| | | 1° anchor 1 | 2 | 3 | 4 | 1° anchor 4 | 5 | 1° anchor 6 | 7 | 8 | 9 | |
|---|---|---|---|---|---|---|---|---|---|---|---|---|
| MOTIFS | | | | | | | | | | | | | |
| DR4 | preferred | FMY*LIVW* | M | T | | | I | | VST*CPALIM* | MH R | | MH WDE | |
| | deleterious | | | W | | | | | | | | AVM | |
| DR1 | preferred | MF*LIVWY* | | | PAMQ | | | | VMAT*SPLIC* | M | | | |
| | deleterious | | C, | CH | FD | | CWD | | | GDE | D | | |
| DR7 | preferred | MF*LIVWY* | M | W | A | | | | IVMSAC*TPL* | M | | IV | SEQ ID NO:51 |
| | deleterious | | C | | G | | | | | GRD | N | G | SEQ ID NO:52 |
| DR Supermotif | | MF*LIVWY* | | | | | | | VMSTA*CPLI* | | | | |
| DR3 MOTIFS | | | | | | | | | | | | | |
| motif a preferred | | LIVMFY | | | | | D | | | | | | |

TABLE 3-continued

| | POSITION | | | | | | | | |
|---|---|---|---|---|---|---|---|---|---|
| | 1° anchor 1 | 2 | 3 | 4 | 1° anchor 4 | 5 | 1° anchor 6 | 7 | 8 | 9 |
| motif b preferred | LIVMFAY | | | | DNQEST | | KRH | | | |

Italicized residues indicate less preferred or "tolerated" residues.

TABLE 4

HLA Class I Standard Peptide Binding Affinity.

| ALLELE | STANDARD PEPTIDE | SEQUENCE | SEQ ID NO: | STANDARD BINDING AFFINITY (nM) |
|---|---|---|---|---|
| A*0101 | 944.02 | YLEPAIAKY | 42 | 25 |
| A*0201 | 941.01 | FLPSDYFPSV | 43 | 5.0 |
| A*0202 | 941.01 | FLPSDYFPSV | 43 | 4.3 |
| A*0203 | 941.01 | FLPSDYFPSV | 43 | 10 |
| A*0205 | 941.01 | FLPSDYFPSV | 43 | 4.3 |
| A*0206 | 941.01 | FLPSDYFPSV | 43 | 3.7 |
| A*0207 | 941.01 | FLPSDYFPSV | 43 | 23 |
| A*6802 | 1072.34 | YVIKVSARV | 44 | 8.0 |
| A*0301 | 941.12 | KVFPYALINK | 45 | 11 |
| A*1101 | 940.06 | AVDLYHFLK | 46 | 6.0 |
| A*3101 | 941.12 | KVFPYALINK | 45 | 18 |
| A*3301 | 1083.02 | STLPETYVVRR | 47 | 29 |
| A*6801 | 941.12 | KVFPYALINK | 45 | 8.0 |
| A*2402 | 979.02 | AYIDNYNKF | 48 | 12 |
| B*0702 | 1075.23 | APRTLVYLL | 49 | 5.5 |
| B*3501 | 1021.05 | FPFKYAAAF | 50 | 7.2 |
| B51 | 1021.05 | FPFKYAAAF | 50 | 5.5 |
| B*5301 | 1021.05 | FPFKYAAAF | 50 | 9.3 |
| B*5401 | 1021.05 | FPFKYAAAF | 50 | 10 |

TABLE 5

HLA Class II Standard Peptide Binding Affinity.

| Allele | Nomenclature | Standard Peptide | Sequence | SEQ ID NO: | Binding Affinity (nM) |
|---|---|---|---|---|---|
| DRB1*0101 | DR1 | 515.01 | PKYVKQNTLKLAT | 51 | 5.0 |
| DRB1*0301 | DR3 | 829.02 | YKTIAFDEEARR | 52 | 300 |
| DRB1*0401 | DR4w4 | 515.01 | PKYVKQNTLKLAT | 51 | 45 |
| DRB1*0404 | DR4w14 | 717.01 | YARFQSQTTLKQKT | 53 | 50 |
| DRB1*0405 | DR4w15 | 717.01 | YARFQSQTTLKQKT | 53 | 38 |
| DRB1*0701 | DR7 | 553.01 | QYIKANSKFIGITE | 38 | 25 |
| DRB1*0802 | DR8w2 | 553.01 | QYIKANSKFIGITE | 38 | 49 |
| DRB1*0803 | DR8w3 | 553.01 | QYIKANSKFIGITE | 38 | 1600 |
| DRB1*0901 | DR9 | 553.01 | QYIKANSKFIGITE | 38 | 75 |
| DRB1*1101 | DR5w11 | 553.01 | QYIKANSKFIGITE | 38 | 20 |
| DRB1*1201 | DR5w12 | 1200.05 | EALIHQLKINPYVLS | 54 | 298 |
| DRB1*1302 | DR6w19 | 650.22 | QYIKANAKFIGITE | 38 | 3.5 |
| DRB1*1501 | DR2w2β1 | 507.02 | GRTQDENPVVHFFK NIVTPRTPPP | 55 | 9.1 |
| DRB3*0101 | DR52a | 511 | NGQIGNDPNRDIL | 56 | 470 |
| DRB4*0101 | DRw53 | 717.01 | YARFQSQTTLKQKT | 53 | 58 |
| DRB5*0101 | DR2w2β2 | 553.01 | QYIKANSKFIGITE | 58 | 20 |

TABLE 6

Identified CFL Epitopes for an A2 Vaccine

| Source | Sequence | SEQ ID NO: | A* 0201 | A* 0202 | A* 0203 | A* 0206 | A* 6802 | No. A2 Alleles Bound | CTL[1] Seq. | Wild-type Seq. | Tumor |
|---|---|---|---|---|---|---|---|---|---|---|---|
| CEA.24V9 | LLTFWNPPV | 22 | 16 | 307 | 26 | 56 | 952 | 4 | 1/1 | TBD[2] | 1/1 |
| CEA.233V10 | VLYGPDAPTV | 9 | 26 | 430 | 16 | 206 | 952 | 4 | 3/4 | 2/2 | 1/4 |
| CEA.605V9 | YLSGANLNV | 1 | 73 | 13 | 13 | 80 | 1600 | 4 | 4/4 | ¾ | 1/4 |
| CEA.687 | ATVGIMIGV | 10 | 36 | 8.8 | 20 | 11 | 0.80 | 5 | 1/1 | 1/1 | 1/1 |
| CEA.691 | IMIGVLVGV | 2 | 69 | 62 | 13 | 106 | 89 | 5 | 8/8 | 8/8 | 4/7 |
| p53.25V11 | LLPENNVLSPV | 11 | 38 | 4 | 4 | 9 | 30 | 5 | 2/3 | 1/3 | 1/3 |
| p53A39L2 | KLCPVQLWV | 12 | 122 | 239 | 29 | 23 | —[3] | 4 | 2/5 | 2/3 | 1/3 |
| p53.139L2B3 | KLBPVQLWV | 3 | 34 | 8.7 | 20 | 11 | — | 4 | 3/4 | 2/3 | 1/2 |
| p53.149L2 | SLPPPGTRV | 13 | 122 | 226 | 13 | 9250 | 140 | 4 | 2/3 | 1/3 | 0/3 |
| p53.149M2 | SMPPPGTRV | 4 | 172 | 215 | 13 | 425 | 667 | 4 | 2/4 | 2/4 | 2/4 |
| Her2/neu.5 | ALCRWGLLL | 17 | 100 | —[2] | 278 | — | — | 2 | 2/2 | 2/2 | 2/2 |
| Her2/neu.48 | HLYQGCQVV | 19 | 139 | 307 | 13 | 514 | 1143 | 3 | 3/4 | ¾ | 1/3 |
| Her2/neu.369 | KIFGSLAFL | 21 | 36 | 9 | 19 | 23 | 3333 | 4 | 10/11 | 10/11 | 7/11 |
| Her2/neu.369L2V9 | KLFGSLAFV | 14 | 5.8 | 7.5 | 19 | 17 | 1270 | 4 | 4/4 | ¾ | 2/4 |
| Her2/neu.369V2V9 | KVFGSLAFV | 15 | 20 | 19 | 769 | 15 | 29 | 4 | 4/4 | ¾ | 2/4 |
| Her2/neu.435 | ILHNGAYSL | 20 | 75 | 358 | 100 | 569 | — | 3 | 5/5 | 5/5 | 3/5 |
| Her2/neu.665 | VVLGVVFGI | 8 | 14 | — | 2500 | 430 | 2000 | 2 | 4/8 | 4/8 | 1/1 |
| Her2/neu.689 | RLLQETELV | 7 | 21 | — | 625 | 34 | — | 2 | 4/8 | 4/8 | 1/1 |
| Her2/neu.773 | VMAGVGSPYV | 16 | 200 | 391 | 13 | 3700 | — | 3 | 2/4 | 2/4 | 1/4 |
| Her2/neu.952 | YMIMVKCWMI | 25 | 20 | 307 | 83 | 116 | 267 | 5 | 2/3 | 2/3 | 2/3 |
| MAGE2.157 | YLQLVFGIEV | 6 | 50 | 165 | 345 | 370 | 9302 | 4 | 3/3 | 3/3 | 1/3 |
| MAGE3.159 | QLVFGIELMEV | 24 | 7.9 | 74 | 217 | 185 | 267 | 5 | 3/3 | 3/3 | 1/3 |
| MAGE3.112 | KVAELVHFL | 5 | 69 | 29 | 14 | 168 | 17 | 5 | 3/4 | ¾ | 3/4 |
| MAGE3.160 | LVFGIELMEV | 23 | 29 | 20 | 7.7 | 28 | 14 | 5 | 4/4 | 4/4 | 1/4 |
| MAGE3.271 | FLWGPRALV | 18 | 31 | 43 | 14 | 336 | 40 | 5 | 4/4 | 4/4 | 2/4 |

[1]) Number of donors yielding a positive response/total tested.
[2]) To be determined
[3]) — indicates binding affinity ≦ 10,000 nM.
[4]) For peptides that are not analogs, "Sequence" and "Wild-type Sequence" provide the same information

TABLE 7

Expression of Tumor Associated Antigen (TAA)

| | % of Tumors Expressing the TAA | | |
|---|---|---|---|
| TAA | Colon Cancer | Breast Cancer | Lung Cancer |
| CEA | 95 | 50 | 70 |
| P53 | 50 | 50 | 40–60 |
| MAGE 2/3 | 20–30 | 20–30 | 35 |
| HER2/neu | 28–50 | 30–50 | 20–30 |
| Total | 99 | 86–91 | 91–95 |

TABLE 8

Incidence and survival rate of patients with breast, colon, or lung cancer in the United States

| | Estimated New Cases | Estimate Deaths | 5-Year relative survival rates | | |
|---|---|---|---|---|---|
| | 1998 | 1998 | 1974–76 | 1980–82 | 1986–1993 |
| Breast | 180,300 | 43,900 | 75% | 77% | 80% |
| Colon | 95,600 | 47,700 | 50% | 56% | 63% |
| Lung | 171,500 | 160,100 | 12% | 14% | 14% |

Source: Cancer Statistics 1998. January/February 1998, Vol. 48, No. 1

TABLE 9

Summary of CTL Epitopes for an A2 Vaccine

| Epitope[1] | Sequence | SEQ ID NO: | A* 0201 $IC_{50}$ $(nM)^2$ | A* 0202 $IC_{50}$ $(nM)^2$ | A* 0203 $IC_{50}$ $(nM)^2$ | A* 0206 $IC_{50}$ $(nM)^2$ | A* 6802 $IC_{50}$ $(nM)^2$ | No. A2 Members Cross-bound | CTL Recognition Native Pulsed Cells | Tumor Cell |
|---|---|---|---|---|---|---|---|---|---|---|
| CEA.605V9 | YLSGANLNV | 1 | 73[3] | 13 | 13 | 80 | 1600 | 4 | + | + |
| CEA.691 | IMIGVLVGV | 2 | 69 | 62 | 13 | 106 | 89 | 5 | + | + |
| p53.139L2B3 | KLBPVQLWV | 3 | 34 | 8.7 | 20 | 11 | —[4] | 4 | + | + |

TABLE 9-continued

Summary of CTL Epitopes for an A2 Vaccine

| Epitope[1] | Sequence | SEQ ID NO: | A* 0201 IC$_{50}$ (nM)[2] | A* 0202 IC$_{50}$ (nM)[2] | A* 0203 IC$_{50}$ (nM)[2] | A* 0206 IC$_{50}$ (nM)[2] | A* 6802 IC$_{50}$ (nM)[2] | No. A2 Members Cross-bound | CTL Recognition Native Pulsed Cells | Tumor Cell |
|---|---|---|---|---|---|---|---|---|---|---|
| p53.149M2 | SMPPPGTRV | 4 | 172 | 215 | 13 | 425 | 667 | 4 | + | + |
| MAGE3.112 | KVAELVHFL | 5 | 69 | 29 | 14 | 168 | 17 | 5 | + | + |
| MAGE2.157 | YLQLVFGIEV | 6 | 50 | 165 | 345 | 370 | 9302 | 4 | + | + |
| HER2/neu.689 | RLLQETELV | 7 | 21 | — | 625 | 34 | — | 2 | + | + |
| HER2/neu.665 | VVLGVVFGI | 8 | 14 | — | 2500 | 430 | 2000 | 2 | N.D. | + |

[1]) The peptide designations are derived from the target antigen (e.g. CEA) and the numeral relates to the first amino acid in the protein (e.g. 691). Analogs are noted by the amino acid inserted by substitution and the peptide position substituted (e.g. V9).
[2]) HLA binding was measured by a competitive binding assay where lower values indicate greater binding affinity.
[3]) Standard errors corresponding to HLA binding were presented in previous figures.
[4]) (—) indicates binding affinity > 10,000 nM.

TABLE 10

Identified CTL Epitopes for an A2 Vaccine

| | | | HLA-A2 Binding Affinity (IC50 nM) | | | | | | CTL[1] | | |
|---|---|---|---|---|---|---|---|---|---|---|---|
| Source | Sequence | SEQ ID NO: | A* 0201 | A* 0202 | A* 0203 | A* 0206 | A* 6802 | No. A2 Alleles Bound | Seq. | Wild-type Seq. | Tumor |
| CEA.24V9 | LLTFWNPPV | 22 | 16 | 307 | 26 | 56 | 952 | 4 | 1/1 | TBD[2] | 1/1 |
| CEA.233V10 | VLYGPDAPTV | 9 | 26 | 430 | 16 | 206 | 952 | 4 | 3/4 | 2/2 | 1/4 |
| CEA.687 | ATVGIMIGV | 10 | 36 | 8.8 | 20 | 11 | 0.80 | 5 | 1/1 | 1/1 | 1/1 |
| P53.25V11 | LLPENNVLSPV | 11 | 38 | 4 | 4 | 9 | 30 | 5 | 2/3 | 1/3 | 1/3 |
| P53.139L2 | KLCPVQLWV | 12 | 122 | 239 | 29 | 23 | —[3] | 4 | 2/5 | 2/3 | 1/3 |
| Her2/neu.369 | KIFGSLAFL | 21 | 36 | 9 | 19 | 23 | 3333 | 4 | 10/11 | 10/11 | 7/11 |
| Her2/neu.369V2V9 | KVFGSLAFV | 15 | 20 | 19 | 769 | 15 | 29 | 4 | 4/4 | 3/4 | 2/4 |
| Her2/neu.952 | YMIMVKCWMI | 25 | 20 | 307 | 83 | 116 | 267 | 5 | 2/3 | 2/3 | 2/3 |
| MAGE3.159 | QLVFGIELMEV | 24 | 7.9 | 74 | 217 | 185 | 267 | 5 | 3/3 | 3/3 | 1/3 |
| MAGE3.160 | LVFGIELMEV | 23 | 29 | 20 | 7.7 | 28 | 14 | 5 | 4/4 | 4/4 | 1/4 |

[1]) Number of donors yielding a positive response/total tested.
[2]) To be determined
[3]) — indicates binding affinity ≤ 10,000 nM
[4]) For peptides that are not analogs, "Sequence" and "Wild-type Sequence" provide the same information

TABLE 11

Population coverage by HLA class I supertype epitopes.

| | | Minimal Allelic Frequency | | | | | |
|---|---|---|---|---|---|---|---|
| Supertype | Representative HLA Molecules* | Caucasian | Black | Japanese | Chinese | Hispanic | Average |
| A2 | 2.1, 2.2, 2.3, 2.5, 2.6, 2.7, 68.02 | 45.8 | 39.0 | 42.4 | 45.9 | 43.0 | 43.2 |
| A3 | 3, 11, 31, 33, 68.01 | 37.5 | 42.1 | 45.8 | 52.7 | 43.1 | 44.2 |
| B7 | 7, 51, 53, 35, 54 | 43.2 | 55.1 | 57.1 | 43.0 | 49.3 | 49.5 |
| Total Population Coverage | | 84.3 | 86.8 | 89.5 | 89.8 | 86.8 | 87.4 |

For A2, all A2 subtypes were included; for A3, the five listed allotypes were used; for B7, several additional allotypes were included based on binding pocket analysis.

TABLE 12

Tumor Associated Antigens and Genes (TAA)

| ANTIGEN | REFERENCE |
| --- | --- |
| MAGE 1 | (Traversari C., Boon T, J. Ex. Med 176:1453, 1992) |
| MAGE 2 | (De Smet C., Boon T, Immunogenetics, 39(2)121–9, 1994) |
| MAGE 3 | (Gaugler B., Boon T, J. Ex. Med 179: 921, 1994) |
| MAGE-11 | (Jurk M., Winnacker L, Int. J. Cancer 75, 762–766, 1998) |
| MAGE-A10 | (Huang L., Van Pel A, J. Immunology, 162:6849–6854) |
| BAGE | (Boel P., Bruggen V, Immunity 2:167, 1995) |
| GAGE | (Eynde V., Boon T, J. Exp. Med 182:689, 1995) |
| RAGE | (Gaugler B., Eynde V, Immunogenetics, 44:325, 1996) |
| MAGE-C1 | (Lucas S., Boon T, Cancer Research, 58, 743–752, 1998) |
| LAGE-1 | (Lethel B., Boon T, Int J cancer, 10; 76(6) 903–908 |
| CAG-3 | (Wang R--Rosenberg S, J. Immunology, 161:3591–3596, 1998) |
| DAM | (Fleischhauer K., Traversari C, Cancer Research, 58, 14, 2969, 1998) |
| MUC1 | (Karanikas V., McKenzie IF, J. clnical investigation, 100:11, 1–10, 1997) |
| MUC2 | (Bohm C., Hanski, Int. J. Cancer 75, 688–693, 1998) |
| MUC18 | (Putz E., Pantel K, Cancer Res 59(1):241–248, 1999) |
| NY-ES0-1 | (Chen Y., Old LJ PNAS, 94, 1914–18, 1997) |
| MUM-1 | (Coulie P., Boon T, PNAS 92:7976, 1995) |
| CDK4 | (Wolfel T., Beach D, Science 269:1281, 1995) |
| BRCA2 | (Wooster R---Stratton M, Nature, 378, 789–791, 1995) |
| NY-LU-1 | (Gure A., Chen, Cancer Research, 58, 1034–41, 1998) |
| NY-LU-7 | (Gure A., Chen, Cancer Research, 58, 1034–41, 1998) |
| NY-LU-12 | (Gure A., Chen, Cancer Research, 58, 1034–41, 1998) |
| CASP8 | (Mandruzzato S., Bruggen P, J. Ex. Med 186, 5, 785–793, 1997) |
| RAS | (Sidransky D., Vogelstein B, Science, 256:102) |
| KIAA0205 | (Gueguen M., Eynde, J. Immunology, 160:6188–94, 1998) |
| SCCs | (Molina R., Ballesta AM, Tumor Biol, 17(2):81–9, 1996) |
| p53 | (Hollstein M., Harris CC, Science, 253, 49–53, 1991) |
| p73 | (Kaghad M., Caput D, Cell; 90(4):809–19, 1997) |
| CEA | (Muraro R., Schlom J, Cancer Research, 45:5769–55780, 1985) |
| Her 2/neu | (Disis M., Cheever M, Cancer Res 54:1071, 1994) |
| Melan-A | (Coulie P., Boon T, J. Ex. Med, 180:35, 1994) |
| gp100 | (Bakker A., Figdor, J. Ex. Med 179:1005, 1994) |
| Tyrosinase | (Wolfel T., Boon T, E.J.I 24:759, 1994) |
| TRP2 | (Wang R., Rosenberg S.A, J. Ex. Med 184:2207, 1996) |
| gp75/TRP1 | (Wang R., Rosenberg S.A, J. Ex. Med 183:1131, 1996) |
| PSM | (Pinto J.T., Heston W.D.W., Clin Cancer Res 2(9); 1445–1451, 1996) |
| PSA | (Correale P., Tsang K, J. Natl cancer institute, 89:293–300, 1997) |
| PT1-1 | (Sun Y., Fisher PB, Cancer Research, 57(1):18–23, 1997) |
| B-catenin | (Robbins P., Rosenberg SA, J. Ex. Med 183:1185, 1996) |
| PRAME | (Neumann E., Seliger B, Cancer Research, 58, 4090–4095, 1998) |
| Telomearse | (Kishimoto K., Okamoto E, J Surg Oncol, 69(3): 119–124, 1998) |
| FAK | (Kornberg LJ, Head Neck, 20(8):745–52, 1998) |
| Tn antigen | (Wang B1, J Submicrosc Cytol Path, 30(4):503–509, 1998) |
| cyclin D1 protein | (Linggui K., Yaowu Z, Cancer Lett 130(1–2), 93–101, 1998) |
| NOEY2 | (Yu Y., Bat RC, PNAS, 96(1):214–219, 1999) |
| EGF-R | (Biesterfeld S.---- Cancer Weekly, Feb. 15, 1999) |
| SART-1 | (Matsumoto H., Itoh K, Japanese Journal of Cancer Research, 59, iss 12, 1292–1295, 1998) |
| CAPB | (Cancer Weekly, March 29, 4–5, 1999) |
| HPVE7 | (Rosenberg S.A. Immunity, 10, 282–287, 1999) |
| p15 | (Rosenberg S.A., Immunity, 10, 282–287, 1999) |
| Folate receptor | (Gruner B.A., Weitman S.D., Investigational New Drugs, Vol 16, iss 3, 205–219, 1998) |
| CDC27 | (Wang R.F., Rosenberg SA, Science, vol 284, 1351–1354, 1999) |
| PAGE-1 | (Chen, J. Biol. Chem: 273:17618–17625, 1998) |
| PAGE-4 | (Brinkmann: PNAS, 95:10757, 1998) |
| Kallikrein 2 | (Darson:Urology, 49:857–862, 1997) |
| PSCA | (Reiter R., PNAS, 95:1735–1740, 1998) |
| DD3 | (Bussemakers M.J.G, European Urology, 35:408–412, 1999) |
| RBP-1 | (Takahashi T., British Journal of Cancer, 81(2):342–349, 1999) |
| RU2 | (Eybde V.D., J. Exp. Med, 190 (12):1793–1799, 1999) |
| Folate binding protein | (Kim D., Anticancer Research, 19:2907–2916, 1999) |
| EGP-2 | (Heidenreich R., Human Gene Therapy, 11:9-19, 2000) |

What is claimed is:

1. A composition comprising all eight isolated epitopes: YLSGANLNV (SEQ ID NO:1), IMIGVLVGV (SEQ ID NO:2), KLBPVQLWV (SEQ ID NO:3), SMPPPGTRV (SEQ ID NO:4), KVAELVHFL (SEQ ID NO:5), YLQLVFGIEV (SEQ ID NO:6), RLLQETELV (SEQ ID NO:7), and, VVLGVVFGI (SEQ ID NO:8).

2. A composition of claim 1, further comprising an antigen presenting cell.

3. A composition of claim 2, wherein at least one epitope is bound to an HLA molecule on the antigen presenting cell, whereby a T lymphocyte receptor can bind to a complex of the HLA molecule and the epitope.

4. A composition of claim 2, wherein the antigen presenting cell is a dendritic cell.

5. A composition of claim 1, wherein each epitope is connected to another epitope by peptide bonds.

6. A composition of claim 1, further comprising an amino acid linker, wherein at least two of the epitopes are connected to each other by peptide bonds.

7. A composition of claim 1, further comprising a CTL epitope.

8. A composition of claim 1, further comprising an HTL epitope.

9. A composition of claim 8, wherein the HTL epitope is a pan-DR binding molecule.

10. A composition of claim 1, further comprising a liposome, wherein the epitopes are on or within the liposome.

11. A composition of claim 1, further comprising a lipid, wherein the lipid is attached to one of the epitopes.

* * * * *